US012605288B2

(12) United States Patent　　　　(10) Patent No.:　US 12,605,288 B2

Gelles et al.　　　　　　　　　　　(45) Date of Patent:　　Apr. 21, 2026

---

(54) OPHTHALMIC SHIELD AND THERAPEUTIC METHOD

(71) Applicant: Ocular Surface Innovations Inc., Jupiter, FL (US)

(72) Inventors: John Gelles, Teaneck, NJ (US); Jerome Legerton, Jupiter, FL (US)

(73) Assignee: Ocular Surface Innovations Inc., Jupiter, FL (US)

( * ) Notice: Subject to any disclaimer, the term of this patent is extended or adjusted under 35 U.S.C. 154(b) by 1124 days.

(21) Appl. No.: 17/547,933

(22) Filed: Dec. 10, 2021

(65) Prior Publication Data

US 2023/0181376 A1　　Jun. 15, 2023

(51) Int. Cl.
　　*A61F 13/12*　　　(2006.01)
　　*A61F 9/06*　　　(2006.01)

(52) U.S. Cl.
　　CPC ............ *A61F 13/124* (2013.01); *A61F 9/061* (2013.01)

(58) Field of Classification Search
　　CPC .. A61F 7/03; A61F 9/0017; A61F 9/04; A61F 9/061; A61F 13/124; A61F 2007/0004; A61F 2007/0054; A61F 2007/0088
　　See application file for complete search history.

(56) References Cited

U.S. PATENT DOCUMENTS

| 4,084,890 A | 4/1978 | Baron |
| 5,100,225 A | 3/1992 | Rothe |
| 6,093,868 A | 7/2000 | Sawano et al. |

| 8,459,793 B2 | 6/2013 | De Juan, Jr. et al. |
| 8,591,025 B1 | 11/2013 | De Juan, Jr. et al. |
| 8,678,584 B2 | 3/2014 | De Juan, Jr. et al. |
| 8,864,306 B2 | 10/2014 | De Juan, Jr. et al. |
| 8,926,096 B2 | 1/2015 | De Juan, Jr. et al. |
| 9,107,773 B2 | 8/2015 | De Juan, Jr. et al. |
| 9,241,837 B2 | 1/2016 | De Juan, Jr. et al. |
| 9,341,864 B2 | 5/2016 | De Juan, Jr. et al. |
| 9,395,558 B2 | 7/2016 | De Juan, Jr. et al. |

(Continued)

FOREIGN PATENT DOCUMENTS

WO　　　2014/148922 A2　　9/2014

OTHER PUBLICATIONS

Hirabayashi, Kristin E. et al., "Prospective, randomized, eye-to-eye comparison of a new silicone corneal shield versus conventional bandage contact lens after photorefractive keratoectomy," J Cataract Refract Surg 2019; 1782-1788; vol. 45, Iss. 12.

(Continued)

*Primary Examiner* — Jack Dinh

(74) *Attorney, Agent, or Firm* — Sheppard Mullin Richter & Hampton LLP

(57)　　　　　　　ABSTRACT

A method is disclosed, comprising obtaining at least one metric of an eye; and determining, based on the at least one metric of the eye, at least one parameter for manufacturing an ophthalmic shield to be worn on the eye. In some embodiments, the ophthalmic shield may have a minimum horizontal dimension of 18 mm and a minimum vertical dimension of 15 mm. In some embodiments, the ophthalmic shield may have a minimum horizontal dimension of 20 mm and a minimum vertical dimension of 17 mm. In some embodiments, the ophthalmic shield may have a minimum horizontal dimension of 26 mm and a minimum vertical dimension of 22 mm.

11 Claims, 42 Drawing Sheets

(56) References Cited

U.S. PATENT DOCUMENTS

| | | | |
|---|---|---|---|
| 9,423,632 | B2 | 8/2016 | De Juan, Jr. et al. |
| 9,465,233 | B2 | 10/2016 | De Juan, Jr. et al. |
| 9,498,385 | B2 | 11/2016 | De Juan, Jr. et al. |
| 9,740,025 | B2 | 8/2017 | De Juan, Jr. et al. |
| 9,740,026 | B2 | 8/2017 | De Juan, Jr. et al. |
| 9,810,921 | B2 | 11/2017 | De Juan, Jr. et al. |
| 9,851,856 | B2 | 12/2017 | De Juan, Jr. et al. |
| 10,036,900 | B2 | 7/2018 | De Juan, Jr. et al. |
| 10,039,671 | B2 | 8/2018 | De Juan, Jr. et al. |
| 10,191,303 | B2 | 1/2019 | De Juan, Jr. et al. |
| 2004/0181240 | A1 | 9/2004 | Tseng et al. |
| 2008/0148461 | A1 | 6/2008 | Guyuron et al. |
| 2008/0243095 | A1 | 10/2008 | Kaiser et al. |
| 2012/0310133 | A1 | 12/2012 | de Juan, Jr. et al. |
| 2014/0155800 | A1 | 6/2014 | de Juan, Jr. et al. |
| 2017/0329052 | A1 | 11/2017 | Chan |
| 2018/0129073 | A1 | 5/2018 | Meyers et al. |
| 2019/0101669 | A1 | 4/2019 | Yee et al. |
| 2020/0004047 | A1 | 1/2020 | de Juan et al. |
| 2020/0038240 | A1 | 2/2020 | de Juan, Jr. et al. |

OTHER PUBLICATIONS

Jacobs, Deborah S. et al., "Clear—Medical Use of Contact Lenses," Contact Lens and Anterior Eye, 2021; pp. 289-329; vol. 44.

PCT International Search Report and the Written Opinion mailed Mar. 3, 2023, issued in related International Application No. PCT/US2022/050624 (10 pages).

PCT International Search Report and the Written Opinion mailed Mar. 6, 2023, issued in related International Application No. PCT/US2022/050629 (11 pages).

Non-Final Office Action dated Jul. 1, 2024, issued in related U.S. Appl. No. 17/547,975 (30 pages).

Ehrmann, https://web.archive.org/web/20181212062103/http:/www.siliconehydrogels.org/editorials/may_05.asp (Year: 2018).

PCT International Preliminary Report on Patentability mailed Jun. 20, 2024, issued in related International Application No. PCT/US2022/050629 (9 pages).

PCT International Preliminary Report on Patentability mailed Jun. 20, 2024, issued in related International Application No. PCT/US2022/050624 (9 pages).

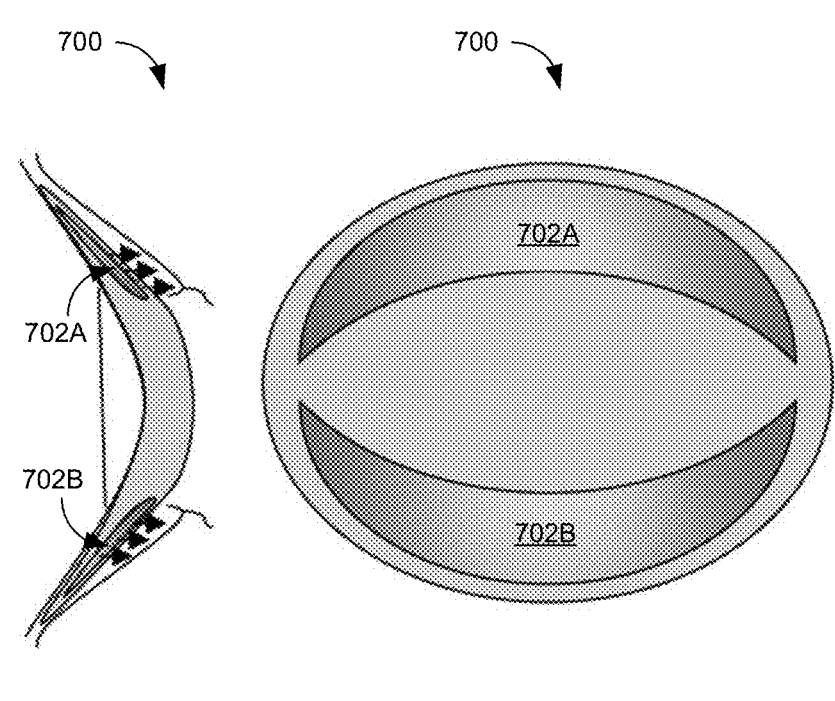
FIG. 7A                    FIG. 7B
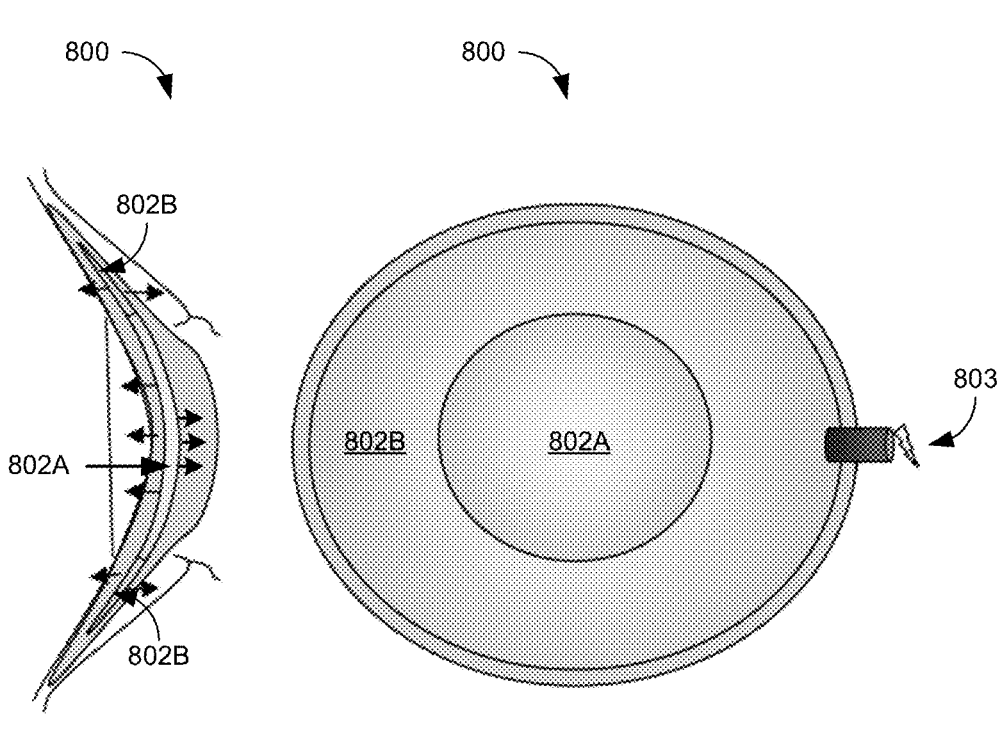
FIG. 8A                    FIG. 8B

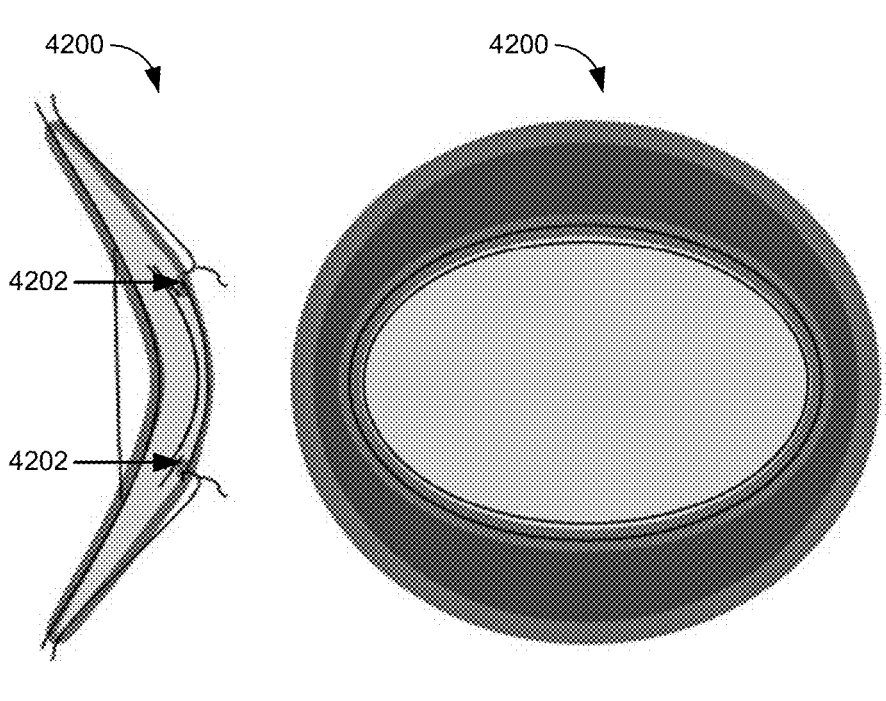
FIG. 42A                    FIG. 42B
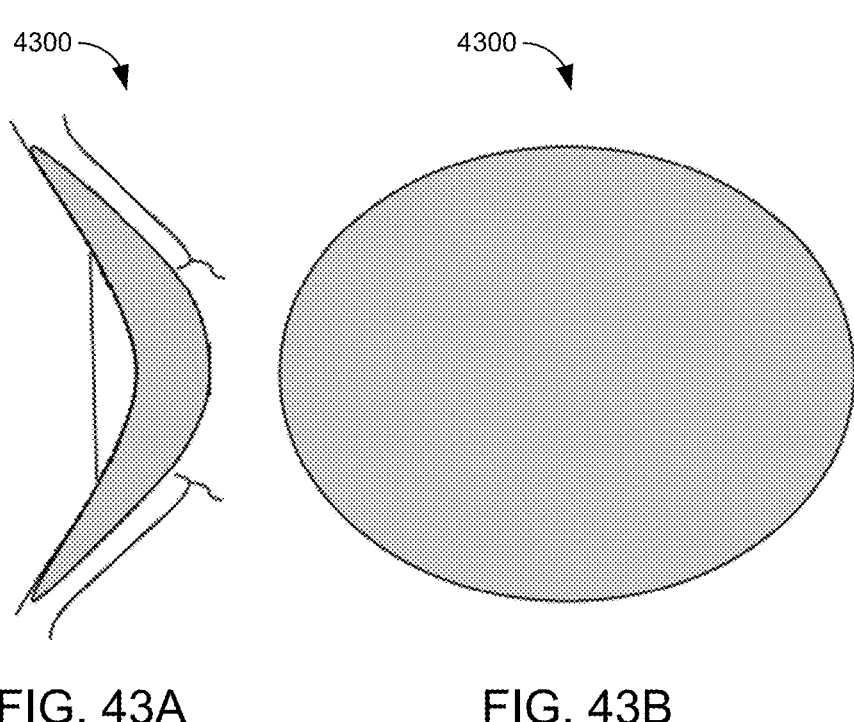
FIG. 43A                    FIG. 43B

7100

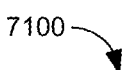

Obtain at least one metric of an eye of a patient.
7102

Determine, based on the at least one metric of the eye of the patient, at least one parameter for manufacturing an ophthalmic shield to be worn on the eye of the patient, wherein the ophthalmic shield has a minimum horizontal dimension of 18 mm and a minimum vertical dimension of 15 mm.
7104

Create cutting file and fabricate ophthalmic shield.
7106

Apply and evaluate ophthalmic shield.
7108

Dispense ophthalmic shield and conduct follow-up evaluation.
7110

FIG. 71

7200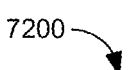

Obtain at least one metric of an eye of a patient.
7202

Determine, based on the at least one metric of the eye
of the patient, at least one parameter for
manufacturing an ophthalmic shield to be worn on the
eye of the patient, wherein the ophthalmic shield has a
minimum horizontal dimension of 20 mm and a
minimum vertical dimension of 17 mm.
7204

Create cutting file and fabricate ophthalmic shield.
7206

Apply and evaluate ophthalmic shield.
7208

Dispense ophthalmic shield and conduct follow-up
evaluation.
7210

FIG. 72

7300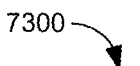

Obtain at least one metric of an eye of a patient.
7302

Determine, based on the at least one metric of the eye of the patient, at least one parameter for manufacturing an ophthalmic shield to be worn on the eye of the patient, wherein the ophthalmic shield has a minimum horizontal dimension of 26 mm and a minimum vertical dimension of 22 mm.
7304

Create cutting file and fabricate ophthalmic shield.
7306

Apply and evaluate ophthalmic shield.
7308

Dispense ophthalmic shield and conduct follow-up evaluation.
7310

FIG. 73

OPHTHALMIC SHIELD AND THERAPEUTIC METHOD

DESCRIPTION OF RELATED ART

The disclosed technology relates generally to an ophthalmic shield, and more particularly some embodiments relate to therapeutic ophthalmic apparatuses.

SUMMARY

In general, one aspect disclosed features an ophthalmic shield, comprising: a structure configured to be worn on the eye of a user for the protection of the eye. The ophthalmic shield may be applied for a single use for diagnostic purpose; for therapeutic purpose; as a protective shield during a surgical procedure or a non-surgical procedure; as an attachment to or carrier of medical or treatment devices; as drug delivery system, or as means of protecting an eye in a similar manner to a bandage contact lens or a therapeutic scleral lens. The ophthalmic shield of the present invention may or may not have a zone for optical correction.

In some embodiments the ophthalmic shield is worn on the eye of the user for extended purpose to protect the ocular surface from exposure in the presence or absence of a failure of the eye to fully close (lagophthalmos) as may be caused by trauma and burns, metabolic conditions such as hyperactive thyroid, neurologic conditions such as Bell's palsy, stroke, tumors, especially acoustic neuromas, or Möbius syndrome, congenital conditions such as eyelid coloboma, immunologic conditions, such as Guillain-Barré syndrome, or Stevens-Johnson syndrome, iatrogenic conditions such as exposure after oculoplastic or eyelid surgery or intracranial surgery-induced palsy, or lid conditions such as floppy eyelid syndrome, nocturnal lagophthalmos, or poor lid apposition, and the like.

In some embodiments the ophthalmic shield is worn on the eye of the user for extended purpose to protect the ocular surface from mechanical trauma as may be caused by the palpebral conjunctiva such as scarring from burns, trauma, or immunologic mediated disease such as Stevens Johnson syndrome or ocular pemphigoid, papillae such as those formed by immunologic or infectious conditions, such as vernal keratoconjunctivitis or Trachoma, or follicles such as those formed by infectious conjunctivitis, ocular surface dryness or friction caused by dry eye disease of various etiology such as Sjogren's syndrome, lid malposition such as entropion, iatrogenic conditions such as ocular sutures, corneal pathology such as dystrophy, keratitis, ulceration, epithelial defect, and reduced or loss of corneal sensitivity, and the like.

In some embodiments the ophthalmic shield has a posterior surface reservoir and is worn on the eye of the user for extended purpose to provide continuous lubrication to the ocular surface as may be needed after burns, trauma, post ocular surface surgery to aid in healing, pre operative ocular surface management, immunologic disease such as Stevens Johnson syndrome, after nuclear treatments with radiation or chemotherapy for cancer, ocular surface dryness or friction caused by dry eye disease of various etiology such as immunological conditions such as Sjogren's syndrome or certain medical conditions such genetic Familial dysautonomia, corneal pathology such as keratitis, ulceration, epithelial defect, and reduced or loss of corneal sensitivity, in lid malposition such as entropion, in iatrogenic conditions such ocular graft versus host or post refractive surgery dryness, and the like.

In general, one aspect disclosed features an ophthalmic shield, comprising: a structure configured to be worn on the eye of a user; the ophthalmic shield having dimensions that are substantially larger than soft or scleral contact lenses and configured to protect the eye in the presence of exposure due to the absence of normal eyelid function; to protect from mechanical trauma to the ocular surface or palpebral conjunctiva; or in the presence of hazards; or as an adjunct for surgical procedures; or for collecting biologic material such as microbiome; or for the delivery of therapeutic treatment or pharmaceuticals to the underlying eye or the overlying eyelids.

Some embodiments of the ophthalmic shield to be worn on the eye of the user for extended purpose to protect the ocular surface may be configured with components encapsulated in the ophthalmic shield. The components include and are not limited to: Electronic, osmotic, cosmetic, artificial iris, pinhole aperture, drug delivery, artificial secretion structures, thermal emittance, gels, sponges; electric current or electric fields for wound healing; stem cell and regenerative technologies; illumination sources, reflective or absorptive optical filters; systems for stimulation or inhibition of glands within the orbit or intraocular or extraocular muscles; lenses, prisms, occluders, fabrics, wires, or films; structures to create vaults or clearance from the underlying eye; structure to create rigidity or reduce modulus; sensors, electrochromic or photochromic filters; structures to create posterior or anterior shapes that differ from the underlying eye for the purpose of reshaping the cornea; structures for retaining a pre-determined shape of all or a portion of the shield; and impact resistant structures.

Some embodiments of the ophthalmic shield worn on the eye of the user for extended purpose to protect the ocular surface are made of a soft material. The material may be a hydrogel or silicone hydrogel material. More preferably, the primary substrate of the ophthalmic shield is a soft material having less than 2% water content. Preferably, the material may have an oxygen permeability of greater than $100\times10\text{-}11$ (cm2/sec) (mL O2)/(mL×mm Hg). One exemplary material is a silicone elastomer material, polydimethylsiloxane (PDMS). The species of PDMS with the United States Adopted Name lemafoconA and a measured ultra-high oxygen permeability of $778\times10\text{-}11$ (cm2/sec) (mL O2)/(mL× mm Hg) allows the thickness of the ophthalmic shield to approach 1 mm while delivering a required percentage of oxygen to the underlying cornea to maintain a desired physiological state. Similar ultra-high oxygen permeable medical grade biocompatible polymers may be suitable for the ophthalmic shield of the present invention.

Embodiments of the ophthalmic shield may include a container structure or a plate located at the nasal aspect, temporal aspect or elsewhere on or in the ophthalmic shield for the purpose of collecting biologic materials. In some embodiments, the plate may be detached from the ophthalmic shield for processing or laboratory testing.

Some embodiments comprise a coating or surface properties on the plate to assure retention of the biologic materials. In some embodiments the ophthalmic shield may be configured with a sponge, and, or a channel for collecting fluids and biologics and removing them from the ophthalmic shield while the shield is in place on the ocular surface or after the shield is removed from the ocular surface.

Some embodiments of the ophthalmic shield may include a fluid collection channel configured with a tube that may be connected to a mechanism having a suction force for aspirating fluids from the collection channel. In some embodiments, the collection channel is open in a superior aspect. In some embodiments, the collection channel is closed with the exception of at least one opening to allow for fluid transfer into the channel.

Some embodiments of the ophthalmic shield comprise a posterior, anterior, rounded circumferential edge, inner side of the extended double shield or entire surface configured to perform impression cytology wherein the ophthalmic shield collects cellular material from the surface of the eye, fornix, palpebral conjunctiva, lid margins, or eyelids.

Some embodiments of the ophthalmic shield are configured with microfluidic structures to capture tear fluid for analysis.

Some embodiments of the ophthalmic shield encapsulate a deformable wire, mesh or film, with the purpose of holding the shield in a shape configuration to conform to the globe or to deviate from the shape of the globe. The mesh may have a radial, rectilinear or other form for the purpose of achieving an appropriate shape when deformed. The shape of the wire mesh or film creates the shape of the shield due to the modulus of the shield material allowing the shield to accept the shape of the wire mesh or film.

In some embodiments the ophthalmic shield may contain other material layers that are soft or malleable that may be hardened. The shield may be formed and later exposed to thermal or electromagnetic radiation or other curing agents, the polymer or resin layers may be hardened to maintain a desired form to create the final shape of the shield.

Some embodiments of the ophthalmic shield may be configured with a channel or reservoir for administering therapeutics behind the ophthalmic shield. Macro or micro fluidic structures within the shield may facilitate this flow.

Some embodiments of the ophthalmic shield may be configured with macro-fluidic or micro-fluidic structures or drug release features for drug delivery while the user is wearing the ophthalmic shield.

Some embodiments of the ophthalmic shield are configured with encapsulated solids, gel, liquid, gas, or a combination for thermal emittance to the palpebral conjunctiva and eyelids.

Some embodiments of the ophthalmic shield are configured with flanges extending from the anterior shield surface for the purposes of serving as an eyelid speculum. These flanges may contain rigid material or expandable components to spread the lids. Additionally, the shield may be configured with a port for fluid delivery to the ocular surface to prevent dryness and a material layer serving as a sponge or a collection vat to collect excess fluid.

Some embodiments of the ophthalmic shield are configured with micro or nano pores to facilitate ion, fluid, and gas transfer through the shield.

Some embodiments of the ophthalmic shield include an electronically controlled filter with or without a light sensor. The filter may be used to protect the eyes from corneal flash burns such as those from welding or from disorientation from stun grenades. In other embodiments the electrochromic filters may also be used as a treatment for photophobia.

Some embodiments of the ophthalmic shield may contain an electrochromic filter and electromagnetic spectrum illuminator to reset circadian rhythm by creating a gradual dimming or darken of incoming light mimicking a transition from day to night and gradual increased illumination to mimic a dawn effect. The spectral distribution of the light may be varied independent from the luminance of the source.

Some embodiments of the ophthalmic shield contain a sensor or monitor such as but not limited to a pH, osmolarity, inflammatory biomarker, allergic biomarker, or particle meter and a function for immediate ocular irrigation with a change in measurement from a baseline value level. The meter may respond to smoke, allergens, caustic fumes, defense sprays, or other ocular irritants. The ocular irrigation flow rate may be varied, it may be intermittent, periodic or continuous. In one embodiment the flow rate may be much slower to mimic the continuous release of tears for treatment of dry eye symptoms and ocular surface disease.

Some embodiments of the ophthalmic shield are configured in a single piece with at least one slit, screw, snap, magnet, hook or other anchor point. Anchor points may be used for the purposes of gluing or suturing the shield to a material or gluing or suturing the shield to ocular and periocular tissue. The anchor points may allow for the attachment of adjunct devices to the ophthalmic shield during a procedure.

In some embodiments the shield has a multiple piece construction with hook, snap, magnetic, screw, plug, or slide together components, for encapsulation or envelopment of the shield in part or in whole with material such as an amniotic membrane or micropore paper for impression cytology. These properties may serve as a method to fill a posterior reservoir or cavity within the shield with therapeutics for delivery without removal of the shield from the eye.

In some embodiments the ophthalmic shield may be intended for single use during a surgical procedure for treatment of the eyelids or ocular surface. Some embodiments of the treatment device may be configured with a therapeutic zone to align with the ophthalmic shield when treating the upper and lower eyelids of the eye. The therapeutic zone may be configured to use one of fluid force, thermal energy, osmotic gradients, electromagnetic frequencies, electric current or electric fields, gas or vacuum pressures, chemical interaction or ultrasonic action with the ocular tissue. The therapeutic zone may be configured to deliver treatment to a full eyelid or may be configured to deliver localized treatment to a portion of the eyelid or ocular surface.

In some embodiments, the ophthalmic shield may have handles or extensions on the anterior surface that may be used for grasping for removal of the ophthalmic shield. Additionally, this extension may have troughs, sulcus, or channels in the surfaces to allow the lid margins to rest in them, these structures may be used to treat the lid margins while the lids are closed.

In some embodiments the ophthalmic shield may include at least one void where no material is present. The void may be at the perimeter of the ophthalmic shield to avoid contact with abnormal tissue including pinguecula, pterygium, symblepharon, filtration blebs and the like. In other embodiments the void(s) may be fully penetrating within the ophthalmic shield to allow for surgical procedures within the void or to create a well for applying gas, fluids, gels or solids or directly apply electromagnetic radiation to the portion of the eye underlying the void. By way of example, the riboflavin, acting as a photosensitizer in corneal cross linking may be placed within a central void of the ophthalmic shield of the present invention prior to exposure of the cornea to ultraviolet A radiation though the void in the ophthalmic shield.

In some embodiments the ophthalmic shield may contain an encapsulated impact resistant material such as polycarbonate with or without a surrounding system of tubular voids which may be used to create a system of collapsible channels to act as crumple zones to distribute force to protect the globe from and during impact.

In some embodiments the ophthalmic shield may include a single or multiple ports, vents, or channels for the purpose of fluid, gel or gas delivery and evacuation through or directly under the posterior shield. These ports, vents, or channels may be used in combination with sponges or valves to control flow or increase contact time with the ocular surface.

In some embodiments the ophthalmic shield may include thin zones or channels or other structural shapes placed solely on the posterior surface of the shield for creation of suction force. The ophthalmic shield, unlike a bandage contact lens, provides the benefit of being immobile. The suction force may serve the purpose of securing or docking the shield to the eye. The system may be valved for the attachment and detachment from an external vacuum apparatus.

In some embodiments the ophthalmic shield may include a large central void. The central void may be round or oval and with an inside diameter of 26 mm or less. The shield, unlike a contact lens, may have anterior extensions to form a type of soft speculum for the purpose of retaining at least one eyelid and holding the eye open or folding the eyelashes away from the ocular surface. The shield may have at least one extension for use as a lateral positioning handle to control centration of the void over the ocular surface.

In some embodiments the ophthalmic shield may include an encapsulation of a metal or other protective material covering the ocular surface with anterior projections which may accommodate a closed eye and apply treatment by electromagnetic, mechanical, or other therapy to at least one eyelid and area of periorbital skin.

In some embodiments the ophthalmic shield may contain a power source such as but not limited to a battery which is replaceable or rechargeable, an induction coil, or corded power source. The power source may reside in the shield on the ocular surface or be part of an externalized extension.

In some embodiments the ophthalmic shield may be worn for protection in industrial environments, during performance in sports, including in or under water, and for protection of the eyes from ballistic and electromagnetic weapons.

In some embodiments the ophthalmic shield has an expandable or collapsible edge allowing the device to increase or decrease in circumference. The expandable or collapsible edge may be useful to expand the device into the fornix for fornix sparing needs such as after Stevens Johnson syndrome or retract the device for insertion and removal into a small horizontal fissure, such as a lateral tarsorrhaphy.

In some embodiments the ophthalmic shield may contain prisms made of higher index materials to compensate for diplopia as a result of nerve palsy, tropia or phoria or other causes. The size, shape, and stability of the ophthalmic shield provides greater area and adherence than a contact lens for maintaining the position and orientation of a prism. Unlike a contact lens the thickness of the ophthalmic shield provides adequate space between the surfaces of the ophthalmic shield for an encapsulated prism.

In some embodiments the ophthalmic shield may contain material that has been designed for cosmetic purposes. This may include but is not limited to precious metals, stones, gems, plastics, metals, beads, lighting, glitter, fabrics, films, hand painted material, and reflective materials or other materials for cosmetic effect.

In some embodiments the ophthalmic shield may have an asymmetric or freeform circumferential shape to avoid contact with obstacles such as glaucoma blebs and drainage devices or extraocular muscle insertions. In some embodiments, unlike a contact lens, the large surface area and asymmetric shape may facilitate desired placement of an incorporated device, such as an electro stimulation device. For example, the desired placement of a device may be in the superior temporal orbit for simulation of the lacrimal gland.

In some embodiments of the ophthalmic shield, unlike a contact lens, may have two or more layers and may be stacked to create an ocular surface shield attached to an external lid shield. This space between shields may hold the lids or the shield may be secured to the lids via adhesive, by selected material properties, by encapsulated deformable wire, mesh or film, by spring force, or by magnets. In other embodiments, the multilayer shield may contain apparatuses to treat external lid, lash, lid margin or palpebral conjunctiva or the internal lid. The apparatuses to treat the external lid, lash, lid margin, meibomian glands or palpebral conjunctiva may have mechanical movement or thermal, or electromagnetic radiation function or may use the natural lid forces from blinking to provide the mechanical movement to treat the external lid, lash, lid margin, meibomian glands or palpebral conjunctiva.

In one embodiment, the multilayer ophthalmic shield may be used to treat the lid margin and lashes. The shield may include an adjunct device at the junction between the shields and lids that may include a rotating, translating, waterjet, ultrasonic or other apparatus to clean and debride the at least one lid margin. In other embodiments the multilayer shield may contain filters to protect the ocular surface while delivering electromagnetic radiation, radiofrequency, or intense pulsed light.

The ophthalmic shield may be provided in combination with accessories to create a specific procedure kit. The components of the kit include and are not limited to: instruments, collection plates, microscope slides, culture media, drugs, sponges, contact lenses, ocular impression material, ocular impression trays, external devices and power sources, amniotic membranes, stem cell and regenerative technologies.

In some methods, the kit is delivered first and then a derived impression is returned for analysis and the creation of a customized surgical shield is returned for one time use during a procedure.

In some embodiments the shield is ultrathin, allowing for enhanced flexibility and elasticity. The edge of the shield may contain a firm expandable lasso to allow for the expanding of the shield through a small opening such as a tarsorrhaphy so the shield can be expanded from fornix to fornix for stability. The expandable shield may be combined with other therapeutic treatments and coatings of the shield such as amniotic membranes.

In some embodiments the shield has thin zones specifically for the purpose of creating significant drape and also adherence to the surface of the eye for stability. For example, the ultra-high oxygen permeable material may also have ultra-high water-vapor permeability and the thin zones may create zones of adherence to the surface of the eye due to pervaporation of the post shield tear layer through the thin zones of the shield.

In general, one aspect disclosed features a method for an ophthalmic shield configured to be worn on the eye of a user, the method comprising: selecting an ophthalmic shield having parameters designed using biometric mean data of human or animal eyes. Alternatively, a method using clinical data to select design parameters may be used. The ophthalmic shield of the present invention is configured for human eyes to have a minimum horizontal dimension of 18 mm and a minimum vertical dimension of 15 mm; or more preferably, a minimum horizontal dimension of 20 mm and a minimum vertical dimension of 17 mm. In some embodiments, the horizontal dimension may be as large as 30 mm and the vertical dimension may be as large as 28 mm for human eyes. The minimum difference between horizontal and vertical dimensions is 0.1 mm.

In some embodiments, the dimensions may be significantly increased or decreased; for example, for large or small animal eyes, the shield may be as large as 60 mm in the horizontal dimension and 58 mm in the vertical dimension or as small as 1.2 mm in the horizontal dimension and 1 mm in the vertical dimension respectively.

Embodiments of the method for selecting the parameters using clinical data may include one or more of the following steps. In some embodiments, keratometry is used to select the base curve radius of a corneal zone of the ophthalmic shield, and an objective or subjective refraction may be used to determine the refractive power and a wavefront aberrometer may be used to determine a customized higher order aberration surface profile of the ophthalmic shield having an optic zone; and, horizontal-visible-iris-diameter also called horizontal white to white or horizontal corneal diameter and occasionally a vertical-visible-iris-diameter also called vertical white to white or vertical corneal diameter may be used to determine the corneal zone of the ophthalmic shield; and, at least one measurement of the sagittal depth of an eye at a chord outside the cornea may be used to determine the sagittal depth parameter of the ophthalmic shield over the sclera; and upper and lower lid position relative to the superior and inferior limbus may be used to determine the location of upper and lower rotational stabilization features, or lid speculum features on the anterior aspect of the ophthalmic shield; upper and lower lid fornix depths may be used to determine the vertical dimension of the ophthalmic shield and, the horizontal distance from the medial and lateral canthus or from landmarks placed at the medial and lateral canthus during left and right gaze may be used to determine the horizontal dimension of the ophthalmic shield; and measurements from the medial canthus to the nasal aspect of the cornea, and from the lateral canthus to the temporal aspect of the cornea may be used to determine the asymmetry of the horizontal dimensions of the ophthalmic shield from the geometric center of the ophthalmic shield; and, the measurement of the residual refraction or wavefront refraction and registration of the optic zone when a predicate lens or shield is placed on the eye may be used to determine the low and higher order aberration correction of a customized ophthalmic shield having an optic zone.

A method of fitting may be employed in which 16 shields are included, 4 diameters (small, medium, large, extra large) with 4 sagittal depths with 500 micron steps between them. The front surface of each shield may include a marker system used for objective measurement of rotation, translation, and decentration. The marker system may be printed, engraved or configured by materials within the substrate of the shield. For example, titanium dioxide that is detected by infra-red imaging may be placed on or in the shield. The pattern of the marker system may be configured as a circle and one radial mark to allow for vertical and horizontal center identification along with an angular orientation measurement component.

Some embodiments may employ a method of selecting the parameters of the posterior surface of the shield using an impression of the eye or apparatus that measures the ocular contour. In each case, a method of determining the registration of the surface features of the eye and the posterior surface of the ophthalmic shield may be required to allow registration of anterior optical features with or without rotational stabilization features.

In one embodiment, the method may include the application of a structure or material to the surface of the eye that transfers to the impression material or is detected by the ocular contour measuring device or that may be captured by the imaging device and used to provide registration.

In general, one aspect disclosed features a method for determining the parameters of an ophthalmic shield configured to be worn on the eye of a user, the method comprising: placing a marker or structure on the surface of the eye, capturing images of the surface of the eye including the pupil of the eye, the applied structure, cornea and sclera, or taking an impression of the ocular surface or measuring the ocular topography including the applied structure, cornea and sclera; and, determining the ocular contour of the eye in relationship to the applied structure and captured images of the surface of the eye including the applied structure, cornea and sclera. In one embodiment, the method includes subtracting the known thickness profile of the applied structure at its location in the captured image of the surface of the eye.

In some embodiments, one or methods of scanning the eye to determine geometric dimensions of the ophthalmic shield. The scanning methods may include Optical Coherence Tomography, Magnetic Resonance Imaging, Computed Tomography, or 3D camera or laser scanning or the like.

Embodiments of the method may include one or more of the following features. Some embodiments comprise analyzing the captured images to determine the ocular contour relative to the center of the pupil as a means of placing anterior ophthalmic shield features in relationship to the posterior ophthalmic shield shape features determined from the ocular impression or ocular contour determined by ocular topography technology.

In some embodiments the method of choosing the shield's back surface contour is matched to a digital model of the eye. In another related embodiment an optimized geometric design, created by an average of surface shapes in at least 8 meridians is created.

BRIEF DESCRIPTION OF THE DRAWINGS

The present disclosure, in accordance with one or more various embodiments, is described in detail with reference to the following figures. The figures are provided for purposes of illustration only and merely depict typical or example embodiments.

FIGS. 7A,B illustrate ophthalmic shields with embedded thermal or electromagnetic radiation sources that may be inward facing, outward facing, or both according to some embodiments of the disclosed technologies.

FIGS. 8A,B illustrate ophthalmic shields with embedded thermal or electromagnetic radiation sources that may be inward facing, outward facing, or both according to some embodiments of the disclosed technologies.

FIGS. 42A,B illustrate an ophthalmic shield having front edge encapsulation according to some embodiments of the disclosed technologies.

FIGS. 43A,B illustrate an ophthalmic shield having variable thickness to produce a smooth anterior shape according to some embodiments of the disclosed technologies.

FIG. 71 illustrates a flow chart for selecting the parameters of an ophthalmic shield according to some embodiments of the disclosed technology.

FIG. 72 illustrates a flow chart for selecting the parameters of an ophthalmic shield according to some embodiments of the disclosed technology.

FIG. 73 illustrates a flow chart for selecting the parameters of an ophthalmic shield according to some embodiments of the disclosed technology.

Figures 1A, 1B:
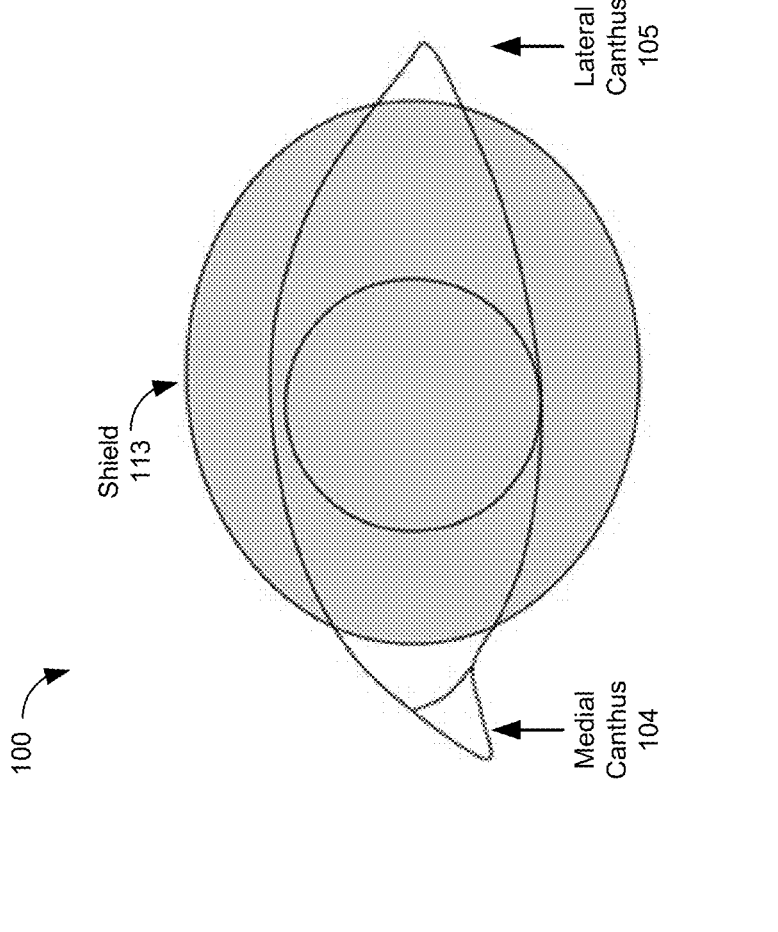
FIGS. 1A,B illustrate the anatomic structures of an eye with an ophthalmic shield according to some embodiments of the disclosed technologies.

The figures are not exhaustive and do not limit the present disclosure to the precise form disclosed.

DETAILED DESCRIPTION

Bandage or therapeutic contact lenses are frequently used following anterior segment ocular surgery and generally have little difference form contact lenses used for refractive correction except their regulatory market clearance as a therapeutic bandage lens. Soft standard and soft therapeutic bandage contact lenses are commercialized as single material, round, thin lenses with a diameter of less than 15.0 mm. In all cases the bandage lens material is water containing in the form of hydrogel and silicone hydrogel polymers. Bandage lenses are not commercialized in a size and shape intended to serve as an ophthalmic shield. Bandage lenses are created in a one size fits most eyes and the designs are related to a normal average cornea with the purpose of covering the cornea, however bandage lenses leave the greater ocular surface outside the cornea exposed.

Rigid gas permeable scleral lenses are commercialized in larger diameters than bandage lenses and occasionally in non-round shapes. Scleral contact lenses are used to correct irregular refractive errors from irregular corneal surface geometry and are used to manage some ocular surface disease and dry eye conditions. The difficulties in scleral lens application and removal are broadly reported in ophthalmic literature along with the high cost and need for customized fitting. Significant experience is needed to create a scleral lens that will maintain the ocular health, thus limited numbers of health care providers are capable of designing and implementing treatment with such lenses. The rigid material makes scleral lenses non-forgiving as misalignments of the lenses do not conform to the ocular surface like soft materials, instead complications arise from misalignment of scleral lenses. Additionally, designing and prescribing scleral lenses is time intensive, requiring a lathing process to create one lens at a time, which contributes to the amount of time a lens will take to be manufactured and delivered. Scleral lenses are not sterilizable except by electronic beam or gamma radiation. Electronic beam and gamma radiation technologies are not clinic based and are not cost effective for low numbers of devices to be sterilized. Rigid gas permeable scleral contact lenses are known to provide some ocular protection and good refractive correction.

However, bandage contact lenses and rigid gas permeable scleral lenses suffer from a number of shortcomings. Bandage contact lenses and rigid gas permeable scleral lenses are not suitable as ophthalmic shields during surgical treatment procedures of the eyelids for reason of the small diameter and the regular round shape of bandage lenses and for reason of the need for customization and high cost for the rigid gas permeable scleral lenses. Even in the event of a large set of pre-made scleral lenses, the rigid gas permeable material would require sterilization before re-use on subsequent patients' eyes and the lens material does not allow for usual and customary in-clinic or post fabrication autoclave sterilization.

There is a clear need for an ophthalmic shield for protection of the eye when conducting procedures on the eyelids and ocular surface. The need is particularly evident in the event it is found useful and efficient in the health care delivery system to delegate the lid surgery procedures to ancillary personnel. Examples of procedures where a protective ophthalmic shield may provide value to allow paramedical execution of services include lid debridement; chalazion and hordeolum removal; treatment for meibomian gland dysfunction; oculoplastic surgeries for neoplasm and other lesions; and other trauma and burn medical management.

In some implementations, unlike contact lenses, the ophthalmic shield may be employed as a means of collecting biologic materials including microbiome following a procedure by way of a collection plate for dry materials or a fluid collection system for materials rinsed and aspirated from the eye. The ophthalmic shield may also be used for impression cytology and the sampling of the tears for biochemical analysis including testing for inflammatory mediators.

Furthermore, the ophthalmic shield may be worn for ocular protection in individuals who manifest incomplete lid closure or the frank absence of eyelids from birth defects, burns and trauma. The ophthalmic shield may be fabricated with encapsulated or partially encapsulated components including electronic components, osmotic sponges or materials intended to treat edema, cosmetic films including photographic films, artificial iris, apertures including pinholes to provide vision correction, drug delivery materials and systems, electric current and electric field components to assist in wound healing or the reduction of corneal graft rejection, stem cell and other regenerative technologies, filters and lenses for vision correction and protection including but not limited to laser weapon protection and welding and protective structures for battlefield and athletic injury eye protection. Heretofore, soft hydrogel and silicone hydrogel contact lenses of conventional lens parameters and rigid gas permeable scleral contact lenses have not addressed the requirements for ophthalmic shields of the disclosed technology.

Embodiments of the disclosed technology address these and other shortcomings of conventional contact lens implementations. In some embodiments, performance of the ophthalmic shield may be enhanced by using ultra-high oxygen permeable material to allow for an increased thickness profile of the ophthalmic shield. Some embodiments may provide vertical and horizontal dimensions that are greater than those allowed by rigid materials due to potential for mechanical trauma caused by the rigid materials when contacting the ocular adnexa or limitations of rigid gas permeable contact lens production.

In some embodiments, the preferred soft anhydrous material of the ophthalmic shield allows for encapsulation of structures and components at far less cost and with greater ease than when encapsulating the same in rigid gas permeable material or hydrogel materials having high radial and linear expansion factors. The potential for single use and low per unit cost is a consideration attended to in the present invention as well as the ability to sterilize and re-use the device when appropriate.

In some embodiments, unlike contact lenses, the ophthalmic shield of the present invention is designed to serve as a lid speculum to retain the lids and prevent lid closure during a surgical procedure or otherwise. In some embodiments the ophthalmic shield has a region without material. For example, a central region of the ophthalmic shield may be without material to allow for intervention to the portion of the eye in the region that is not covered by the ophthalmic shield. The ophthalmic shield with the open region or void may also include the lid speculum features to retain the eyelids.

In some embodiments, the ophthalmic shield may have ports, macro-fluidic or micro-fluidic features for gas or liquid transfer or for liquid or gel aspiration, collection or delivery. The delivery though the features may include medications and other treatment enhancing materials. In some embodiments the ophthalmic shield is designed with appendages for collection of biologic materials including microbiome collection or surface modification to enhance impression cytology sampling.

In some embodiments, the ophthalmic shield may have a surface that is modified to allow for attached material for ocular treatment including medications, membranes or cell regeneration materials. The posterior, anterior or both surfaces of the ophthalmic shield may be modified. The modification may be in a single region of a surface to support localized treatment effects. For example, an amniotic membrane may be attached to the full surface of the ophthalmic shield or over the corneal region only or a stem cell tract may be placed in the ophthalmic shield over the limbal region of the underlying eye only.

In some embodiments, components may be encapsulated or placed on the surface of the ophthalmic shield. Some components may be electronically controlled and may utilize electrical power. For example, inward or outward facing thermal or electromagnetic radiation sources may be encapsulated in the ophthalmic shield of the present invention. Components for delivery of electric current or to produce electric fields may be present in the ophthalmic shield of the present invention for the purpose of enhancing healing.

In some embodiments, rigid materials may be encapsulated in the ophthalmic shield or attached to the surface of the ophthalmic shield. For example, a backbone or rigid skeleton may be encapsulated to provide greater resistance to bending or draping of the ophthalmic shield. The backbone may be encapsulated to create a vault between the posterior surface of the ophthalmic shield and the underlying eye in a predetermined region and thereby allowing for a space or reservoir between the ophthalmic shield and the underlying eye. A vault, space or reservoir may be produced by encapsulating curved rigid materials to make the region of the ophthalmic shield less deformable.

In some embodiments, the ophthalmic shield of the present invention may have optical properties to provide vision or refractive correction when worn. The optical correction region may be placed at a predetermined location to correspond to the center of the cornea, the center of the pupil, or the visual axis of the underlying eye. The optical correction may be spherical, sphero-cylindrical, multifocal and may incorporate registered higher order aberration correction.

In some embodiments, the ophthalmic shield may have features on or in the anterior surface for placement and retention of a contact lens to create a tandem or compound optical system. The contact lens may be rigid, soft or a hybrid combination of rigid and soft materials.

In some embodiments the features on or in the anterior surface may be designed to retain a miniature telescopic system. A preferred telescopic system is a Galilean design for the purpose of reducing the axial length. The telescopic system may be inserted into a feature in the anterior surface. In one embodiment the feature may be molded threads in the substrate of the ophthalmic shield. The feature in the ophthalmic shield may be partially penetrating with a fully intact posterior surface or fully penetrating and without a posterior surface. Other feature designs may be used to secure the miniature telescopic system.

In some embodiments, the ophthalmic shield of the present invention is designed to be worn on the surface or under water and may include a vision correction for the human eye to see clearly underwater. The optical design may have a region for vision correction in air and a second region for vision correction in water. Scleral contact lenses and conventional soft contact lenses do not fully cover the bulbar conjunctiva and the water medium may directly contact the uncovered and exposed bulbar conjunctiva. The ophthalmic shield of the present invention covers a far greater portion of the bulbar conjunctiva and offers greater protection to the tissue from the tonicity, pH, chemical toxicity and microbial content of the water medium. The ophthalmic shield for use in water may include on or more filters. A light polarizing filter may be placed in the vision path area for air. A red filter may be placed in the underwater vision correction path to enhance color perception at greater underwater depths.

In some embodiments, a method of selecting the parameters of the ophthalmic shield of the present invention are described. Table 1 presents the parameters of the ophthalmic shield and one or more methods for selecting individual parameters. Those skilled in the art appreciate that the rules may vary depending on the specific purpose of the shield.

TABLE 1

CLINICAL METRICS FOR DETERMINATION OF
OPHTHALMIC SHIELD FEATURES AND PARAMETERS

| Clinical Metric | Ophthalmic Shield Feature | Rule |
|---|---|---|
| Medial canthus to lateral canthus distance | Horizontal dimension | Equal to or less than up to 8 mm |
| Superior fornix to Inferior fornix distance | Vertical dimension | Equal to or less than up to 8 mm |
| Medial canthus to nasal limbus distance | Nasal scleral region | Equal to or less than up to 5 mm |
| Lateral canthus to temporal limbus distance | Temporal scleral region | Equal to or less than up to 5 mm |
| Superior limbus to superior fornix distance | Superior scleral region | Equal to or less than up to 5 mm |
| Inferior limbus to inferior fornix distance | Inferior scleral region | Equal to or less than up to 5 mm |
| Medial canthus to nasal limbus distance in temporal gaze | Nasal scleral region | Equal to or less than up to 5 mm |
| Lateral canthus to temporal limbus distance in medial gaze | Temporal scleral region | Equal to or less than up to 5 mm |
| Superior limbus to superior fornix distance in inferior gaze | Superior scleral region | Equal to or less than up to 5 mm |
| Inferior limbus to inferior fornix distance in superior gaze | Inferior scleral region | Equal to or less than up to 5 mm |
| Ocular impression or ocular contour imaging | Posterior shield shape | Equal to in scleral region and adjusted for desired corneal alignment or clearance |
| Horizontal visible iris diameter | Corneal horizontal diameter | Equal to or greater than up to 3 mm |
| Vertical visible iris diameter | Corneal vertical diameter | Equal to or greater than up to 3 mm |
| Upper and lower lid position in straight ahead gaze relative to upper and lower limbus | Anterior shield surface features including speculum and eyelid interfaces | Equal to, greater than or less than depending on the feature and its desired function |
| Apical corneal radius | Optic zone radius | Equal to or greater than up to 1.5 mm other than for intended corneal reshaping |
| Sagittal depth of sclera at a single semi-chord | Scleral zone depth | Equal or up to 400 microns greater plus microns of clearance of corneal zone from cornea |

TABLE 1-continued

CLINICAL METRICS FOR DETERMINATION OF
OPHTHALMIC SHIELD FEATURES AND PARAMETERS

| Clinical Metric | Ophthalmic Shield Feature | Rule |
|---|---|---|
| Sphero-cylindrical over-refraction of predicate lens or shield | Low order optical power | Calculated by use of vertex adjusted over refraction and predicate lens or shield power |
| Higher order aberrometry with simultaneous lens orientation imaging | Higher order aberration correction | Calculated by use of aberrometry and predicate lens or shield power and registration data |

The ophthalmic shield may be fabricated by diamond turning or conventional soft contact lens molding. While diamond turning with computer numerically controlled lathes allows for producing surface geometries discovered by scanning or impression molding, the size of the blanks or buttons required for the dimensions of the ophthalmic shield, the high cost of production, and the high waste of the material removed discourages the use of diamond turning. The high geometric diversity of human and animal eyes is expected to challenge the practical use of conventional soft contact lens molding.

In some embodiments, the lenses may be produced by molding the pre-polymerized material in custom molds or by use of multistage molding to allow for including components within the ophthalmic shield. For example, methods described in US Patent publication 20210347133, Apparatuses and methods for multistage molding of lenses, may be used.

An alternate embodiment includes the production of ophthalmic shield iterations with a mesh or film or lattice inside that may be dimensionally altered after fabrication to produce the shape required for an individual eye. A limited number of these iterations or preforms may be produced and inventoried by their dimensions. An impression mold or ocular topography may be used to produce a master in a rigid material that represents the shape of the eye. The master may be fabricated by computer numerically controlled diamond turning, ablation or other material removal methods or the like from a preformed semi-finished master. Additive methods of master fabrication such as 3D printing may be used.

One of the premade iterations of the ophthalmic shield may be selected, placed over the master that represents the shape of the eye and dimensionally altered to cause the ophthalmic shield to conform to the shape of the master. A preferred material for the ophthalmic shield for this method of production has a viscoelastic property that will allow for the required shape change.

A preferred material for the mesh or film or lattice may have the material property to hold the imparted shape at temperatures higher than body temperature and ambient temperatures where the device may be stored. Thermal modulation and/or mechanical forces may be used to cause the mesh or film to deform to allow the ophthalmic device to take the shape of the master. The mesh or film or lattice may be throughout the body of the ophthalmic shield or in a region outside the corneal zone of the ophthalmic shield. The mesh or film or lattice may have material properties that are tolerant to steam sterilization at 121 degrees Centigrade (121 C) for 30 minutes while also being thermoformable at a temperature above 121 C or pressure formable at any temperature that the ophthalmic shield material will tolerate. Or, the mesh or film or lattice may be tolerant to Electron Beam or Gamma radiation while being thermoformable or pressure formable at a lower temperature. For example, polymethylmethacrylate (PMMA) or other acrylates accepted by regulatory bodies for medical devices may be used as a thermoformable mesh or film material with sterilization of the shield including the mesh or film by use of Electron Beam or gamma radiation in order to avoid heat sterilization. Another example is the use of intra shield retained liquid or gel state monomers which can be formed and then polymerized with electromagnetic wavelength exposure such as Ultraviolet light. In some embodiments an aerogel may be used. For example, a mesoporous and biocompatible transparent silica aerogel may be produced by a sol-gel polymerization of tetraethyl orthosilicate to create a silica framework to form a non-collapsing structure while controlling the pore size of the gel.

The ophthalmic shield, systems and methods of selecting the parameters of the ophthalmic shield are further described by the following figures and their detailed descriptions. The described features may be used as building blocks in different combinations for different use cases.

FIGS. 1A,B illustrate the anatomic structures of an eye with an ophthalmic shield according to some embodiments of the disclosed technologies. FIG. 1A is a cross-sectional view of an eye with the ophthalmic shield in place. FIG. 1B is a front view of the eye with the ophthalmic shield in place. The eye and adnexa 100 include the cornea 101, the sclera covered by the bulbar conjunctiva 102, the corneal-scleral junction or limbus 103, the medial canthus 104, lateral canthus 105, the upper lid 107 with the upper lash line 108 and the upper fornix 109, the lower lid 110 with the lower lash line 111 with the lower fornix 112. The maximum horizontal dimension of the ophthalmic shield 113 may be less than or greater than the distance from the medial canthus 104 to the lateral canthus 105; and the maximum vertical dimension may be less than or greater than the distance from the upper fornix 109 to the lower fornix 112. In some embodiments the horizontal dimension may extend beyond the canthi to provide full ocular surface coverage even while in different positions of gaze.

Figure 2A:
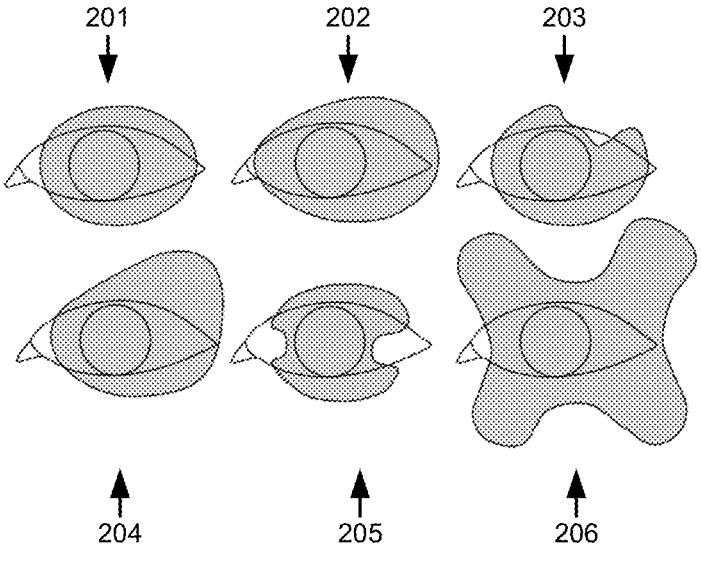
FIG. 2A illustrates ophthalmic shields to be worn on an eye and having different outer perimeter shapes according to some embodiments of the disclosed technologies.
Figure 2B:
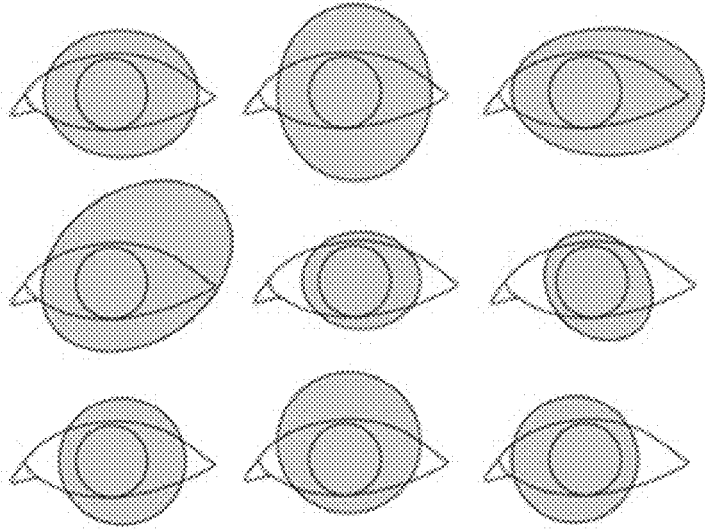
FIG. 2B illustrates ophthalmic shields having different sizes and shapes according to some embodiments of the disclosed technologies.
Figure 2C:
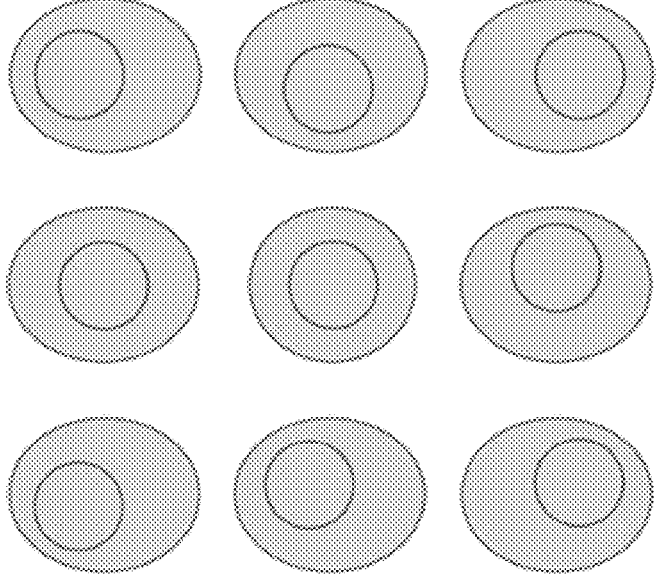
FIG. 2C illustrates ophthalmic shields having displaced optic and corneal zones according to some embodiments of the disclosed technologies.

FIG. 2A illustrates ophthalmic shields to be worn on an eye and having different outer perimeter shapes according to some embodiments of the disclosed technologies. While several shapes are disclosed and depicted, it should be understood that any shape can be created based on the particular application. Some of the ophthalmic shields include sections removed to avoid contact with abnormal ocular surface structures or extensions to cover ocular surface structures. The ophthalmic shields may have different horizontal to vertical aspect ratios. For example, oval ophthalmic shield 201 has a lower aspect ratio than "hen egg" ophthalmic shield 202. The ophthalmic shield may have a regular perimeter like ophthalmic shield 201 or 202, or may have an irregular perimeter for avoidance of contact of a tissue abnormality or devices such as glaucoma filtering devices like ophthalmic shield 203. The ophthalmic shield may have an eccentric perimeter like ophthalmic shield 204. For example, the eccentricity (also referred to as extensions or amorphous extensions) may be placed under or near the lacrimal gland. The ophthalmic shield may have medial and/or lateral cutouts, like ophthalmic shield 205. For example, the cutouts may be selected to avoid pinguicula. The ophthalmic shield may have other cutout or extension arrangements, like ophthalmic shield 206. For example, the extensions may be selected to avoid extra ocular muscle insertions. FIG. 2B illustrates ophthalmic shields having different sizes and shapes according to some embodiments of the disclosed technologies. FIG. 2C illustrates ophthalmic shields having displaced optic and corneal zones according to some embodiments of the disclosed technologies.

Figures 3A, 3B:
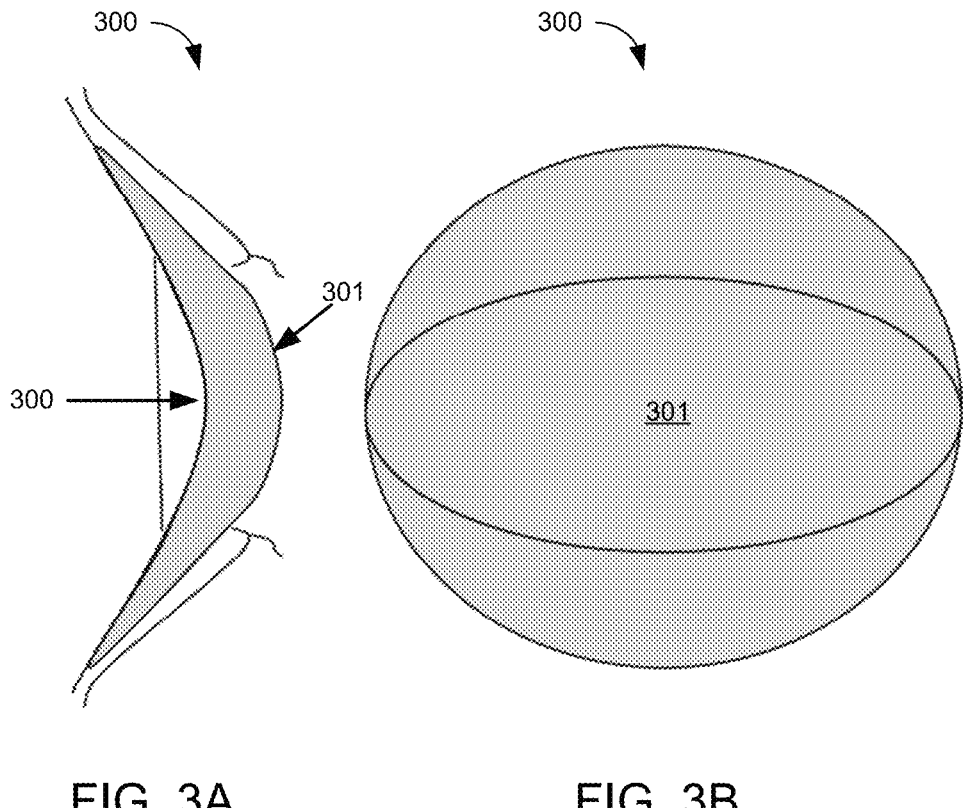
FIGS. 3A,B Illustrates an ophthalmic shield with lid separation geometry for lid placement or access to the lid margins according to some embodiments of the disclosed technologies.

FIGS. 3A,B Illustrates an ophthalmic shield 300 with lid separation geometry for lid placement or access to the lid margins according to some embodiments of the disclosed technologies. Ophthalmic shield 300 may be placed under the lids to protect the ocular surface from mechanical abrasion during lid procedures. Ophthalmic shield 300 may have a central region 301 of increased thickness with sloped protrusion. This increased thickness with sloped protrusion may push the lid margins in an anterior direction, tilt the lids, and provide greater access to the lid margins and lashes when manipulating or treating the lid margins during a medical procedure.

Figures 4A, 4B, 4C:
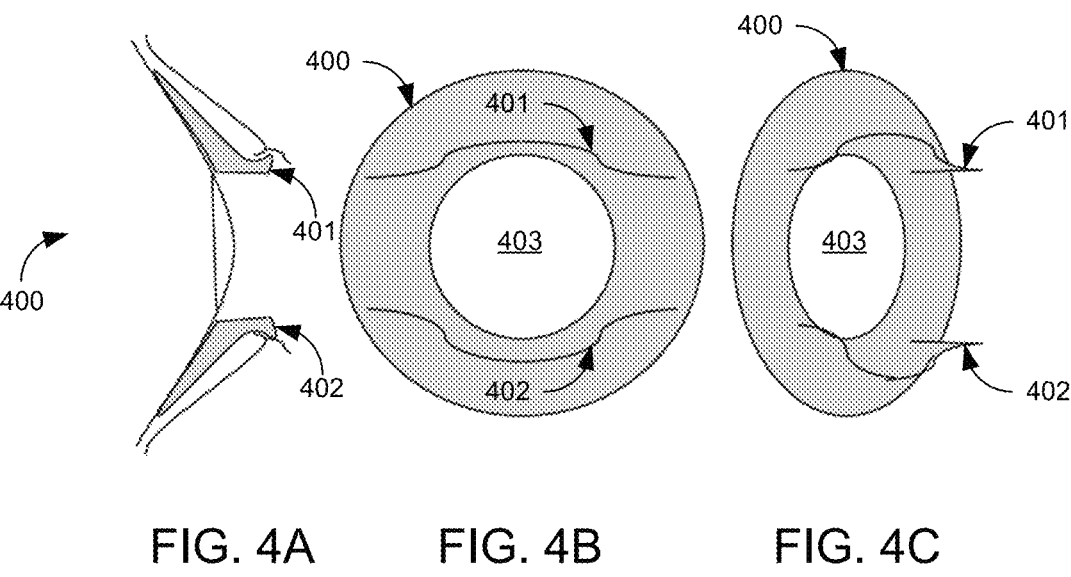
FIGS. 4A,B,C Illustrate an ophthalmic shield with lid speculum features and a region having a void of no material to allow for access to the underlying eye according to some embodiments of the disclosed technologies.

FIGS. 4A,B,C Illustrate an ophthalmic shield 400 with lid speculum features and a region having a void of no material to allow for access to the underlying eye according to some embodiments of the disclosed technologies. Ophthalmic shield 400 includes an upper lid speculum 401, a lower lid speculum 402 and a central void or opening 403 to allow for administration of fluids, gels, or solids; or for conducting a surgical procedure on the exposed cornea. Additionally, this ophthalmic shield may be encapsulated with specimen collection material to collect from the bulbar and palpebral conjunctiva and the lid margin.

Figures 5A, 5B, 5C:
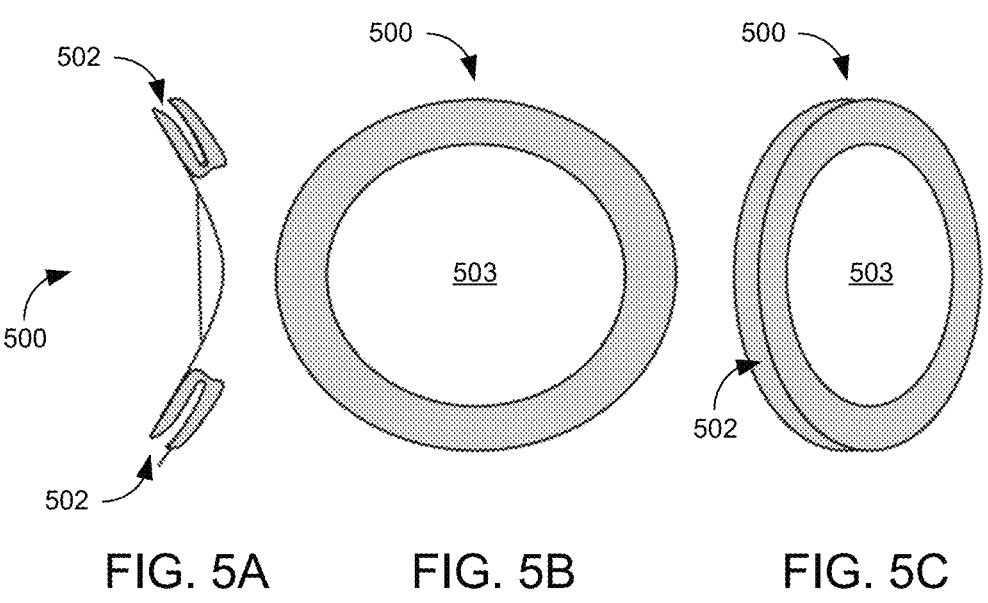
FIGS. 5A,B,C Illustrate an ophthalmic shield with lid speculum features and a region having no material to allow for access to the underlying eye according to some embodiments of the disclosed technologies.

FIGS. 5A,B,C Illustrate an ophthalmic shield 500 with lid speculum features and a region having no material to allow for access to the underlying eye according to some embodiments of the disclosed technologies. Ophthalmic shield 500 includes an annular channel 502 into which the eyelids fit, as shown in FIG. 5A. Ophthalmic shield 500 also includes a central void or opening 503 to allow for administration of fluids, gels, or solids; or for conducting a surgical procedure on the exposed cornea. The void may be used to aid in ophthalmic imaging.

Figures 6A, 6B, 6C:
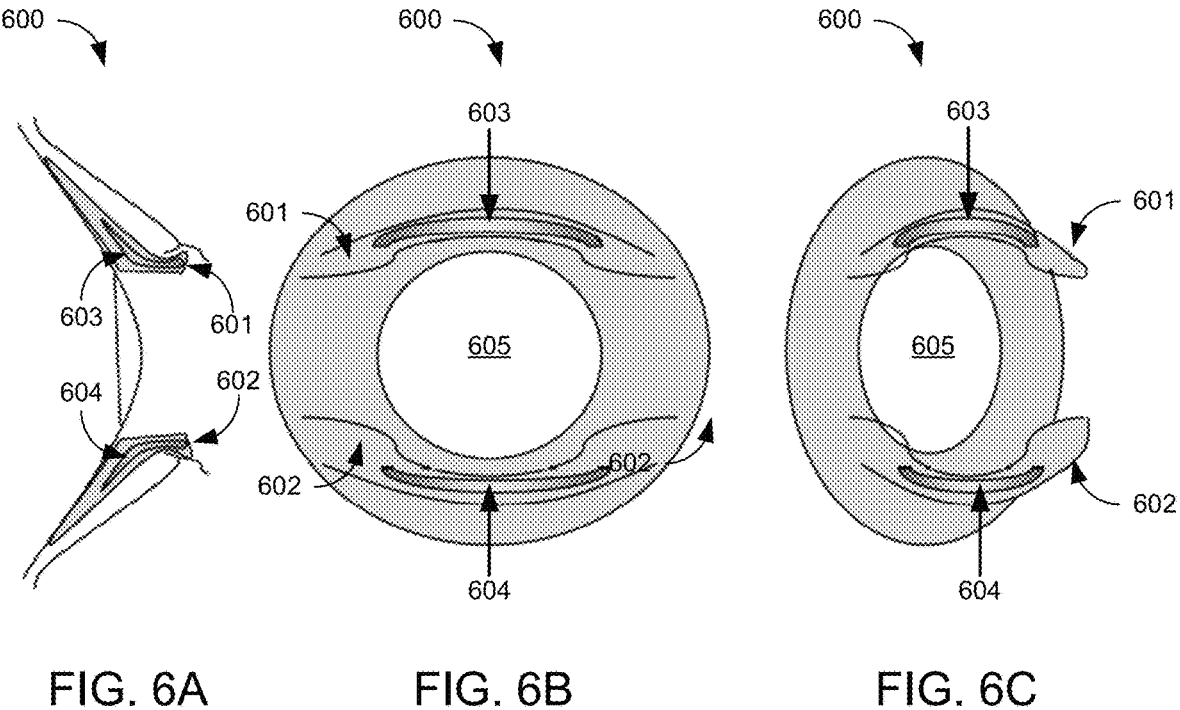
FIGS. 6A,B,C Illustrate an ophthalmic shield with an upper lid speculum and lower lid speculum with rigid encapsulated material for increased strength and rigidity to increase lid retention, according to some embodiments of the disclosed technologies.

FIGS. 6A,B,C Illustrate an ophthalmic shield 600 with an upper lid speculum 601 and lower lid speculum 602 with rigid encapsulated material 603, 604, respectively, for increased strength and rigidity to increase lid retention, according to some embodiments of the disclosed technologies. Ophthalmic shield 600 includes posterior surface features 605 to increase adherence to the ocular surface and a central void or opening 605 to allow for administration of fluids, gels, or solids; or for conducting a surgical procedure on the exposed cornea.

FIGS. 7A,B and 8A,B illustrate ophthalmic shields with embedded thermal or electromagnetic radiation sources that may be inward facing, outward facing, or both according to some embodiments of the disclosed technologies. The radiation sources may be made of a gel or circulating liquid. Additionally, these may contain materials which create endothermic or exothermic reactions to create heat or cold. The radiation sources may apply heat or cold. Referring to FIGS. 7A,B, an ophthalmic shield 700 includes two crescent-shaped embedded thermal or electromagnetic radiation sources 702A,B that face outward, as shown by the arrows, for treating the eyelids. Additionally, this 702A and 702B may be connected to an external circulatory system to circulate heated or cooled gel or liquid. There may be an anterior placement or posterior placement to more closely treat the inner eyelids or the scleral respectively. Additionally, the inner or outer interface may contain insulating or reflecting film to more precisely direct the treatments.

FIGS. 8A,B, show an ophthalmic shield 800 includes two electromagnetic radiation sources 802A,B, 802A over the cornea, and 802B over the sclera. Both 802AB can project inward, outward, or both, with patterned, focal, or micro sectoral control/delivery, which may be programed or guided by diagnostics, with variable powers, wavelengths or combination of wave lengths and variable timing for each section, separately or concurrently, to treat the cornea, eyelids, and sclera or any combination. The ophthalmic shield 800 may include a power source 803. It should be appreciated that the embodiments of FIGS. 7 and 8 may be used, wholly or partially, in conjunction with other embodiments described herein.

Figures 9A, 9B:
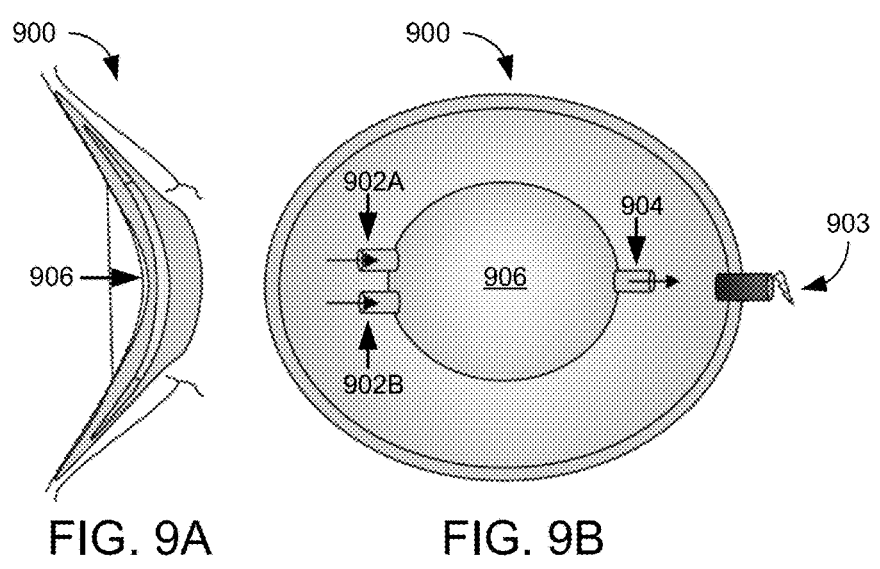
FIGS. 9A,B depict an ophthalmic shield with two inlet ports and an outlet port for transfer of liquids or gases to and from a space between the shield and the eye according to some embodiments of the disclosed technologies.

FIGS. 9A,B, 10A,B, AND 11A,B Illustrate ophthalmic shields with ports for transfer of liquids or gases to and from a post shield space according to some embodiments of the disclosed technologies. Each of these embodiments may or may not include the electromagnetic radiation sources 802A, B, 802A of the embodiment of FIG. 8. Additionally shield may be in contact with the eye in the area labeled space and only have separation for the shield from the cornea when a media (gas, liquid or gel) is introduced which creates a space or spreads like a drop between microscope slides.

FIGS. 9A,B depict an ophthalmic shield 900 with two inlet ports 902A,B and an outlet port 904 for transfer of liquids or gases to and from a space 906 between the shield 900 and the eye according to some embodiments of the disclosed technologies. The drainage may be by suction, or may be passive. The ophthalmic shield 900 may include a power source 903 and one or more thermal or electromagnetic radiation sources, for example as shown in FIGS. 8A,B.

Figures 10A, 10B:
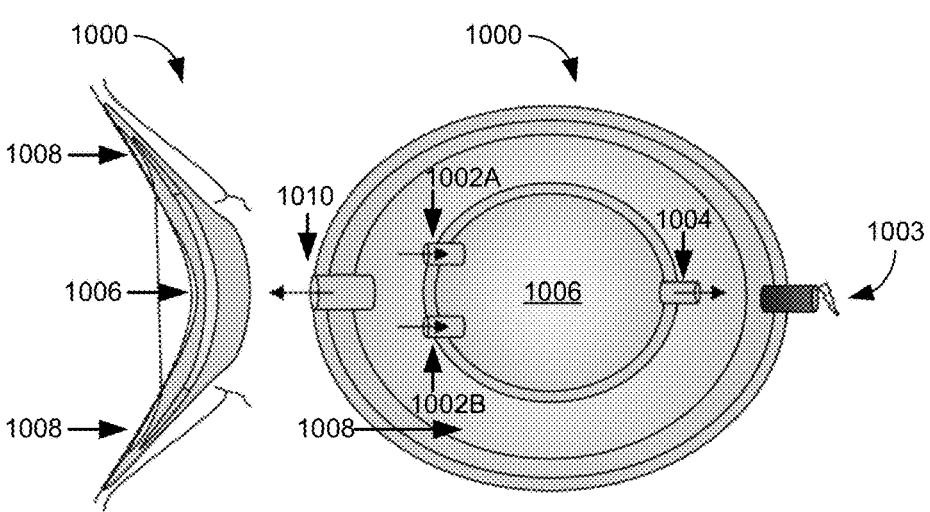
FIGS. 10A,B depict an ophthalmic shield with two inlet ports and an outlet port for transfer of liquids or gases to and from a space between the shield and the eye according to some embodiments of the disclosed technologies.

FIGS. 10A,B depict an ophthalmic shield 1000 with two inlet ports 1002A,B and an outlet port 1004 for transfer of liquids or gases to and from a space 1006 between the shield 1000 and the eye according to some embodiments of the disclosed technologies. The drainage may be by suction, or may be passive. The ophthalmic shield 1000 may include a posterior surface channel 1008 for docking to the eye. The ophthalmic shield 1000 may include a suction tube 1010, with or without a valve, for attaching and detaching the shield 1000 to the eye through regulation of suction. The ophthalmic shield 1000 may include a power source 1003 and one or more thermal or electromagnetic radiation sources, for example as shown in FIGS. 8A,B.

Figures 11A, 11B:
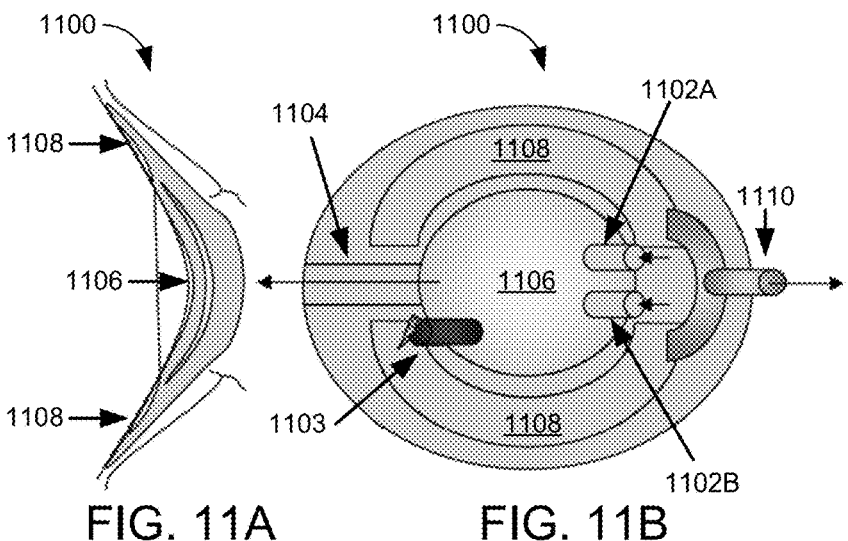
FIGS. 11A,B depict an ophthalmic shield with two inlet ports and an outlet space or channel for transfer of liquids or gases to and from a space between the shield and the eye according to some embodiments of the disclosed technologies.

FIGS. 11A,B depict an ophthalmic shield 1100 with two inlet ports 1102A,B and an outlet space or channel 1104 for transfer of liquids or gases to and from a space 1106 between the shield 1100 and the eye according to some embodiments of the disclosed technologies. The drainage may be by aspiration via 1102AB, or may be passive. The ophthalmic shield 1100 may include multiple posterior surface channels 1108 for docking to the eye. The ophthalmic shield 1100 may include a pressure tube 1110, with or without a valve, for attaching and detaching the shield 1000 to the eye through regulation of negative and positive pressure. The ophthalmic shield 1100 may include a power source 1103 and one or more thermal or electromagnetic radiation sources, for example as shown in FIGS. 8A,B.

Figures 12A, 12B, 13A, 13B, 14A, 14B:
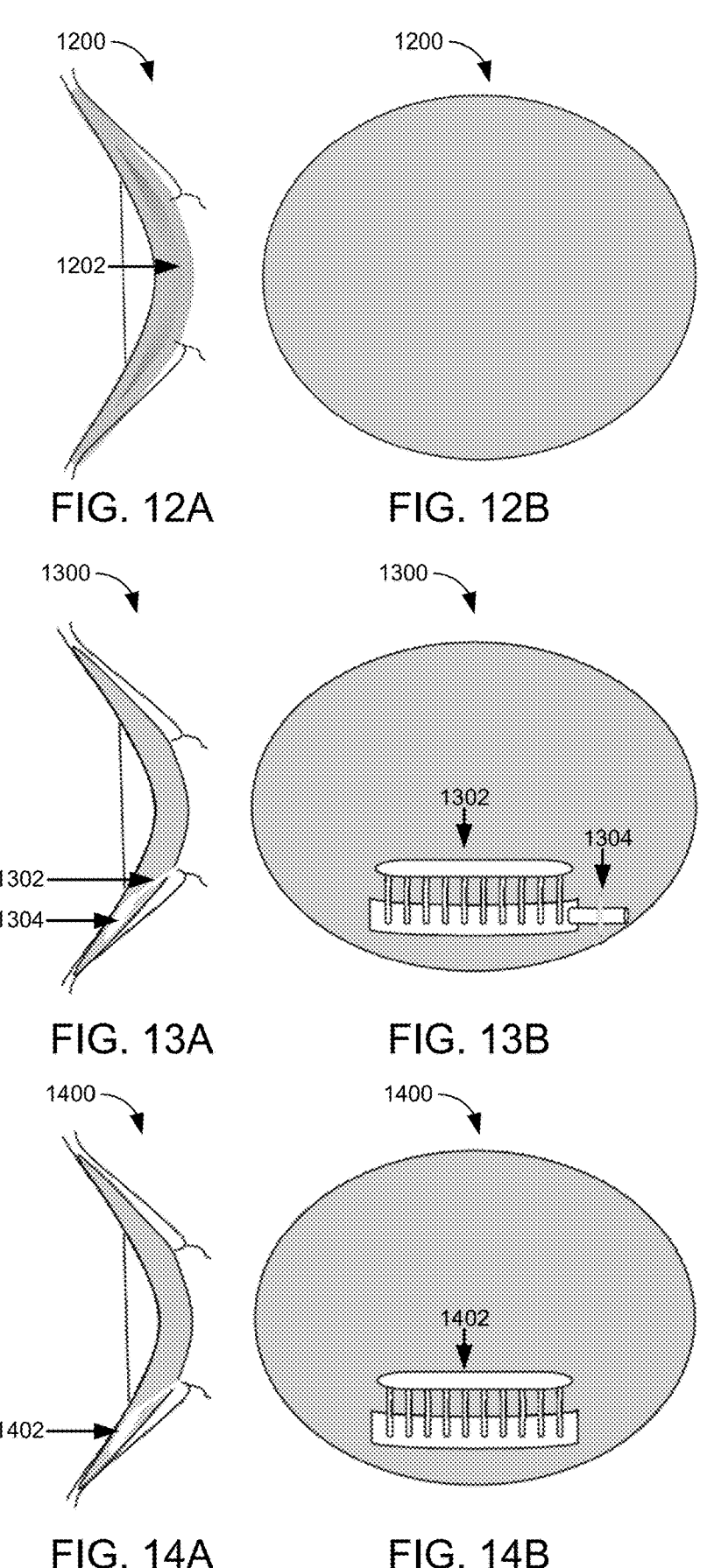
FIGS. 12A,B illustrate an ophthalmic shield with encapsulated shield core for eye protection or modulation of light transmission according to some embodiments of the disclosed technologies.
FIGS. 13A,B illustrate an ophthalmic shield having a fluid collection or delivery structure and an aspiration tube according to some embodiments of the disclosed technologies.
FIGS. 14A,B illustrate an ophthalmic shield having a fluid collection or delivery structure according to some embodiments of the disclosed technologies.

FIGS. 12A,B illustrate an ophthalmic shield 1200 with encapsulated shield core 1202 for eye protection or modulation of light transmission according to some embodiments of the disclosed technologies. The ophthalmic shield 1200 may be made of PDMS. The shield core 1202 may be made of metal, plastic, filters, and similar materials.

FIGS. 13A,B and 14A,B illustrate ophthalmic shields having fluid collection or delivery system and aspiration structures of the disclosed technology.

FIGS. 13A,B illustrate an ophthalmic shield 1300 having a fluid collection or delivery structure 1302 and an aspiration tube 1304 according to some embodiments of the disclosed technologies. There can exist more than one structure, separate or connected, with opening to the front, back, or both of the shield, in multiple locations. The structure 1302 is open to the shield surface and for fluid collection may include tubes, media for testing, or similar components, when used as a fluid delivery structure the bank may hold a fluid and by blink force or aspiration via 1304 may excrete fluid or gel. The ophthalmic shield 1300 may have a front surface opening for capturing or delivering ocular fluids.

FIGS. 14A,B illustrate an ophthalmic shield 1400 having a fluid collection or delivery structure 1402 according to some embodiments of the disclosed technologies. There can exist more than one structure, separate or connected, with opening to the front, back, or both of the shield, in multiple locations. The structure 1402 is open to the shield surface and may include tubes, media for testing, or similar components, when used as a fluid delivery structure the bank may hold a fluid and by blink force or passively excrete fluid or gel. The ophthalmic shield 1400 may have a front surface opening for capturing or delivering ocular fluids.

Figure 15:
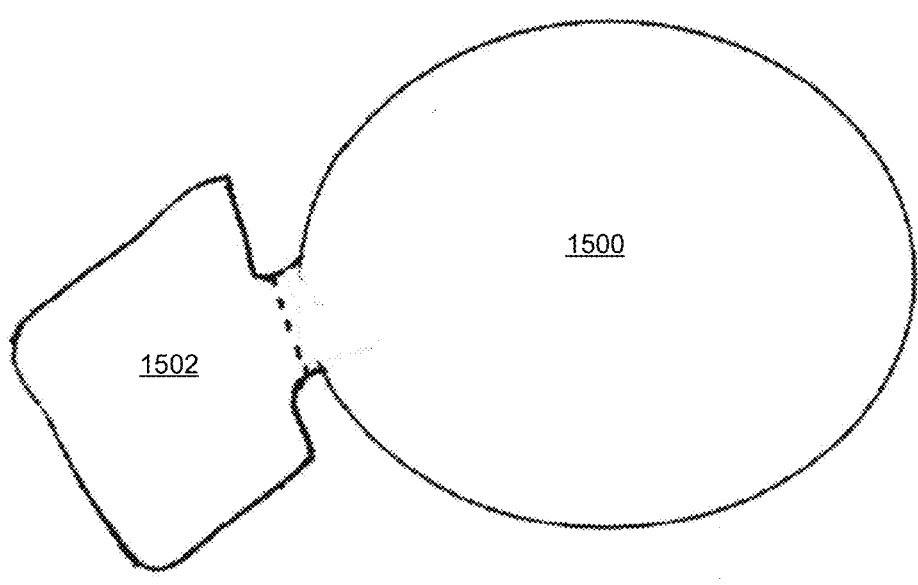
FIG. 15 illustrates an ophthalmic shield having a nasal plate for the collection of biologic material according to some embodiments of the disclosed technologies.

FIG. 15 illustrates an ophthalmic shield 1500 having a nasal plate 1502 for the collection of biologic material according to some embodiments of the disclosed technologies. The nasal plate 1502 may rest on the medial or lateral canthus of the eye. The ophthalmic shield 1500 and the nasal plate 1502 may be fabricated as a single piece, or as two pieces that connect. This plate may have culture media, microscope slides, or other material suitable for biologic material collection. In some embodiments, these features may be combined with the disclosed speculum featured in FIG. 4,5,6 or in combination with any of the described embodiments of the disclosed technologies. Such a combination may allow for a prep platform. For example, the prep platform may be used during a keratoplasty so the donor cornea could be placed on the plate to be very close to the surgery rather than being on a distant prep table.

Figures 16A, 16B:
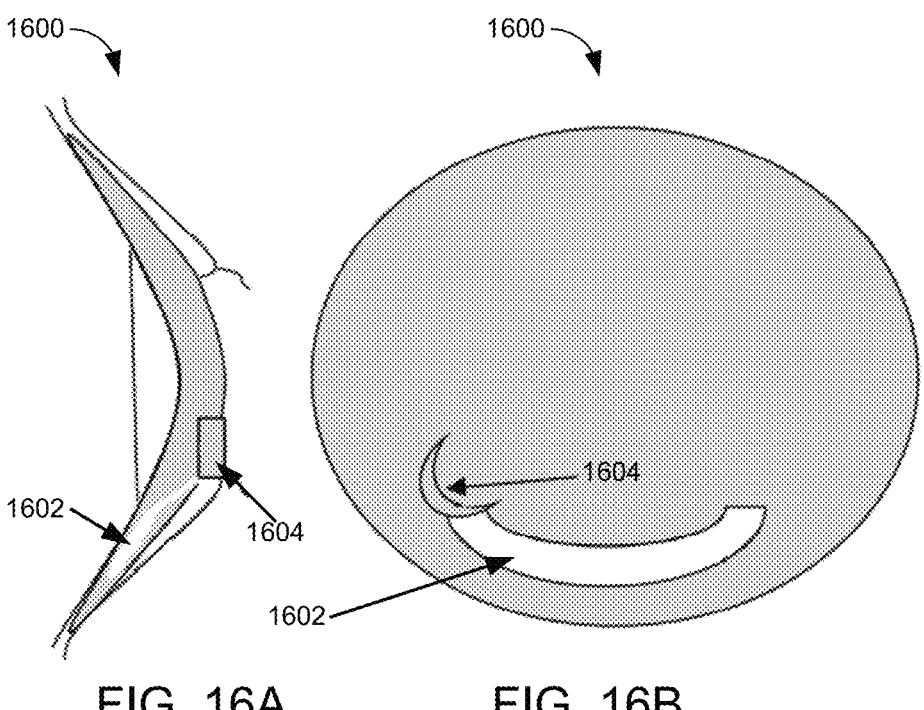
FIGS. 16A,B illustrate an ophthalmic shield for biological material collection according to some embodiments of the disclosed technologies.

FIGS. 16A,B illustrate an ophthalmic shield 1600 for biological material collection according to some embodiments of the disclosed technologies. The ophthalmic shield 1600 may have a pocket 1602 for storing the biological materials. The ophthalmic shield 1600 may have a front surface collection scoop 1604. The front surface collection scoop 1604 may rest on the lower lid for direction of fluid and collected materials.

Figures 17A, 17B:
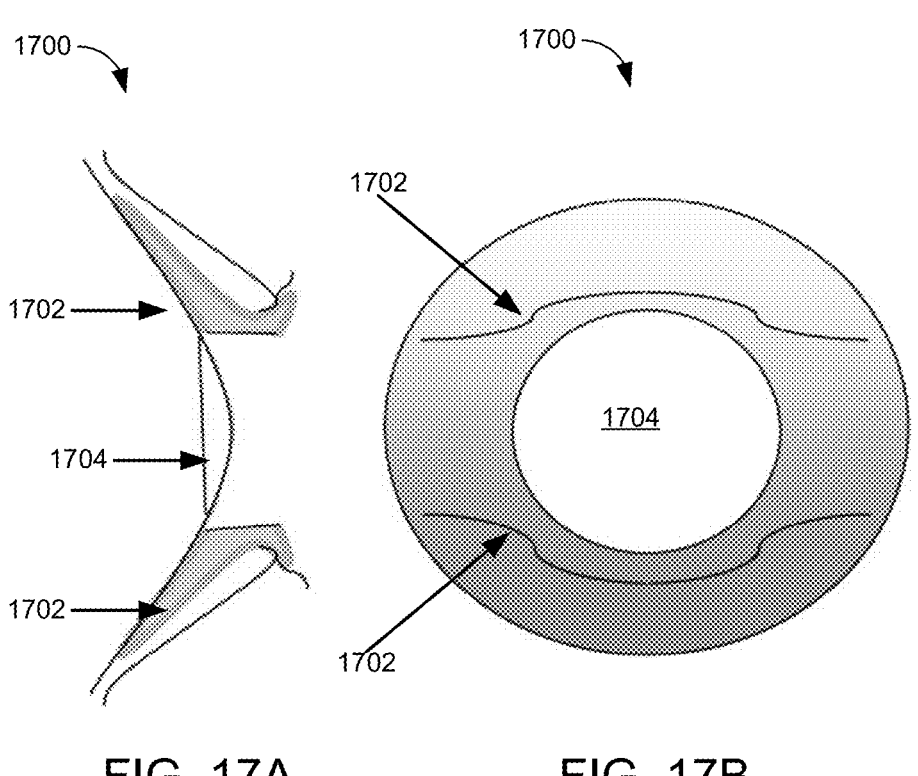
FIGS. 17A,B Illustrate an ophthalmic shield with lid speculum features and a region having no material to allow for access to the underlying eye according to some embodiments of the disclosed technologies.

FIGS. 17A,B Illustrate an ophthalmic shield 1700 with lid speculum features and a region having no material to allow for access to the underlying eye according to some embodiments of the disclosed technologies. Ophthalmic shield 1700 includes an upper and lower lid speculum 1702 and a central void or opening 1703 to allow for administration of fluids, gels, or solids; for avoiding cornea contact during impression cytology; or for conducting a surgical procedure on the exposed cornea. In some embodiments, ophthalmic shield 1700 may encapsulate material for impression cytology. The material may include micro pore paper or similar materials and may also be combined with the collection plate from FIG. 15.

Figures 18A, 18B:
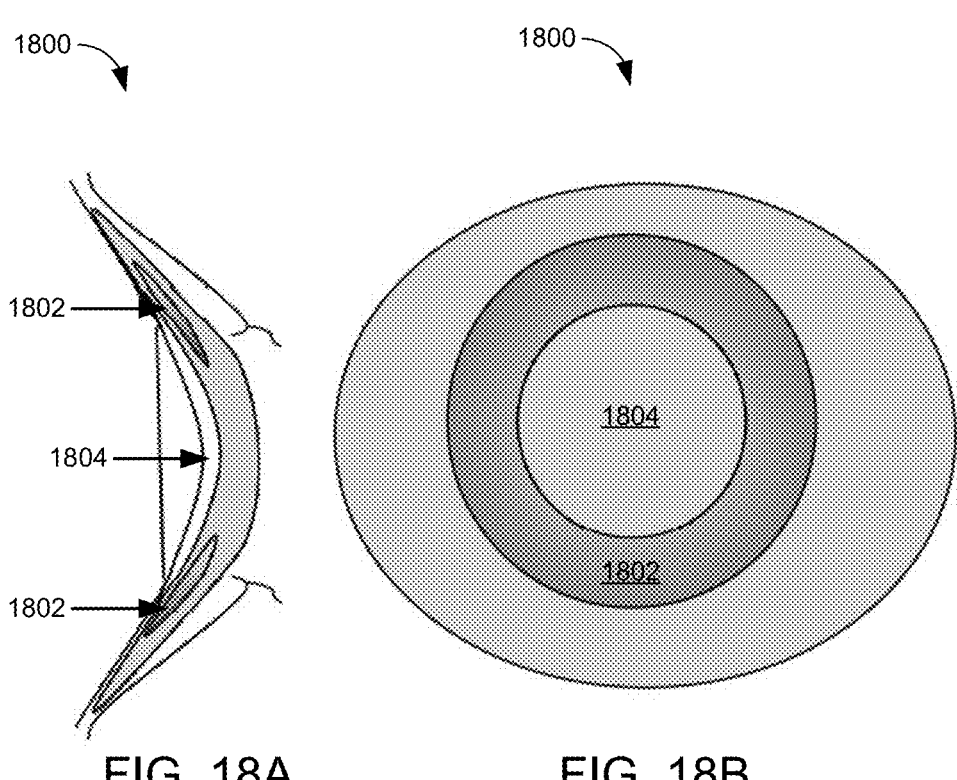
FIGS. 18A,B illustrate an ophthalmic shield having an annular rigid encapsulated structure to facilitate and maintain a post shield reservoir to offset the low modulus of the shield material according to some embodiments of the disclosed technologies.

FIGS. 18A,B illustrate an ophthalmic shield 1800 having an annular rigid encapsulated structure 1802 to facilitate and maintain a post shield reservoir 1804 to offset the low modulus of the shield material according to some embodiments of the disclosed technologies.

Figures 19A, 19B:
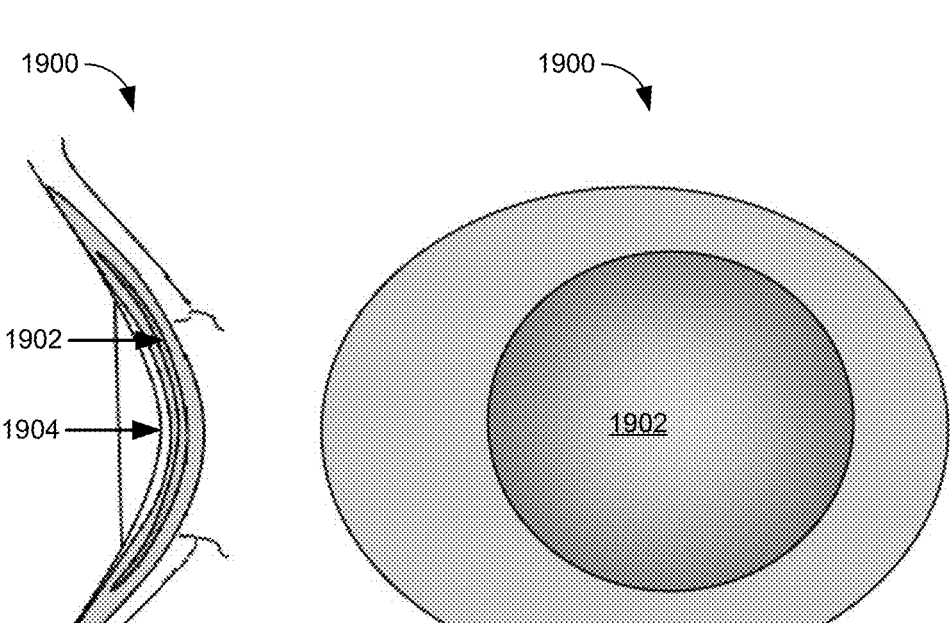
FIGS. 19A,B illustrate an ophthalmic shield having a dome-shaped rigid encapsulated structure to facilitate or maintain a post shield reservoir and to offset the low modulus of the shield material and move the posterior shield surface away from the underlying ocular surface according to some embodiments of the disclosed technologies.

FIG. 19A,B illustrate an ophthalmic shield 1900 having a dome-shaped rigid encapsulated structure 1902 to facilitate or maintain a post shield reservoir 1904 and to offset the low modulus of the shield material and move the posterior shield surface away from the underlying ocular surface according to some embodiments of the disclosed technologies.

Figures 20A, 20B:
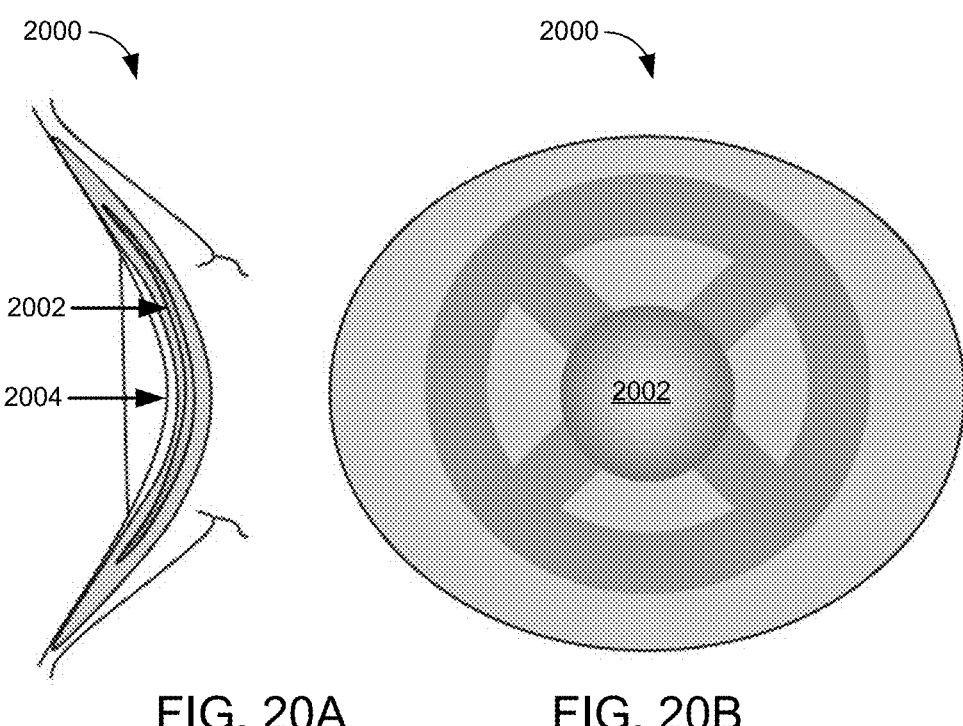
FIGS. 20A,B illustrate an ophthalmic shield having a rigid encapsulated structured scaffold to facilitate a post shield reservoir to offset a low modulus of the shield material and move the posterior shield surface away from the underlying ocular surface according to some embodiments of the disclosed technologies.

FIGS. 20A,B illustrate an ophthalmic shield 2000 having a rigid encapsulated structured scaffold 2002 to facilitate a post shield reservoir 2004 to offset a low modulus of the shield material and move the posterior shield surface away from the underlying ocular surface according to some embodiments of the disclosed technologies.

Figures 21A, 21B:
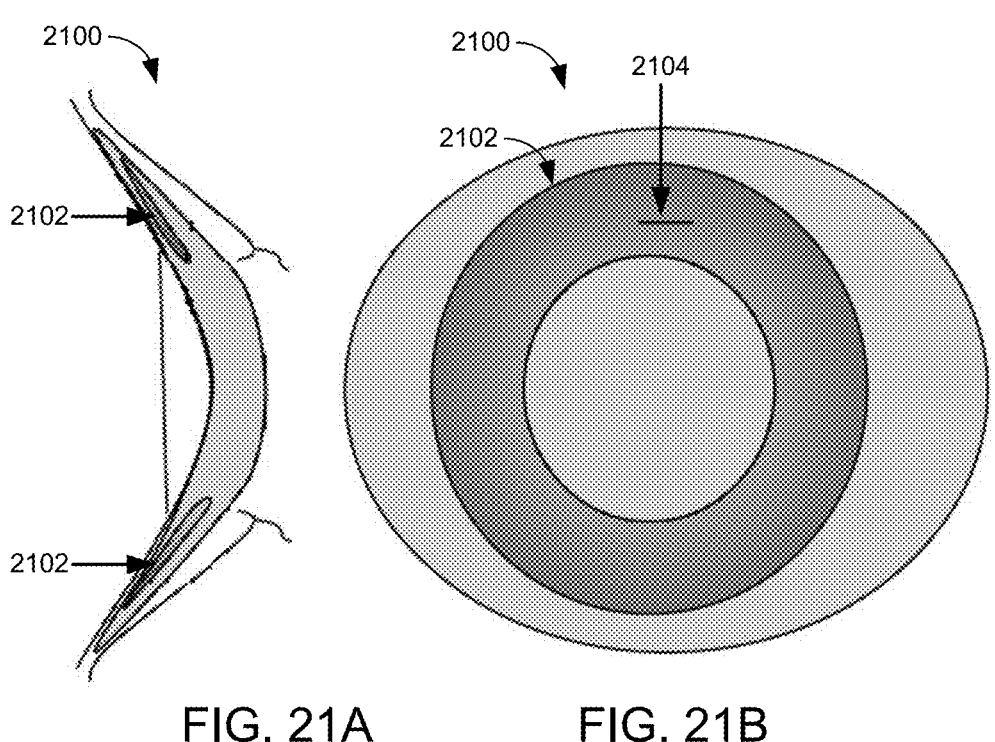
FIGS. 21A,B illustrate an ophthalmic shield with an annular pocket or channel and a port according to some embodiments of the disclosed technologies.

FIGS. 21A,B-30A,B illustrate features and elements of the present invention for delivery of medications to the intra ophthalmic shield space or reservoir. This may be delivered to the eye via diffusion through the shield material or via micro pore structures. There may be multiple spaces or reservoirs, of any size or shape, located at multiple depths within the shield and or multiple points across the shield.

FIGS. 21A,B illustrate an ophthalmic shield 2100 with an annular pocket or channel 2102 and a port 2104 according to some embodiments of the disclosed technologies. The port 2104 may be used to inject materials into the pocket 2102. The port 210 may have a Z-shaped profile or similar profile for closure. The ophthalmic shield 2100 may or may not have a space between the shield and the eye.

Figures 22A, 22B:
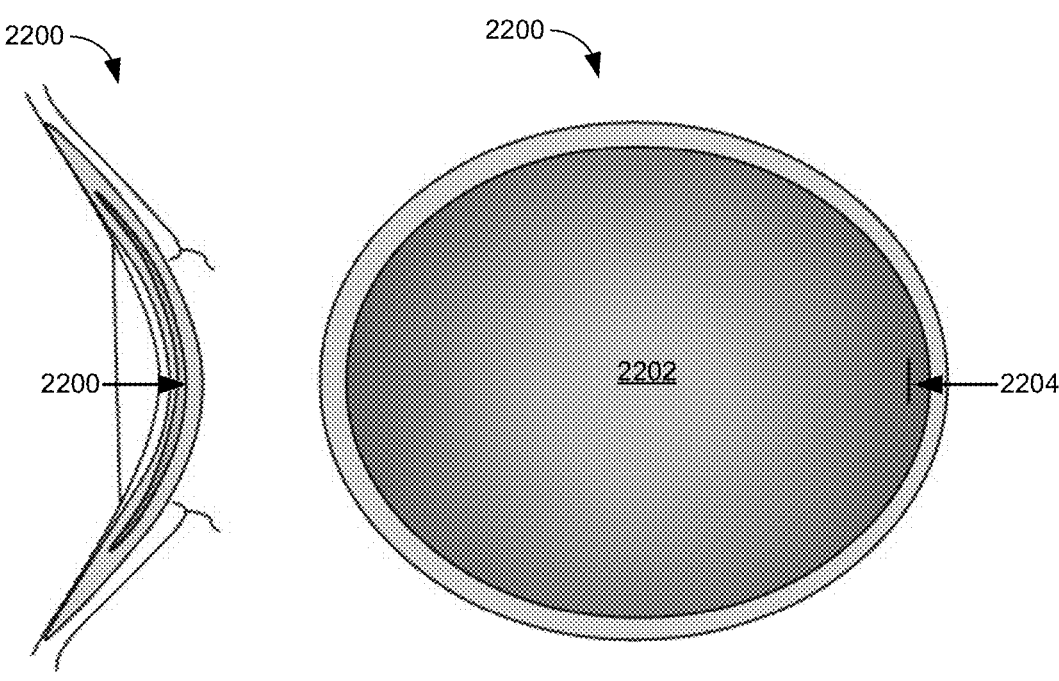
FIGS. 22A,B illustrate an ophthalmic shield with a large disc-shaped pocket and a port according to some embodiments of the disclosed technologies.

FIGS. 22A,B illustrate an ophthalmic shield 2200 with a large disc-shaped pocket 2202 and a port 2204 according to some embodiments of the disclosed technologies. The port 2204 may be similar to the port 2104 of FIG. 21. The ophthalmic shield 2200 may or may not have a space between the shield and the eye.

Figures 23A, 23B:
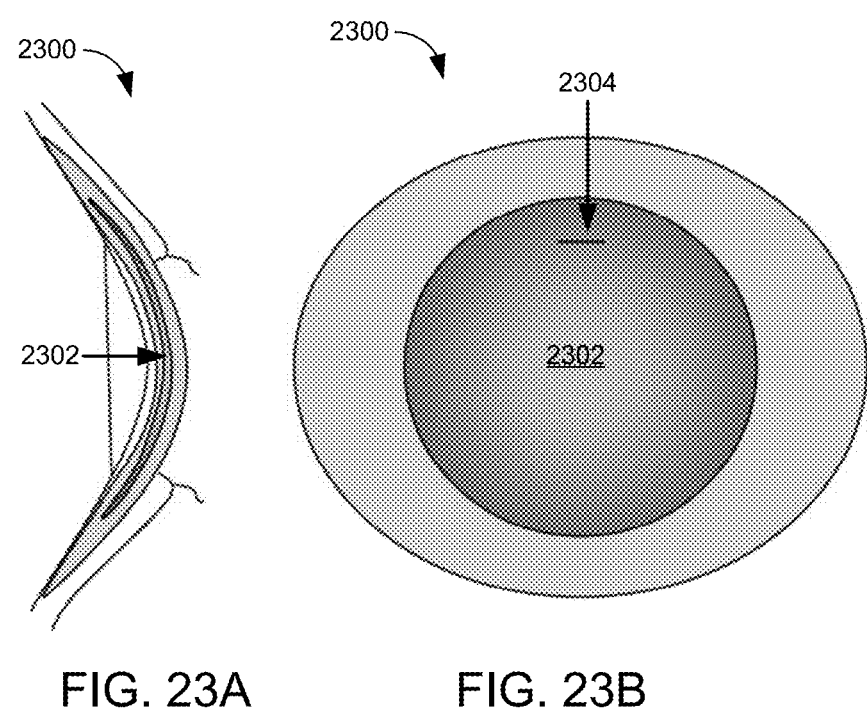
FIGS. 23A,B illustrate an ophthalmic shield with a small disc-shaped pocket and a port according to some embodiments of the disclosed technologies.

FIGS. 23A,B illustrate an ophthalmic shield 2300 with a small disc-shaped pocket 2302 and a port 2304 according to some embodiments of the disclosed technologies. The small disc-shaped pocket 2302 may be sized and located for treatment of the cornea only. The port 2304 may be similar to the port 2104 of FIG. 21. The ophthalmic shield 2300 may or may not have a space between the shield and the eye.

Figures 24A, 24B:
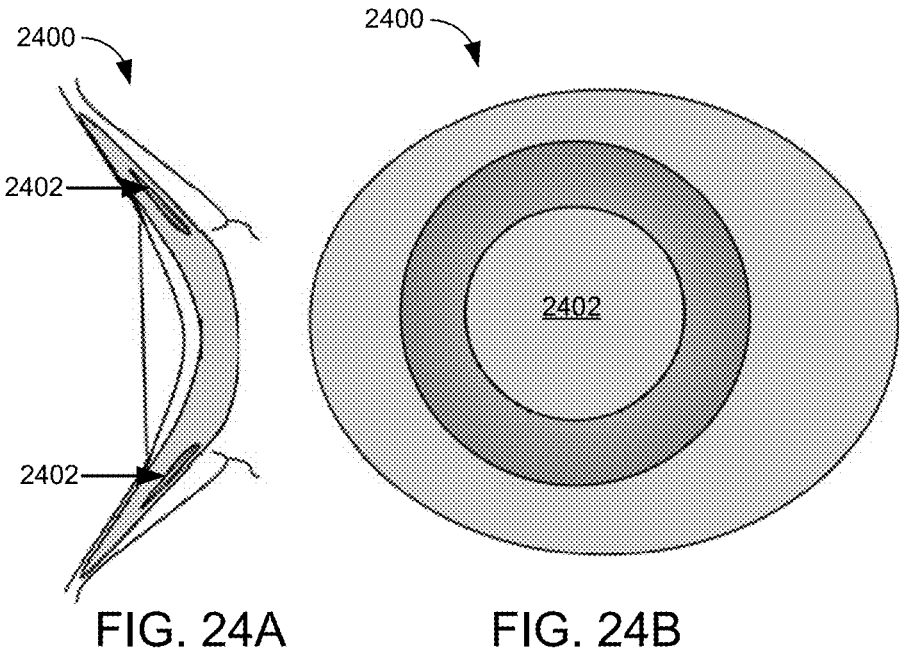
FIGS. 24A,B illustrate an ophthalmic shield with an annular pocket, and without a port, for injection fillings according to some embodiments of the disclosed technologies.

FIGS. 24A,B illustrate an ophthalmic shield 2400 with an annular pocket 2402, and without a port, for injection fillings according to some embodiments of the disclosed technologies. The ophthalmic shield 2400 may or may not have a space between the shield and the eye.

Figures 25A, 25B:
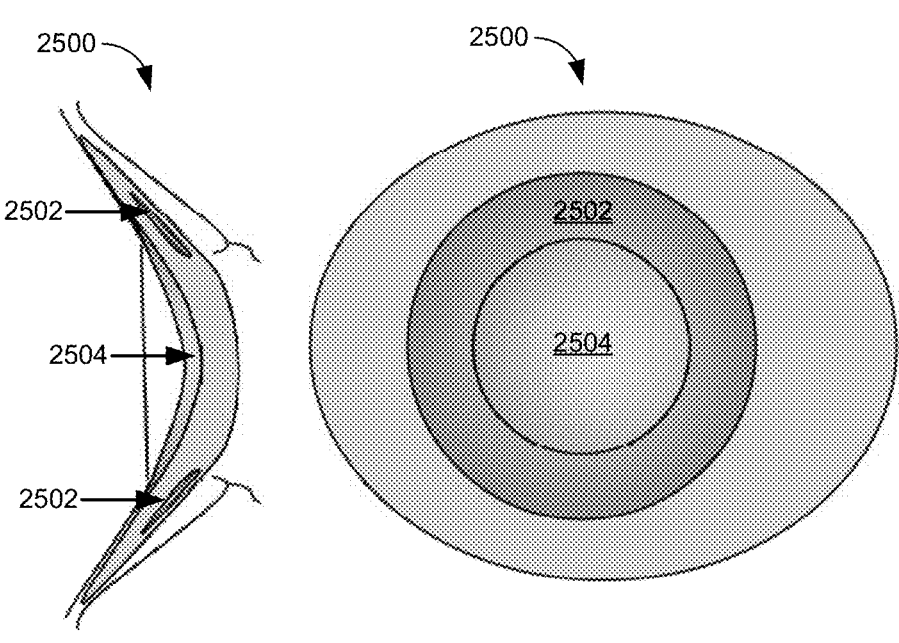
FIGS. 25A,B illustrate an ophthalmic shield having a posterior surface sponge like material and an annular embedded rigid structure to maintain the shape of the sponge space according to some embodiments of the disclosed technologies.

FIGS. 25A,B illustrate an ophthalmic shield 2500 having a posterior surface sponge like material 2504 and an annular embedded rigid 2502 structure to maintain the shape of the 2504 sponge space according to some embodiments of the disclosed technologies. This annulus can instead be a pocket for medication retention as shown in FIG. 24.

Figures 26A, 26B:
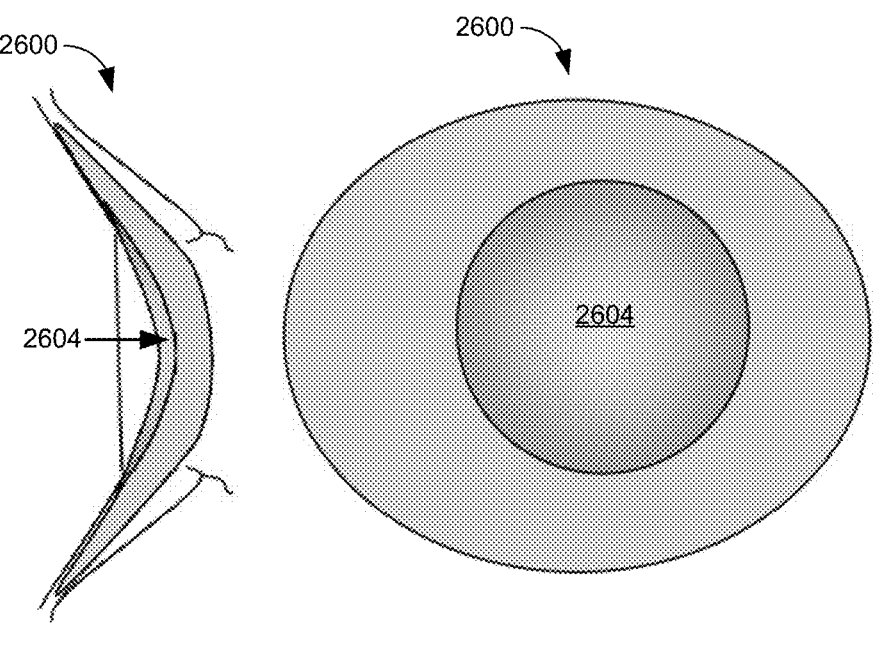
FIGS. 26A,B illustrate an ophthalmic shield with a small posterior surface sponge like material for contacting the cornea only according to some embodiments of the disclosed technologies.

FIGS. 26A,B illustrate an ophthalmic shield 2600 with a small posterior surface sponge like material 2604 for contacting the cornea only according to some embodiments of the disclosed technologies.

Figures 27A, 27B:
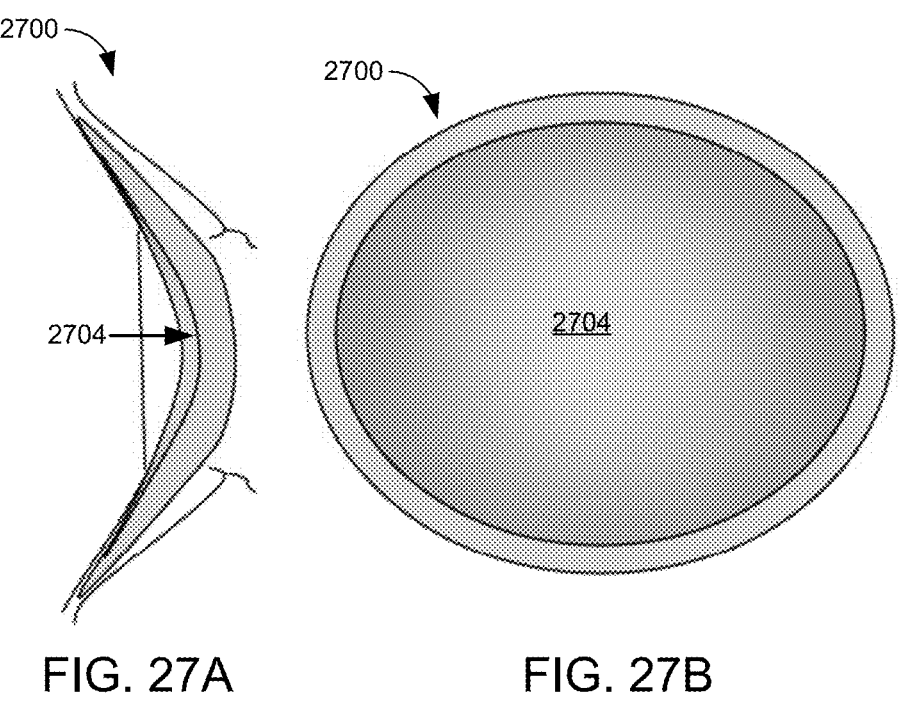
FIGS. 27A,B illustrate an ophthalmic shield a large posterior surface sponge like material for contacting the full ocular surface according to some embodiments of the disclosed technologies.

FIGS. 27A,B illustrate an ophthalmic shield 2700 a large posterior surface sponge like material 2704 for contacting the full ocular surface according to some embodiments of the disclosed technologies.

Figures 28A, 28B:
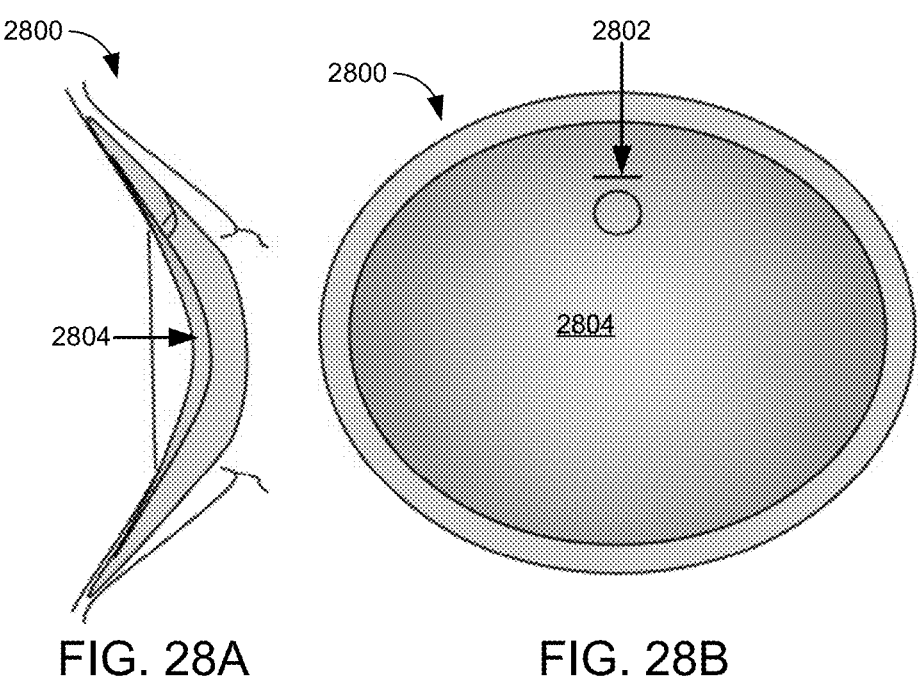
FIGS. 28A,B illustrate an ophthalmic shield a large posterior surface sponge like material, and a port to pass materials to the sponge like material according to some embodiments of the disclosed technologies.

FIGS. 28A,B illustrate an ophthalmic shield 2800 a large posterior surface sponge like material 2804, and a port 2802 to pass materials to the sponge like material 2804 according to some embodiments of the disclosed technologies.

Figures 29A, 29B:
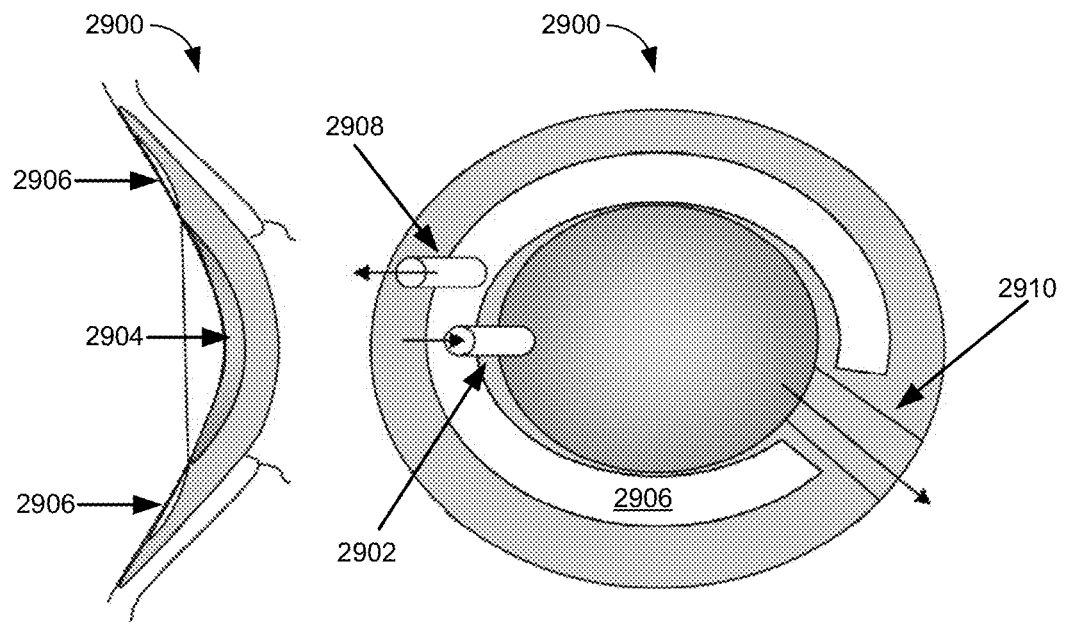
FIGS. 29A,B illustrate an ophthalmic shield with a small posterior surface sponge like material, a port to pass materials to the sponge like material, a docking channel and suction port to dock the ophthalmic shield with the eye, and a drain to manage fluids according to some embodiments of the disclosed technologies.

FIGS. 29A,B illustrate an ophthalmic shield 2900 with a small posterior surface sponge like material 2904, a port 2902 to pass materials to the sponge like material 2904, a docking channel 2906 and suction port 2908 to dock the ophthalmic shield 2900 with the eye, and a drain 2910 to manage fluids according to some embodiments of the disclosed technologies.

Figures 30A, 30B:
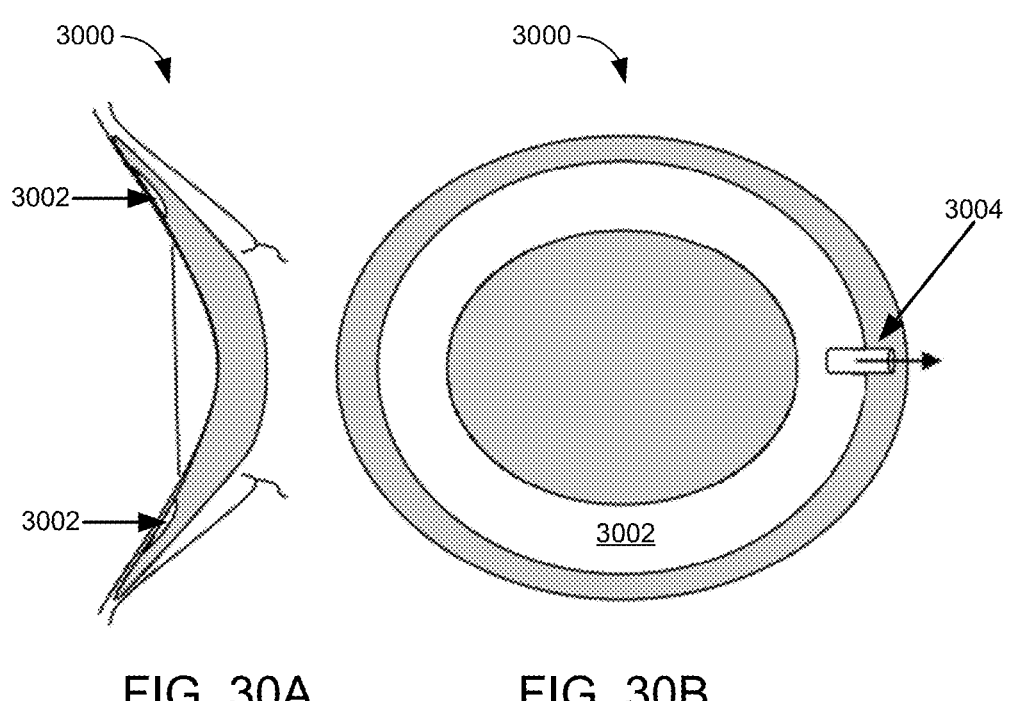
FIGS. 30A,B illustrate an ophthalmic shield with a docking channel and suction port to dock the ophthalmic shield with the eye according to some embodiments of the disclosed technologies.

FIGS. 30A,B-33A,B illustrate ophthalmic shields having a channel with a port for creating suction to anchor the ophthalmic shield to the ocular surface.

FIGS. 30A,B illustrate an ophthalmic shield 3000 with a docking channel 3002 and suction port 3004 to dock the ophthalmic shield 3000 with the eye according to some embodiments of the disclosed technologies.

Figures 31A, 31B:
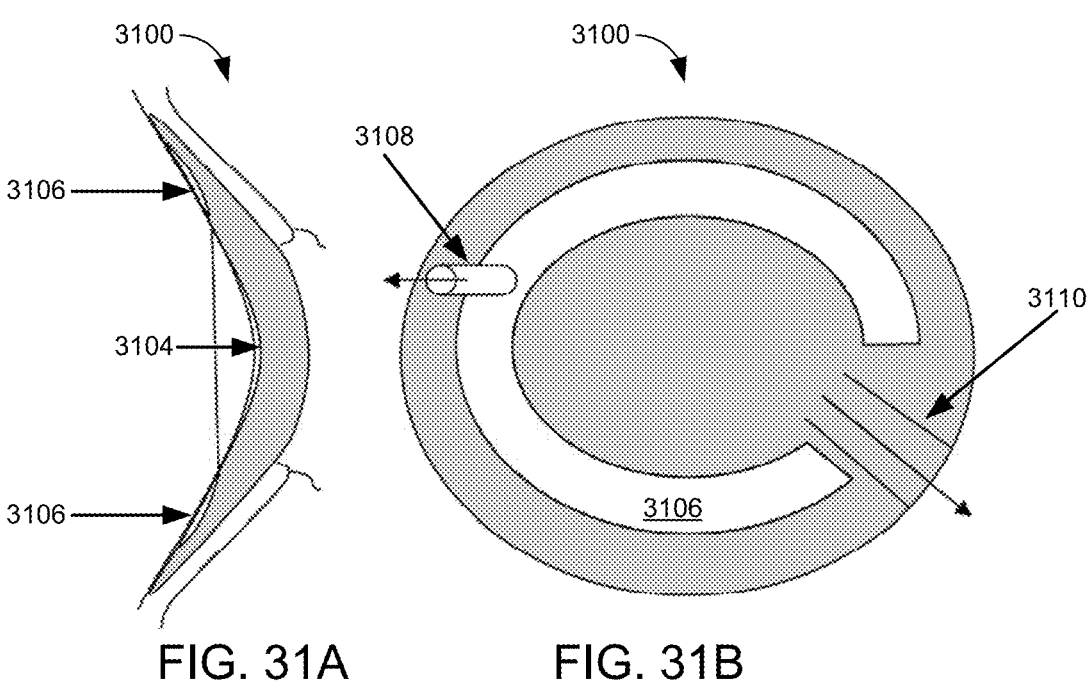
FIGS. 31A,B illustrate an ophthalmic shield with a posterior space between the ophthalmic shield and the eye, with a docking channel and suction port to dock the ophthalmic shield with the eye, and with a passive drain to manage fluids according to some embodiments of the disclosed technologies.

FIGS. 31A,B illustrate an ophthalmic shield 3100 with a posterior space 3104 between the ophthalmic shield 3100 and the eye, with a docking channel 3106 and suction port 3108 to dock the ophthalmic shield 3100 with the eye, and with a passive drain 3110 to manage fluids according to some embodiments of the disclosed technologies.

Figures 32A, 32B:
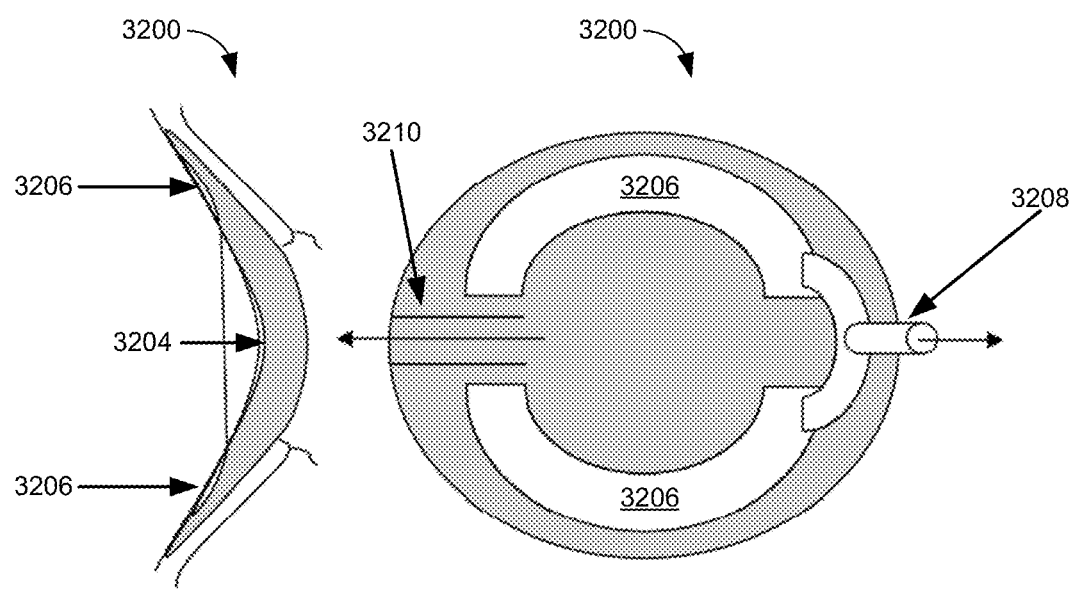
FIGS. 32A,B illustrate an ophthalmic shield with a posterior space between the ophthalmic shield and the eye, with multiple docking channels and suction port to dock the ophthalmic shield with the eye, and with a drain to manage fluids according to some embodiments of the disclosed technologies.

FIGS. 32A,B illustrate an ophthalmic shield 3200 with a posterior space 3204 between the ophthalmic shield 3200 and the eye, with multiple docking channels 3206 and suction port 3208 to dock the ophthalmic shield 3200 with the eye, and with a drain 3210 to manage fluids according to some embodiments of the disclosed technologies.

Figures 33A, 33B:
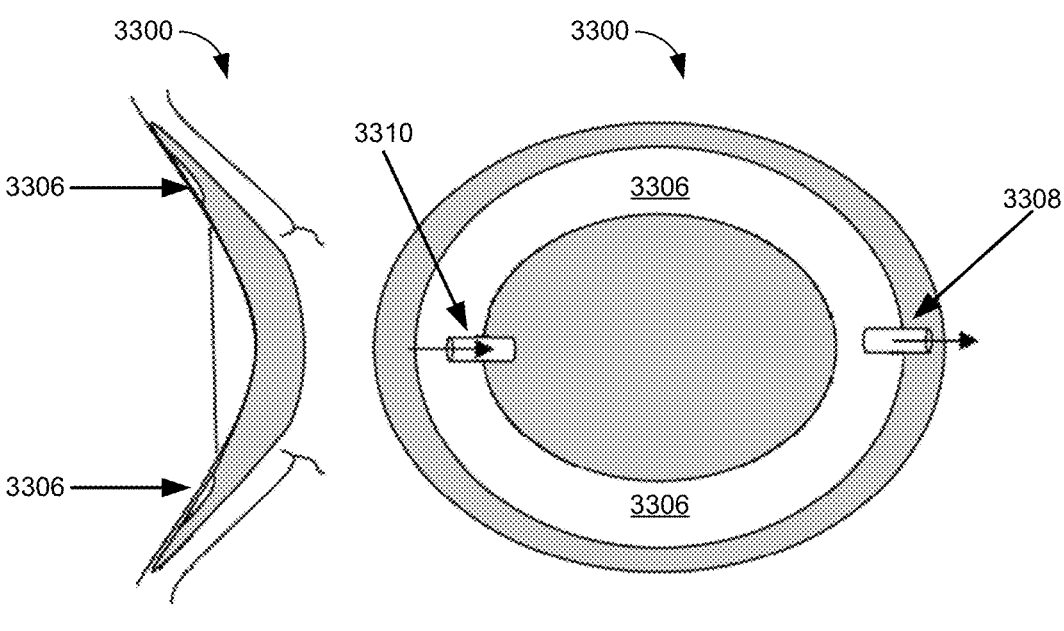
FIGS. 33A,B illustrate an ophthalmic shield with an inlet to position the ophthalmic shield on the eye, and with a docking channel and suction port to dock the ophthalmic shield with the eye according to some embodiments of the disclosed technologies.

FIGS. 33A,B illustrate an ophthalmic shield 3300 with an inlet 3310 to position the ophthalmic shield 3300 on the eye, and with a docking channel 3306 and suction port 3308 to dock the ophthalmic shield 3300 with the eye according to some embodiments of the disclosed technologies.

Figures 34A, 34B:
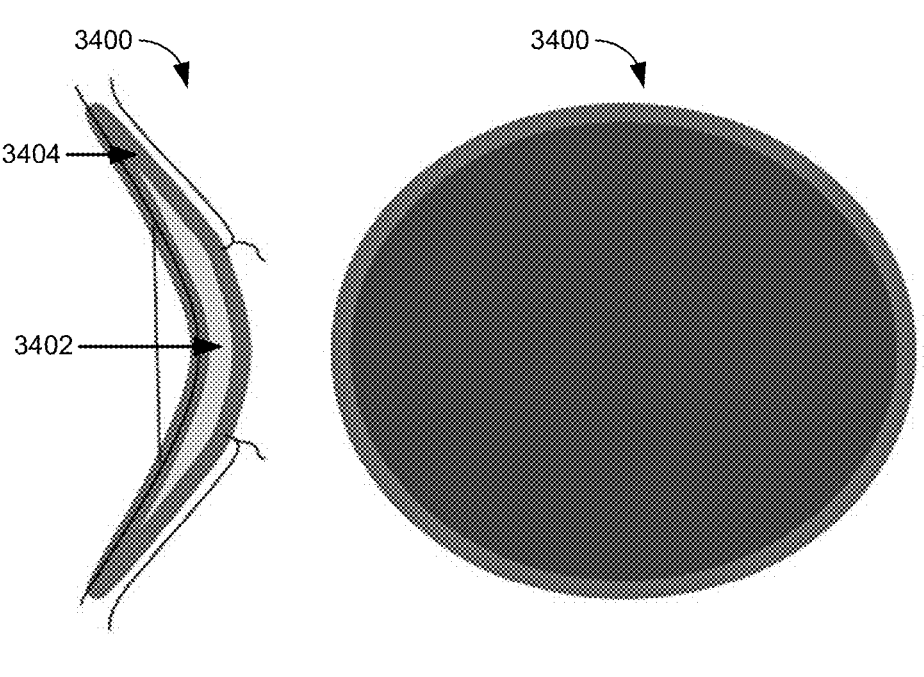
FIGS. 34A,B illustrate an ophthalmic shield having a core that is encapsulated in one or more therapeutic or treatment materials according to some embodiments of the disclosed technologies.

FIGS. 34A,B illustrate an ophthalmic shield 3400 having a core 3402 that is encapsulated in one or more therapeutic or treatment materials 3404 according to some embodiments of the disclosed technologies. The treatment materials 3404 may include amnion, biologics, other cells, regenerative medicine, tissue, gels, liquids, and similar materials.

Figures 35A, 35B:
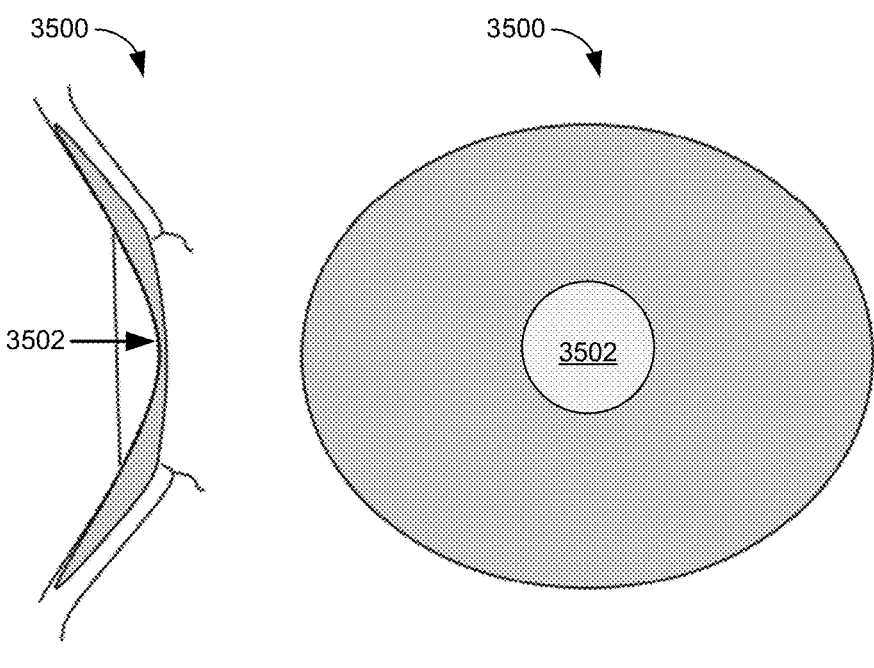
FIGS. 35A,B illustrate an ophthalmic shield with a thinner central section 3502 for greater transmissibility to oxygen and water vapor according to some embodiments of the disclosed technologies.

FIGS. 35A,B-37A,B illustrate ophthalmic shields to facilitate osmotic intervention for treatment of corneal edema.

FIGS. 35A,B illustrate an ophthalmic shield 3500 with a thinner central section 3502 for greater transmissibility to oxygen and water vapor according to some embodiments of the disclosed technologies. The thin region will have higher water vapor transmissibility to draw water vapor from an underlying edematous corneal region. The location of the thin zone for managing corneal edema may be modulated to conform to the edematous region of the cornea. In some embodiments, the ophthalmic shield 3500 may create osmolarity differentials in selected areas having greater or lesser thicknesses. In some embodiments, the ophthalmic shield 3500 may be guided by tomography, and may include surface registration dots. These features allow mapping areas of the cornea which are most prone to swelling, for example using corneal thickness difference maps, to create corresponding thin gradients to manage the swelling.

Figures 36A, 36B:
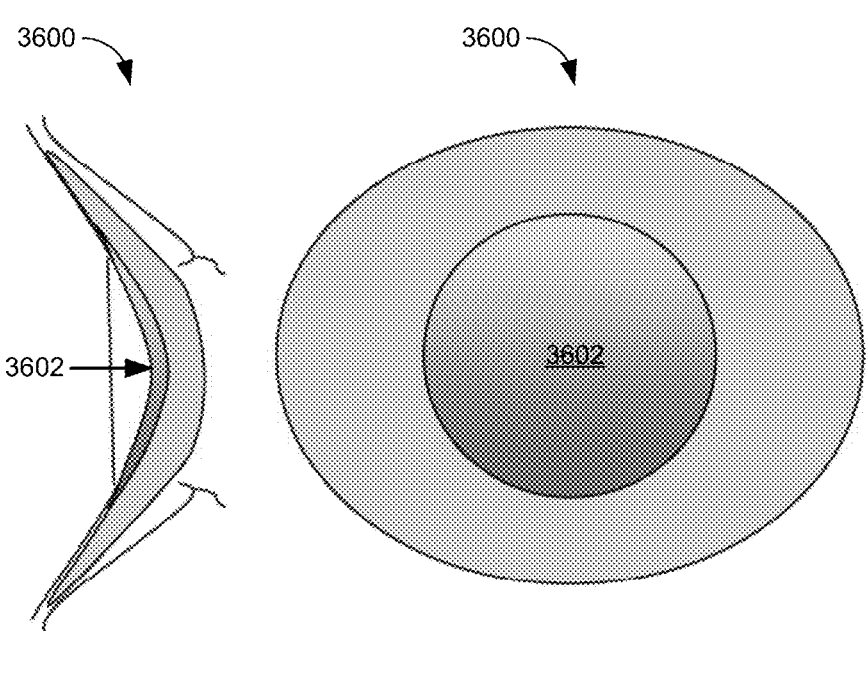
FIGS. 36A,B illustrate an ophthalmic shield with posterior hydrophilic materials or hypertonic materials to create osmotic flux according to some embodiments of the disclosed technologies.

FIGS. 36A,B illustrate an ophthalmic shield 3600 with posterior hydrophilic materials or hypertonic materials 3602 to create osmotic flux according to some embodiments of the disclosed technologies.

Figures 37A, 37B:
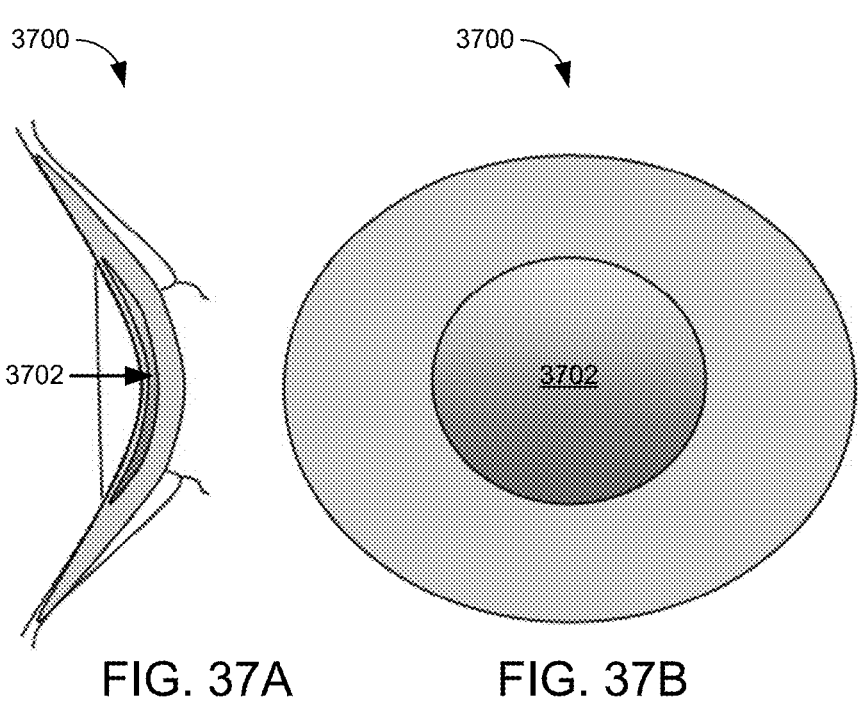
FIGS. 37A,B illustrate an ophthalmic shield with encapsulated hydrophilic materials or hypertonic materials to create osmotic flux according to some embodiments of the disclosed technologies.

FIGS. 37A,B illustrate an ophthalmic shield 3700 with encapsulated hydrophilic materials or hypertonic materials 3702 to create osmotic flux according to some embodiments of the disclosed technologies.

Figures 38A, 38B:
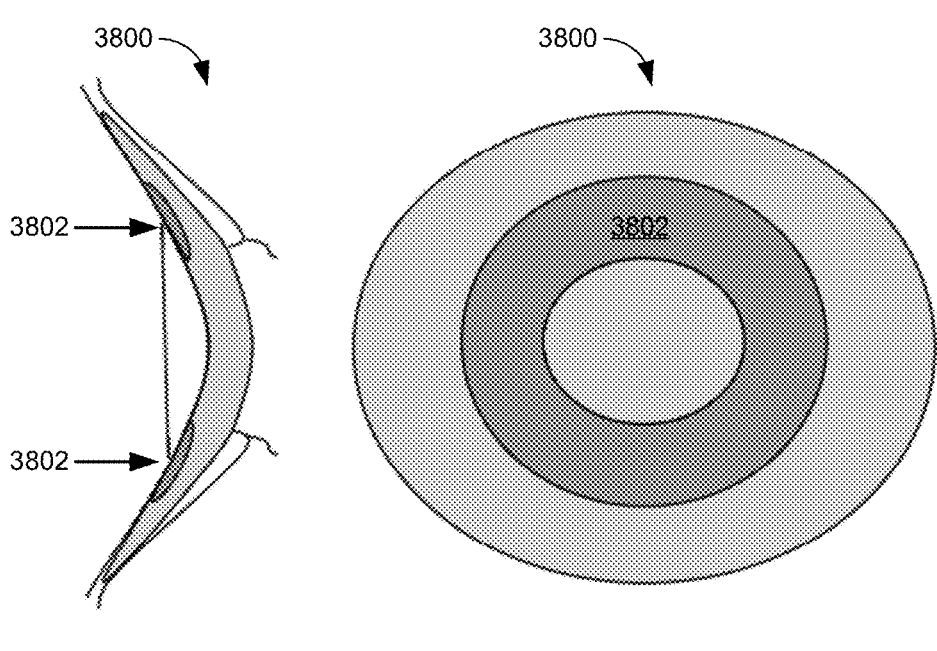
FIGS. 38A,B illustrate an ophthalmic shield for localized stem cell or other biologic delivery to the limbus using a wide limbal tract pattern according to some embodiments of the disclosed technologies.

FIGS. 38A,B illustrate an ophthalmic shield 3800 for localized stem cell or other biologic delivery to the limbus using a wide limbal tract pattern 3802 according to some embodiments of the disclosed technologies.

Figures 39A, 39B:
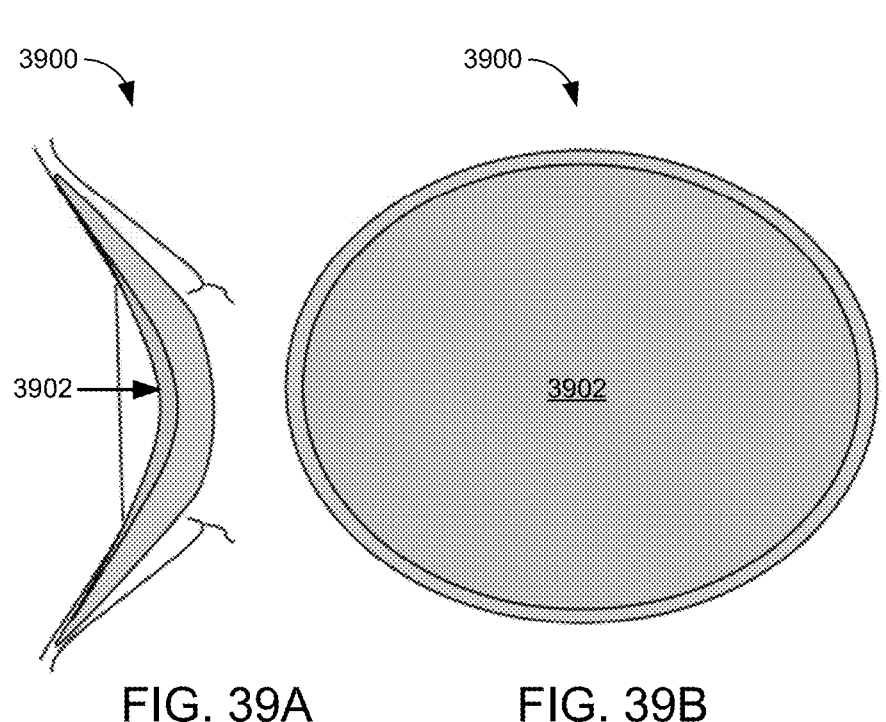
FIGS. 39A,B illustrate an ophthalmic shield for localized stem cell delivery with a full back surface according to some embodiments of the disclosed technologies.

FIGS. 39A,B illustrate an ophthalmic shield 3900 for localized stem cell delivery with a full back surface 3902 according to some embodiments of the disclosed technologies.

Figures 40A, 40B:
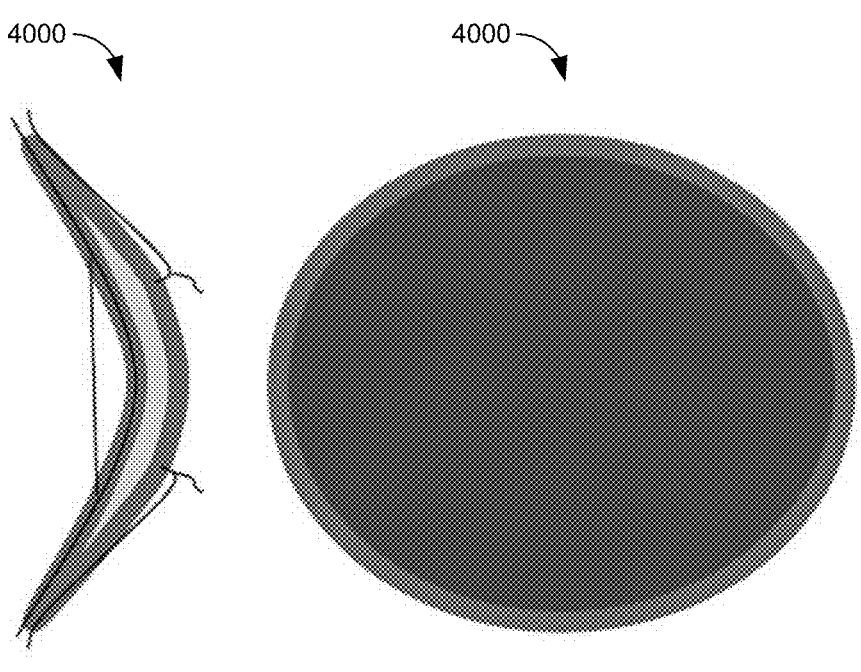
FIGS. 40A,B illustrate an ophthalmic shield having a full encapsulation membrane according to some embodiments of the disclosed technologies.

FIGS. 40A,B-42A,B illustrate ophthalmic shields with a localized amniotic membrane. The amniotic membrane may dissolve and the shield is retained and covers tissue after the membrane dissolves.

FIGS. 40A,B illustrate an ophthalmic shield 4000 having a full encapsulation membrane according to some embodiments of the disclosed technologies.

Figures 41A, 41B:
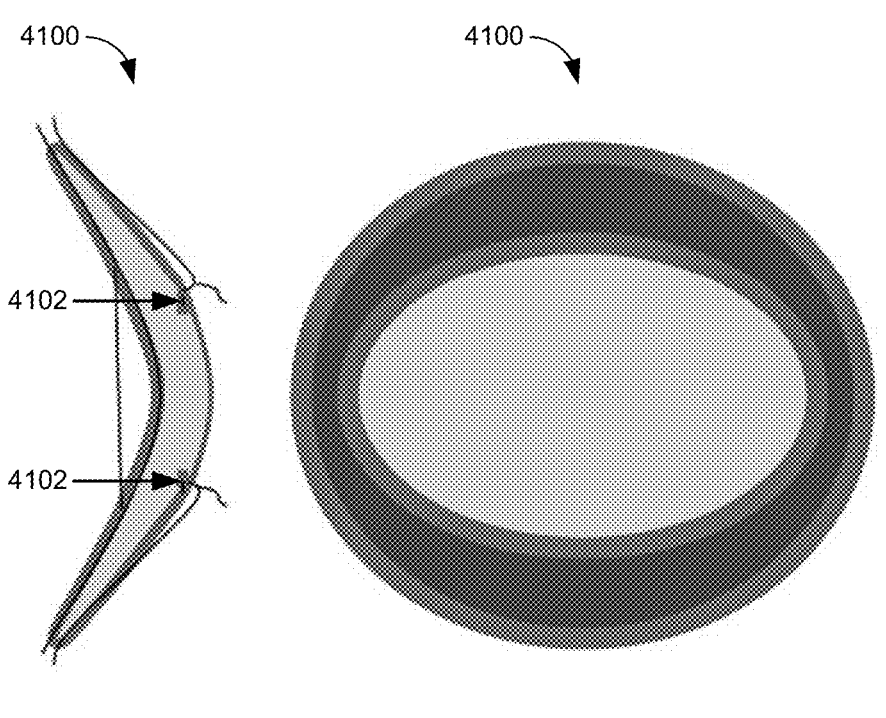
FIGS. 41A,B illustrate an ophthalmic shield having posterior edge encapsulation according to some embodiments of the disclosed technologies.

FIGS. 41A,B and 42A,B illustrate ophthalmic shields 4100 and 4200, respectively, having posterior and front edge encapsulation according to some embodiments of the disclosed technologies. The ophthalmic shields 4100, 4200 may include slits 4102, 4202 for insertion of material. The ophthalmic shield 4100 of FIG. 41 may have a one-piece construction. The ophthalmic shield 4200 of FIG. 42 may have a multi-piece construction where the pieces slide or snap together. Additionally, membranes may be snapped in and have extra overhanging membrane for lid margin application.

FIGS. 43A,B-45A,B illustrate ophthalmic shields with central regions for optical correction of the eye.

FIGS. 43A,B illustrate an ophthalmic shield 4300 having variable thickness to produce a smooth anterior shape according to some embodiments of the disclosed technologies.

Figures 44A, 44B:
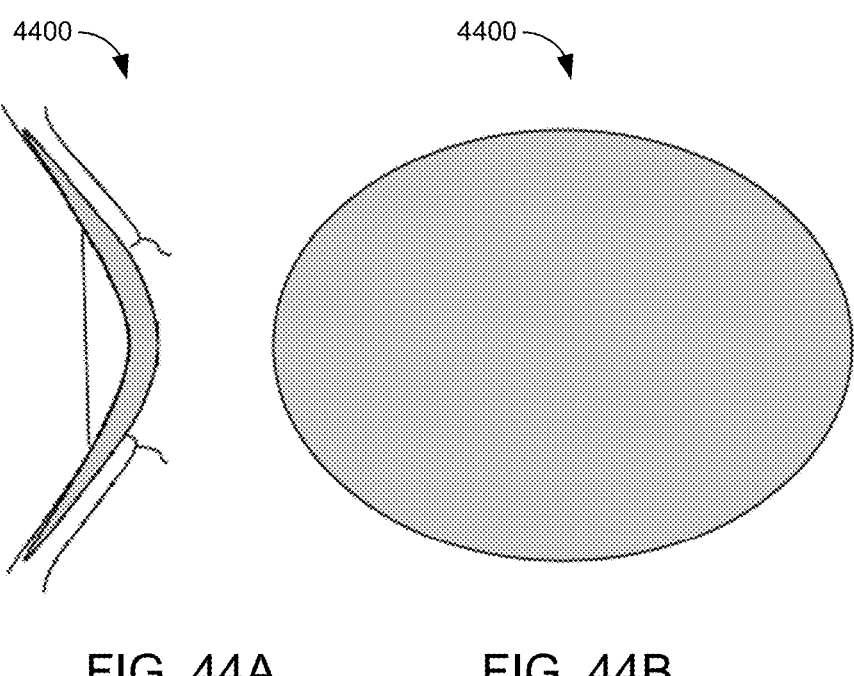
FIGS. 44A,B illustrate an ophthalmic shield having a normal thickness according to some embodiments of the disclosed technologies.

FIGS. 44A,B illustrate an ophthalmic shield 4400 having a normal thickness according to some embodiments of the disclosed technologies.

Figures 45A, 45B:
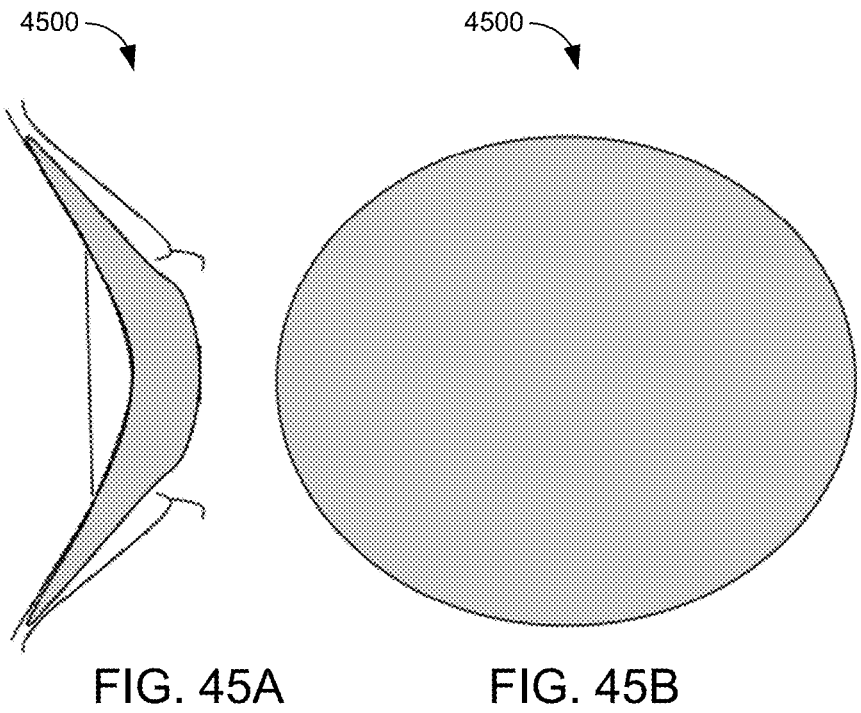
FIGS. 45A,B illustrate an ophthalmic shield having increased thickness only over the cornea according to some embodiments of the disclosed technologies.

FIGS. 45A,B illustrate an ophthalmic shield 4500 having increased thickness only over the cornea according to some embodiments of the disclosed technologies.

Figures 46A, 46B:
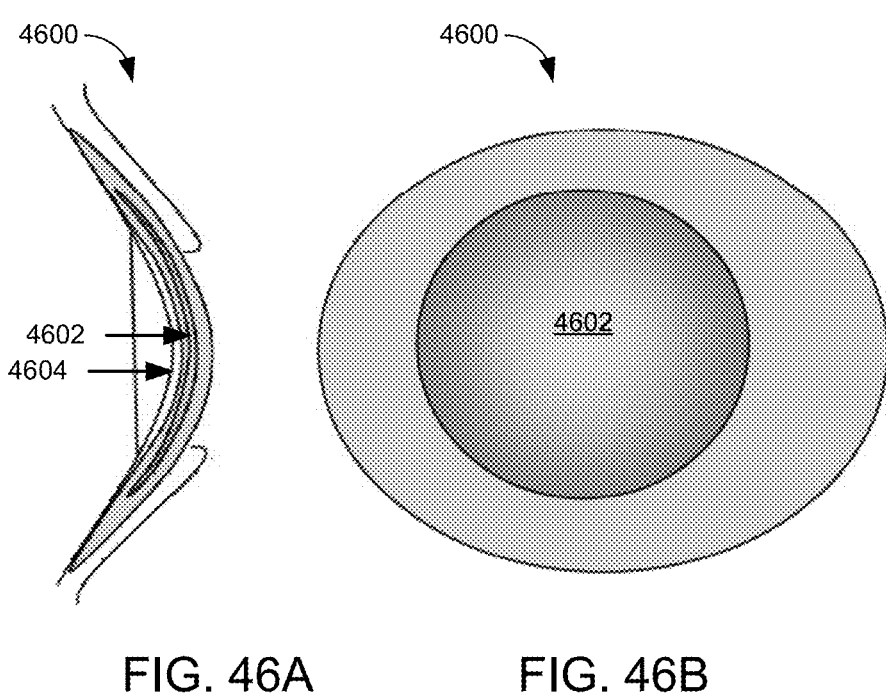
FIGS. 46A,B illustrate an ophthalmic shield with encapsulated optical material inside the region of the underlying cornea-scleral junction and extending outside the cornea-scleral junction according to some embodiments of the disclosed technologies.

FIGS. 46A,B illustrate an ophthalmic shield with encapsulated optical material 4602 inside the region of the underlying cornea-scleral junction and extending outside the cornea-scleral junction according to some embodiments of the disclosed technologies. The encapsulated optical material 4602 may be rigid, forming a space 4604 between the ophthalmic shield 4600 and the eye. Here it should be noted that any of the embodiments disclosed herein may feature such a space, or may rest directly on the ocular surface.

Figures 47A, 47B:
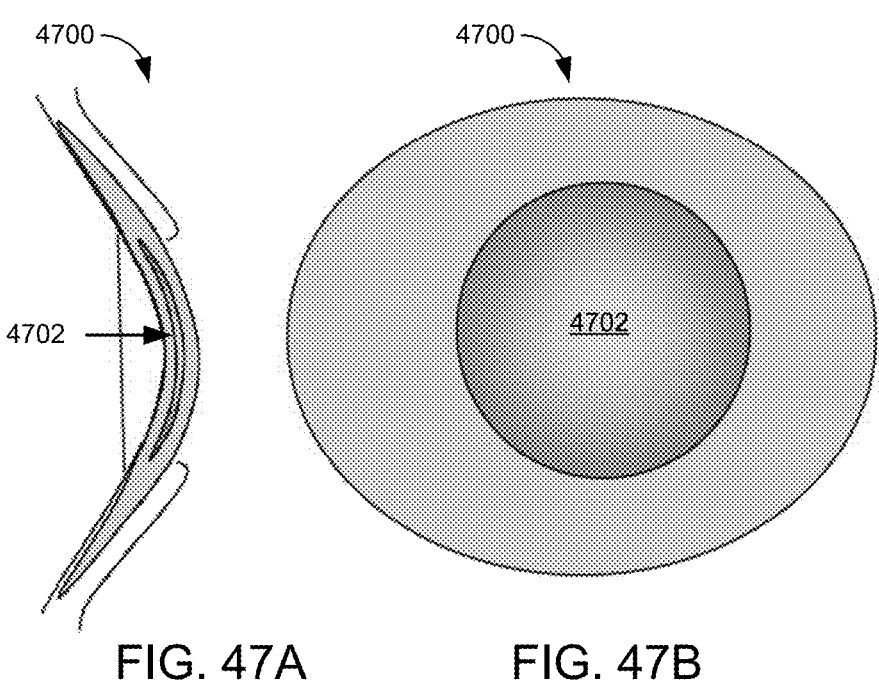
FIGS. 47A,B illustrate an ophthalmic shield with encapsulated optical material inside the region of the underlying cornea-scleral junction and not extending outside the cornea-scleral junction according to some embodiments of the disclosed technologies.

FIGS. 47A,B illustrate an ophthalmic shield with encapsulated optical material 4702 inside the region of the underlying cornea-scleral junction and not extending outside the cornea-scleral junction according to some embodiments of the disclosed technologies.

Figures 48A, 48B:
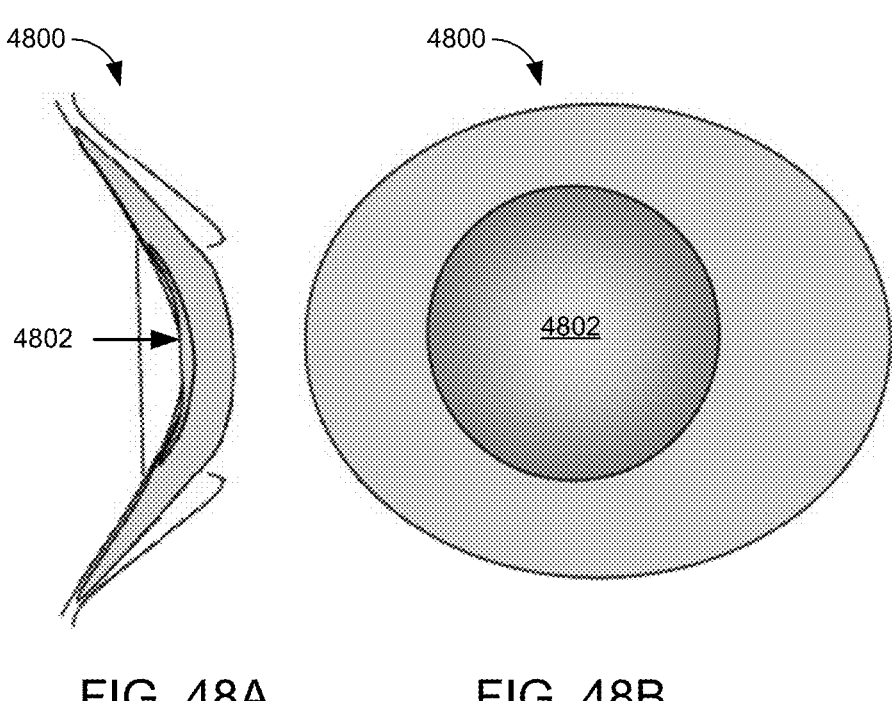
FIGS. 48A,B illustrate an ophthalmic shield with a rigid back surface for optical correction of the eye with posterior surface geometry for reshaping the curvature of the cornea according to some embodiments of the disclosed technologies.

FIGS. 48A,B illustrate an ophthalmic shield 4800 with a rigid back surface 4802 for optical correction of the eye with posterior surface geometry for reshaping the curvature of the cornea according to some embodiments of the disclosed technologies.

Figures 49A, 49B:
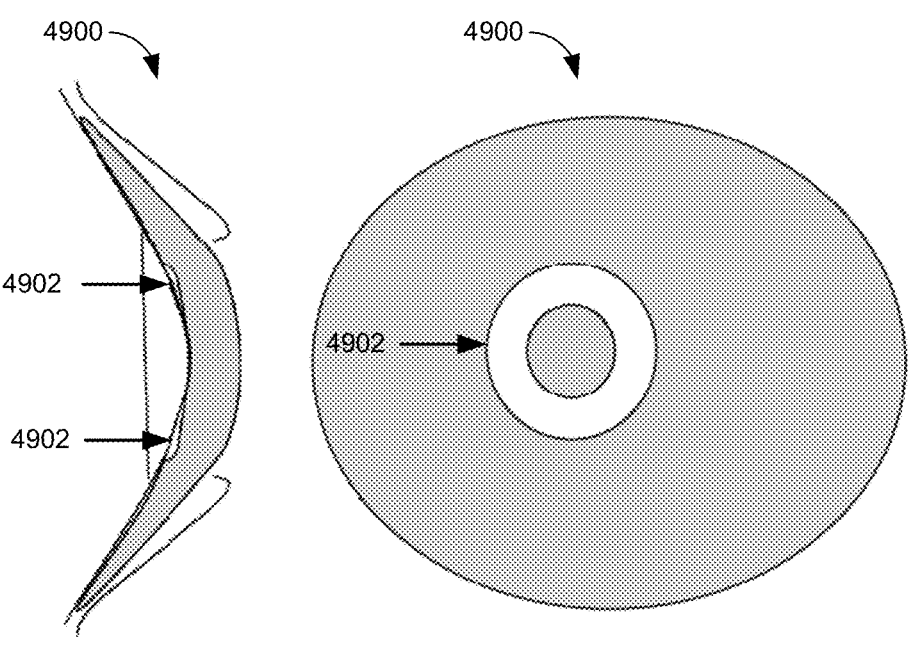
FIG. 49A,B illustrates an ophthalmic shield with posterior surface geometry for reshaping the curvature of the cornea according to some embodiments of the disclosed technologies.

FIG. 49A,B illustrates an ophthalmic shield 4900 with posterior surface geometry 4902 for reshaping the curvature of the cornea according to some embodiments of the disclosed technologies.

Figures 50A, 50B:
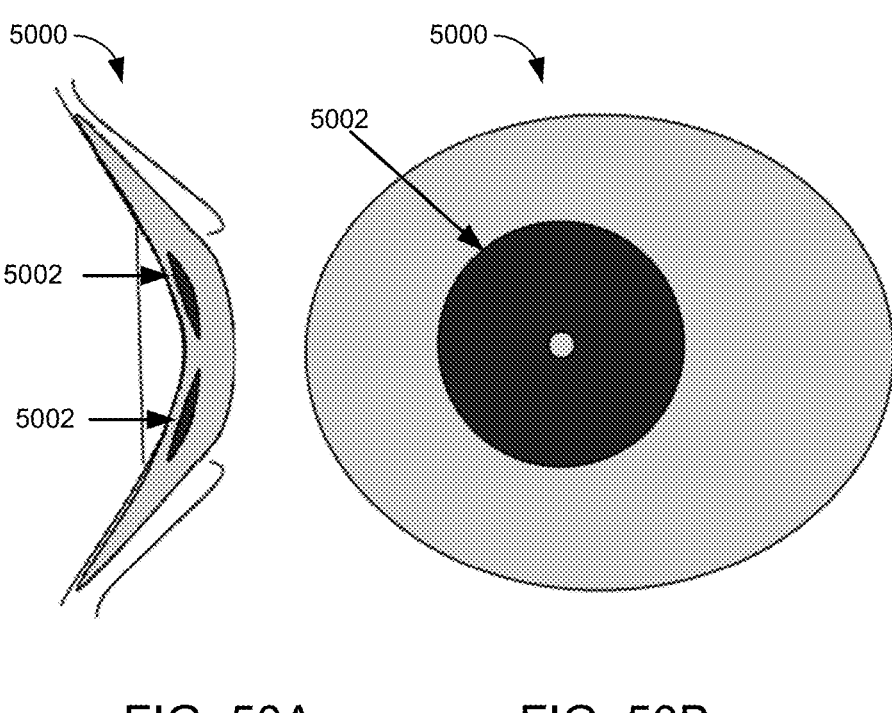
FIG. 50A,B illustrates an ophthalmic shield with an encapsulated pinhole aperture in a rigid or flexible opaque secondary material according to some embodiments of the disclosed technologies.

FIG. 50A,B illustrates an ophthalmic shield 5000 with an encapsulated pinhole aperture in a rigid or flexible opaque secondary material 5002 according to some embodiments of the disclosed technologies.

Figures 51A, 51B:
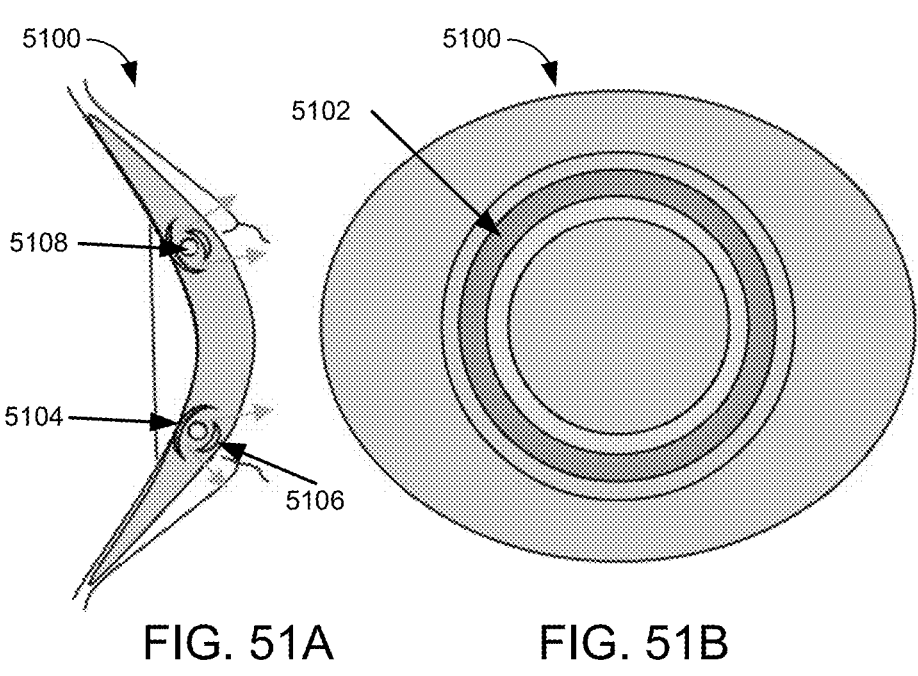
FIGS. 51A,B illustrate an ophthalmic shield with a backlit light ring for directional lighting according to some embodiments of the disclosed technologies.

FIGS. 51A,B-54A,B illustrate ophthalmic shields with features for cosmetic alteration of the appearance of the eye.

FIGS. 51A,B illustrate an ophthalmic shield 5100 with a backlit light ring 5102 for directional lighting according to some embodiments of the disclosed technologies. The light ring 5102 may include a light source 5108, a reflective material 5104, and a refractive material 5106, for example as shown in FIG. 51A. It may also include a sensor to dim or stop illumination during blinks or closed eyes and may be controlled by an external source.

Figures 52A, 52B:
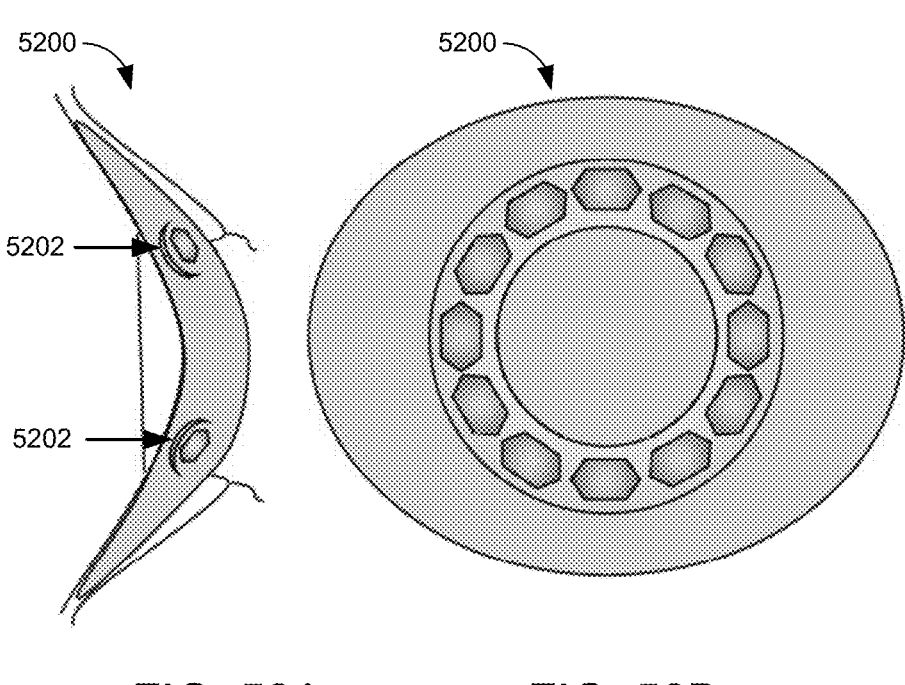
FIGS. 52A,B illustrate an ophthalmic shield with precious metals and/or stones 5202 according to some embodiments of the disclosed technologies.

FIGS. 52A,B illustrate an ophthalmic shield 5200 with precious metals and/or stones 5202 according to some embodiments of the disclosed technologies.

Figures 53A, 53B:
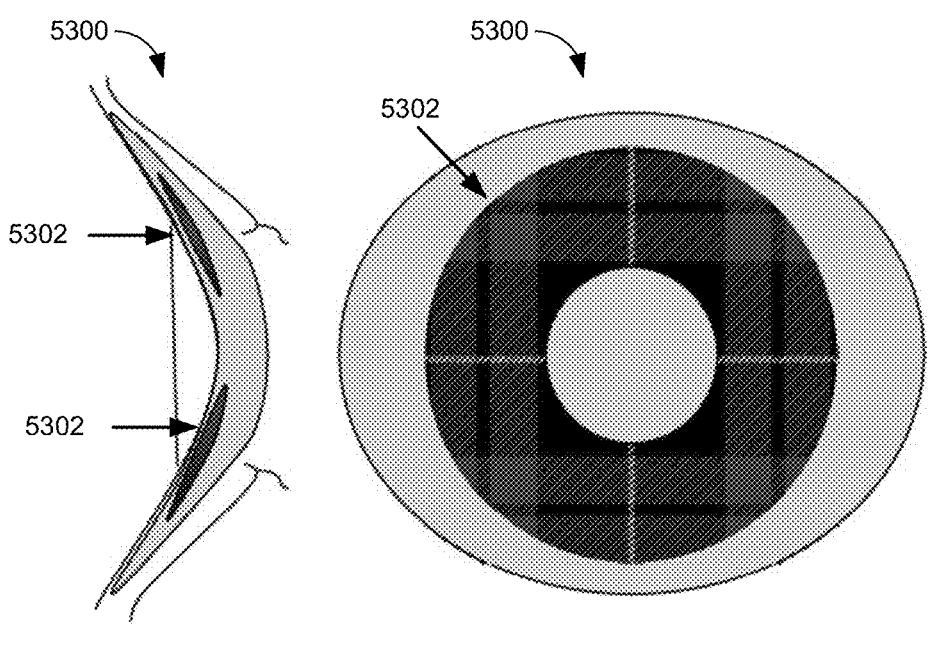
FIGS. 53A,B illustrate an ophthalmic shield with encapsulated fabric, material, print or patterns according to some embodiments of the disclosed technologies.

FIGS. 53A,B illustrate an ophthalmic shield 5300 with encapsulated fabric, material, print or patterns 5302 according to some embodiments of the disclosed technologies. These features may take any shape, and may be disposed in any position within the shield 5300.

Figures 54A, 54B:
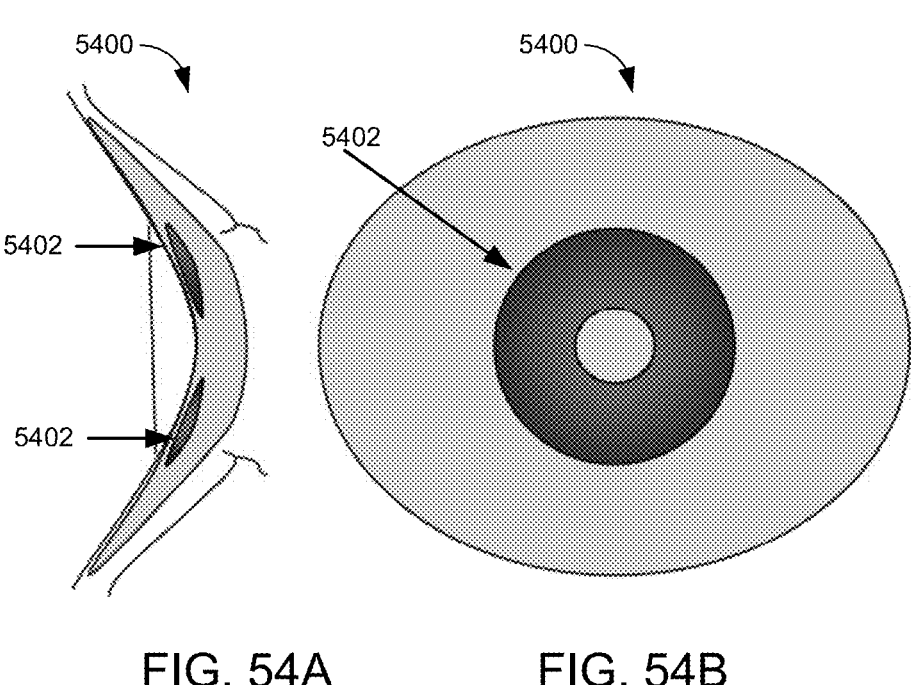
FIGS. 54A,B illustrate an ophthalmic shield with an encapsulated iris feature according to some embodiments of the disclosed technologies.

FIGS. 54A,B illustrate an ophthalmic shield 5400 with an encapsulated iris feature 5402 according to some embodiments of the disclosed technologies. The feature 5402 may be 3D printed, a LaserJet printed disk, a hand-painted disk, photo wafer, fabric, or similar materials. A deep positioning of the iris in the shield 5400 may create a more natural appearance of depth. The thickness may be altered to create a similar effect.

Figures 55A, 55B:
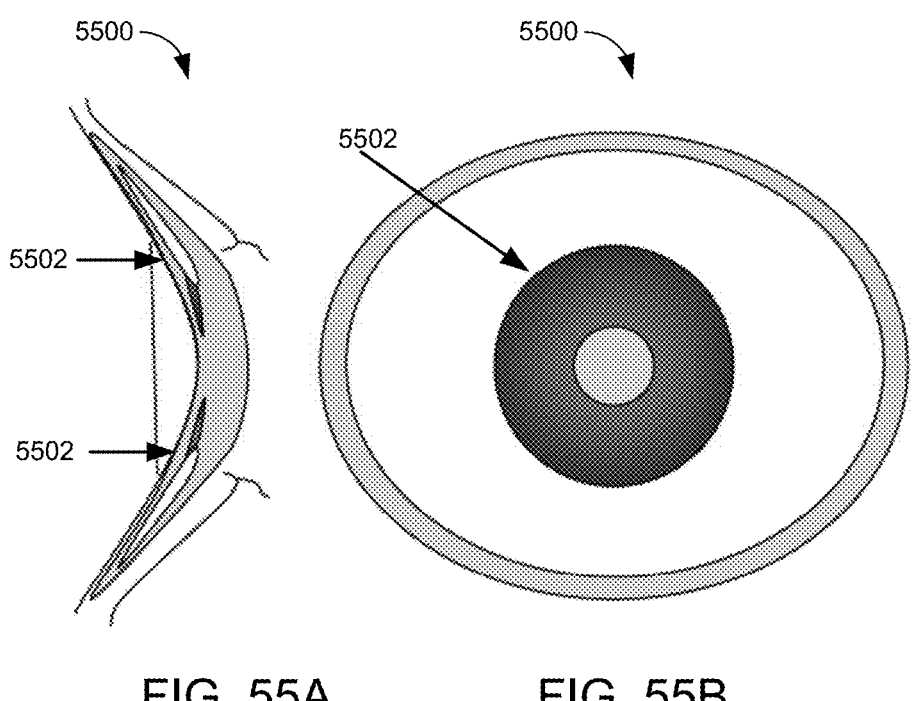
FIGS. 55A,B illustrate an ophthalmic shield with an encapsulated iris and scleral feature according to some embodiments of the disclosed technologies.

FIGS. 55A,B illustrate an ophthalmic shield 5500 with an encapsulated iris and scleral feature 5502 according to some embodiments of the disclosed technologies. The feature 5502 may be ocular surface 3D printed, a LaserJet printed disk, a hand-painted disk, fabric, or similar materials.

Figures 56A, 56B:
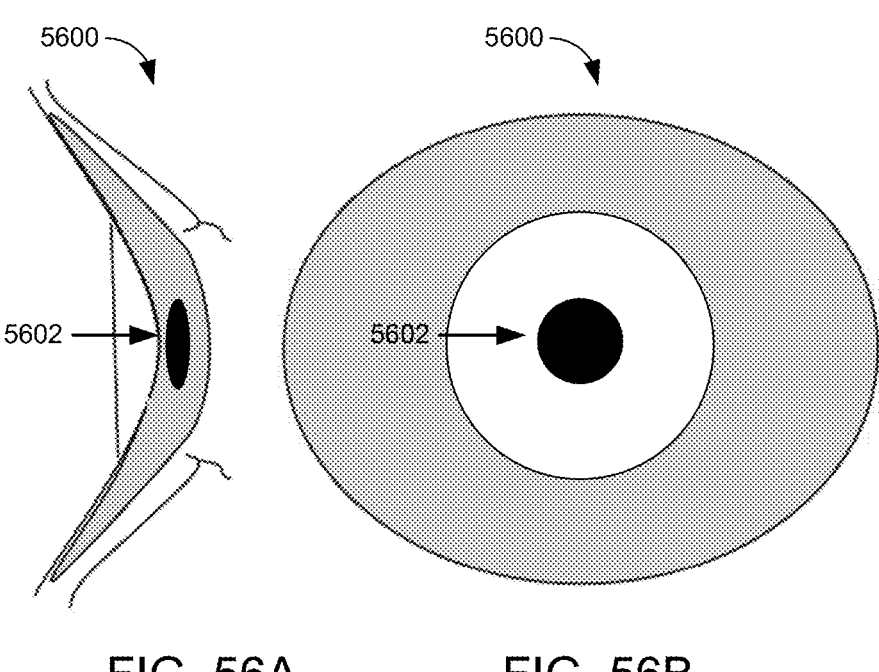
FIGS. 56A,B illustrate an ophthalmic shield with an encapsulated iris feature with occluded pupil according to some embodiments of the disclosed technologies.

FIGS. 56A,B illustrate an ophthalmic shield 5600 with an encapsulated iris feature with occluded pupil 5602 according to some embodiments of the disclosed technologies. The feature 5602 may be 3D printed, a LaserJet printed disk, a hand-painted disk, fabric, or similar materials. The ophthalmic shield 5600 may include an active iris for a pinhole effect.

Figures 57A, 57B:
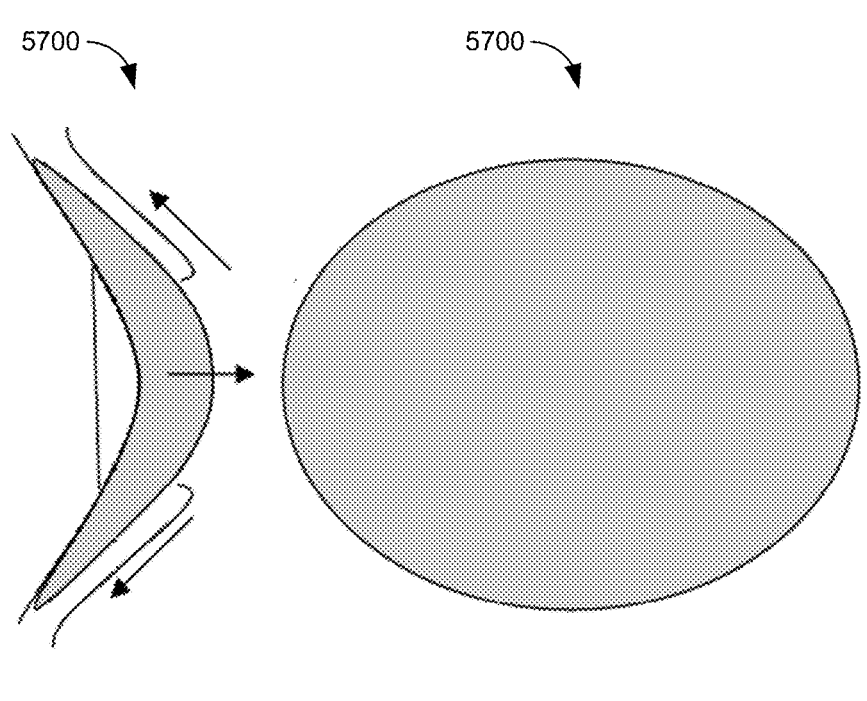
FIGS. 57A,B illustrates an ophthalmic shield designed to widen the aperture of the eye with structures outside the region of the cornea according to some embodiments of the disclosed technologies.

FIGS. 57A,B illustrates an ophthalmic shield 5700 designed to widen the aperture of the eye with structures outside the region of the cornea according to some embodiments of the disclosed technologies. For example, the widening may be blepharo-widening or globe enlargement for micropsia. The ophthalmic shield 5700 may include an area of increased thickness at the center to force the widening.

Figures 58A, 58B:
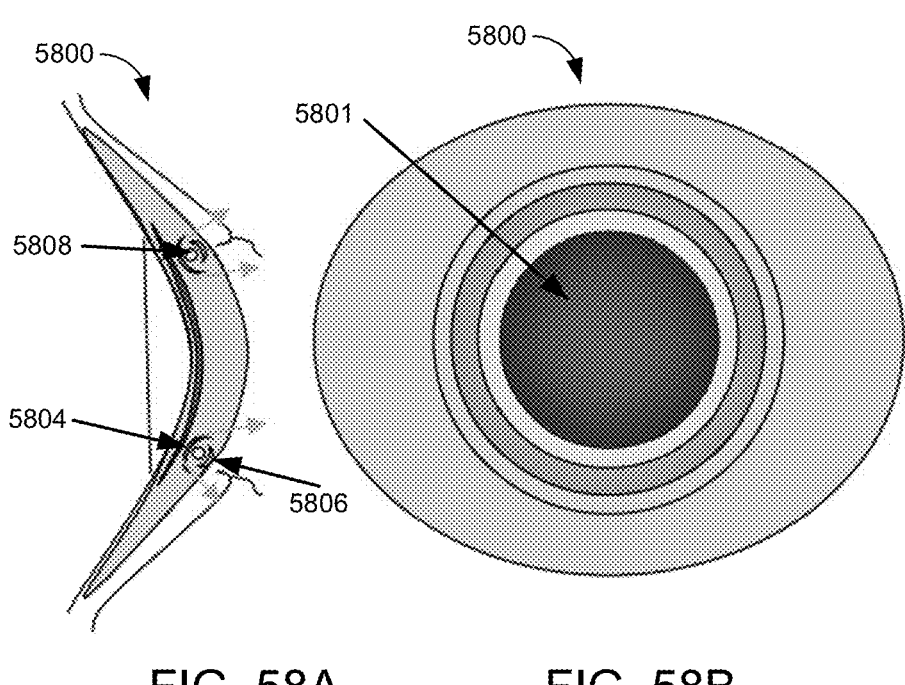
FIGS. 58A,B illustrate an ophthalmic shield with electrochromic elements according to some embodiments of the disclosed technologies.

FIGS. 58A,B illustrate an ophthalmic shield 5800 with electrochromic elements according to some embodiments of the disclosed technologies. The electrochromic elements may provide gradual illumination for dawn awaken effect or gradual blackout for sleep including blue light filtering. The electrochromic elements may include an electrochromic filter 5801, a light source 5808, a reflective material 5804, and a refractive material 5806.

Figures 59A, 59B:
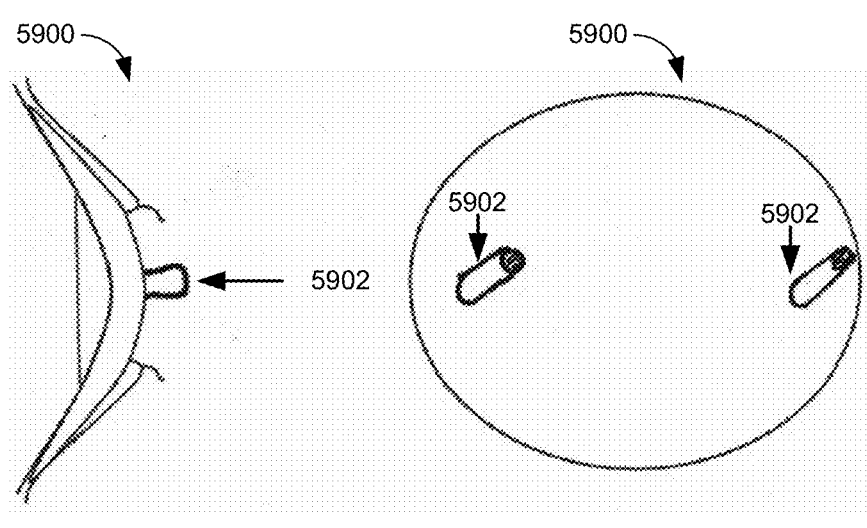
FIGS. 59A,B illustrate an ophthalmic shield with handles on the anterior surface for use in removal of the ophthalmic shield according to some embodiments of the disclosed technologies.

FIGS. 59A,B illustrate an ophthalmic shield 5900 with handles 5902 on the anterior surface for use in removal of the ophthalmic shield according to some embodiments of the disclosed technologies.

Figures 60A, 60B:
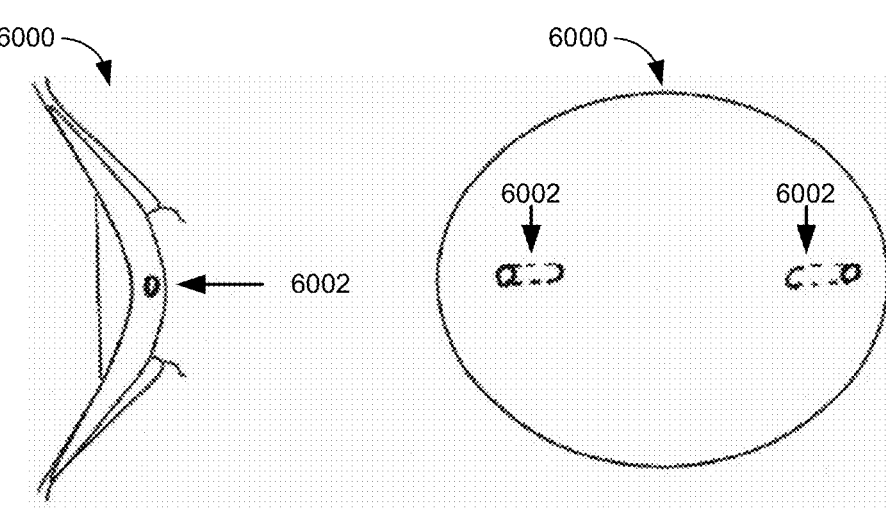
FIGS. 60A,B illustrate an ophthalmic shield with nasal and temporal ports for insertion of a device for applying and removing the ophthalmic shield according to some embodiments of the disclosed technologies.

FIGS. 60A,B illustrate an ophthalmic shield 6000 with nasal and temporal ports 6102 for insertion of a device for applying and removing the ophthalmic shield 6000 according to some embodiments of the disclosed technologies. These ports may also be used in conjunction with already existing extended release medications such as medicated polymer segments.

Figures 61A, 61B:
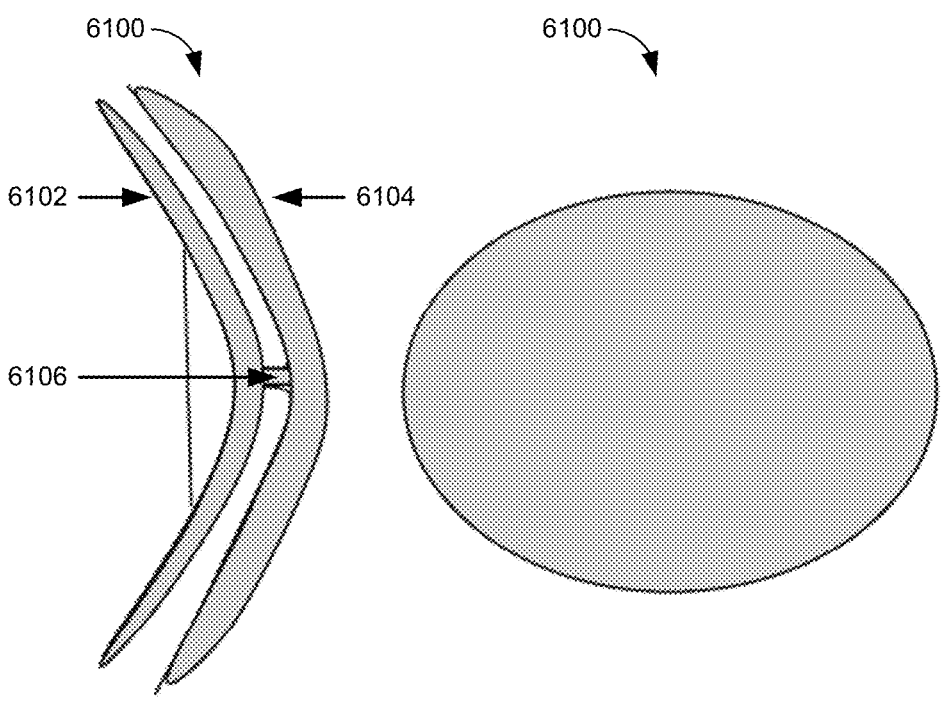
FIGS. 61A,B illustrate an ophthalmic shield having a double shield configuration according to some embodiments of the disclosed technologies.

FIGS. 61A,B illustrate an ophthalmic shield 6100 having a double shield configuration according to some embodiments of the disclosed technologies. The ophthalmic shield 6100 may include an inner shield 6102 to be placed under the lids to contact the ocular surface, an outer shield 6104 to be placed over the lids, and a connector 6106 to connect the inner shield 6102 with the outer shield 6104. The ophthalmic shield 6100 of FIG. 61 may have a multi-piece construction where the pieces slide or snap together.

Figures 62A, 62B:
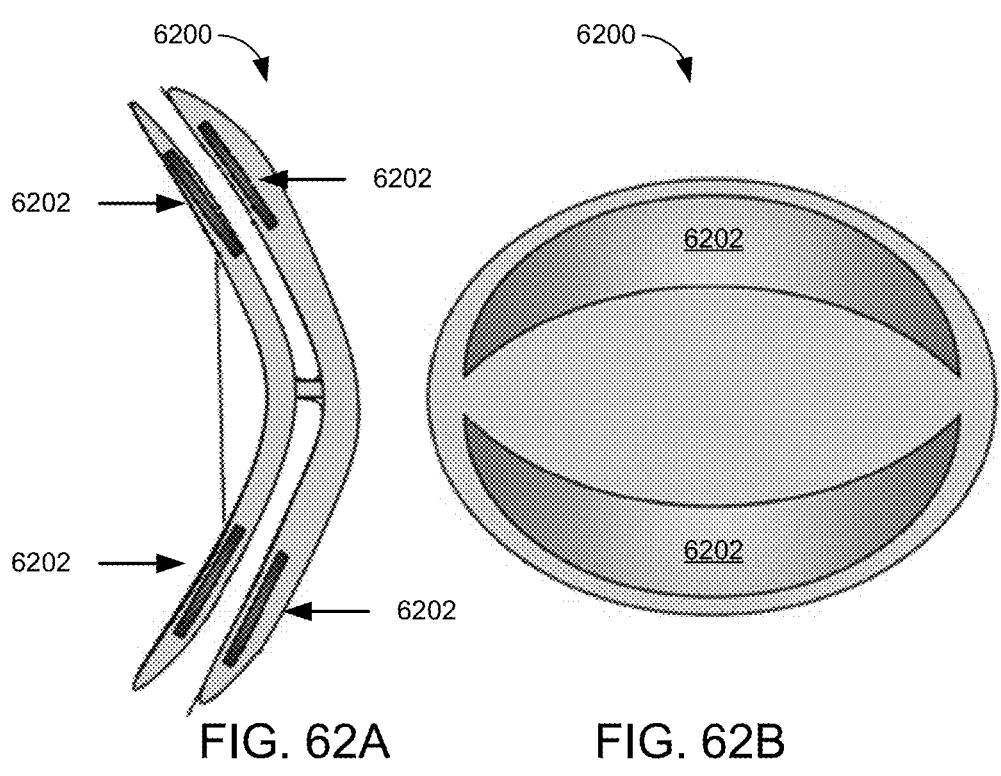
FIGS. 62A,B illustrate an ophthalmic shield having magnetic clamps according to some embodiments of the disclosed technologies.

FIGS. 62A,B illustrate an ophthalmic shield 6200 having magnetic clamps 6202 according to some embodiments of the disclosed technologies. The magnetic clamps may serve to hold the lids. In some embodiments, the magnetic clamps may be implemented as electromagnets. The electromagnets may be turned on and off, which may squeeze and release the lids, for example to express the meibomian glands. The ophthalmic shield 6200 may include thermal gel for heating or cooling. Additionally, these may contain materials which create endothermic or exothermic reactions to create heat or cold. The thermal gel may be disposed at 6202. The ophthalmic shield 6200 of FIG. 62 may have a multi-piece construction where the pieces slide or snap together.

Figures 63A, 63B:
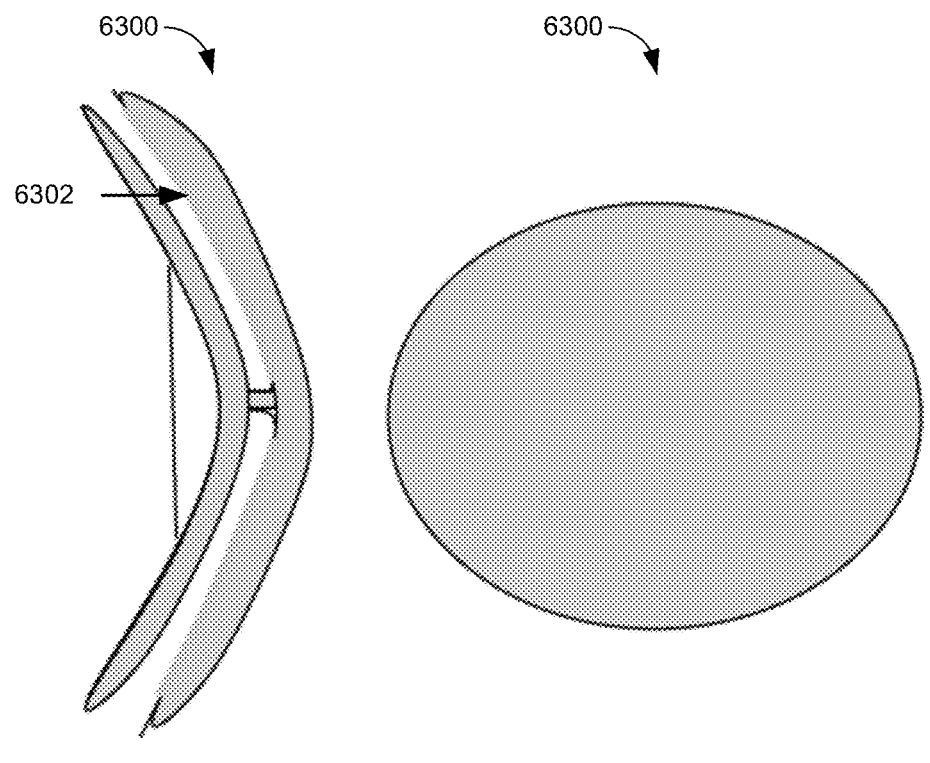
FIGS. 63A,B illustrate an ophthalmic shield having a double shield configuration with the outer shield having an adhesive inner side to adhere to the outside of the lid according to some embodiments of the disclosed technologies.

FIGS. 63A,B illustrate an ophthalmic shield 6300 having a double shield configuration with the outer shield having an adhesive inner side 6302 to adhere to the outside of the lid according to some embodiments of the disclosed technologies. The ophthalmic shield 6300 of FIG. 63 may have a multi-piece construction where the pieces slide or snap together.

Figures 64A, 64B:
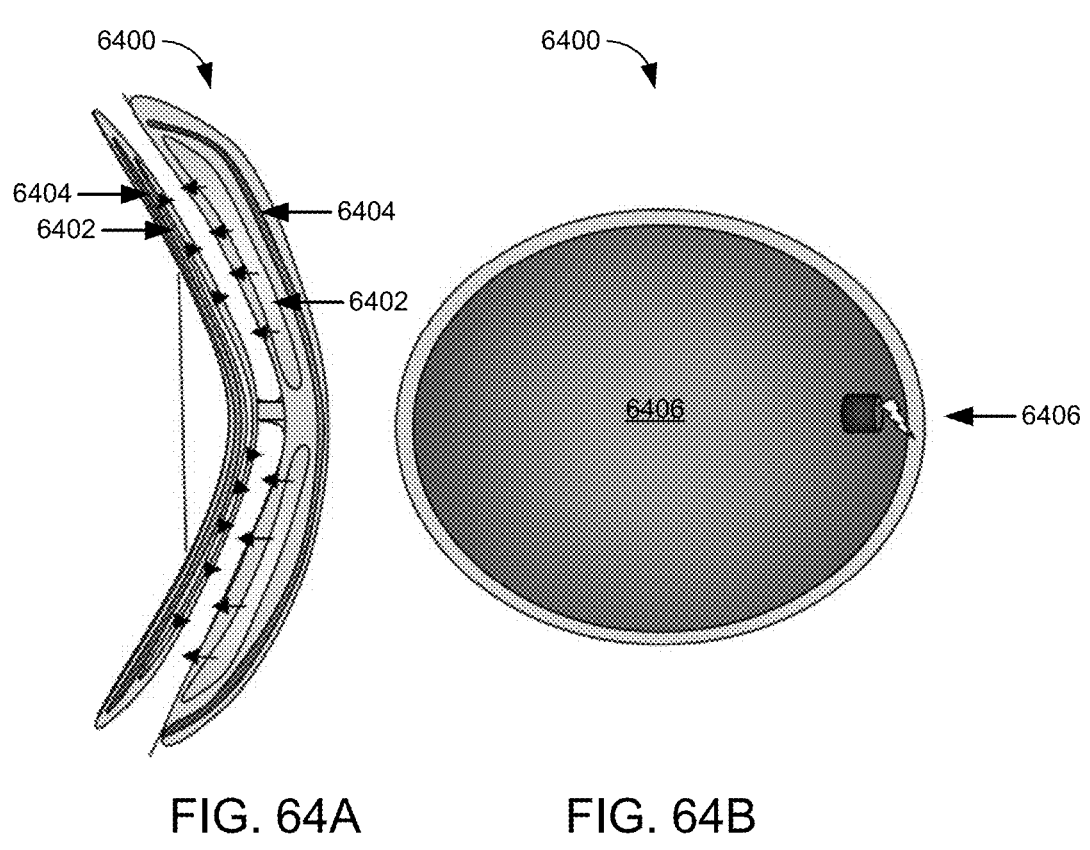
FIGS. 64A,B illustrate an ophthalmic shield that contains one or more treatment devices for treatment of the inner and outer lids according to some embodiments of the disclosed technologies.

FIGS. 64A,B illustrate an ophthalmic shield 6400 that contains one or more treatment devices for treatment of the inner and outer lids according to some embodiments of the disclosed technologies. The treatment devices may include electromagnetic spectrum emitters 6402 and protective filters 6404. The ophthalmic shield 6400 may include a power source 6406. The ophthalmic shield 6400 of FIG. 64 may have a multi-piece construction where the pieces slide or snap together.

Figures 65A, 65B:
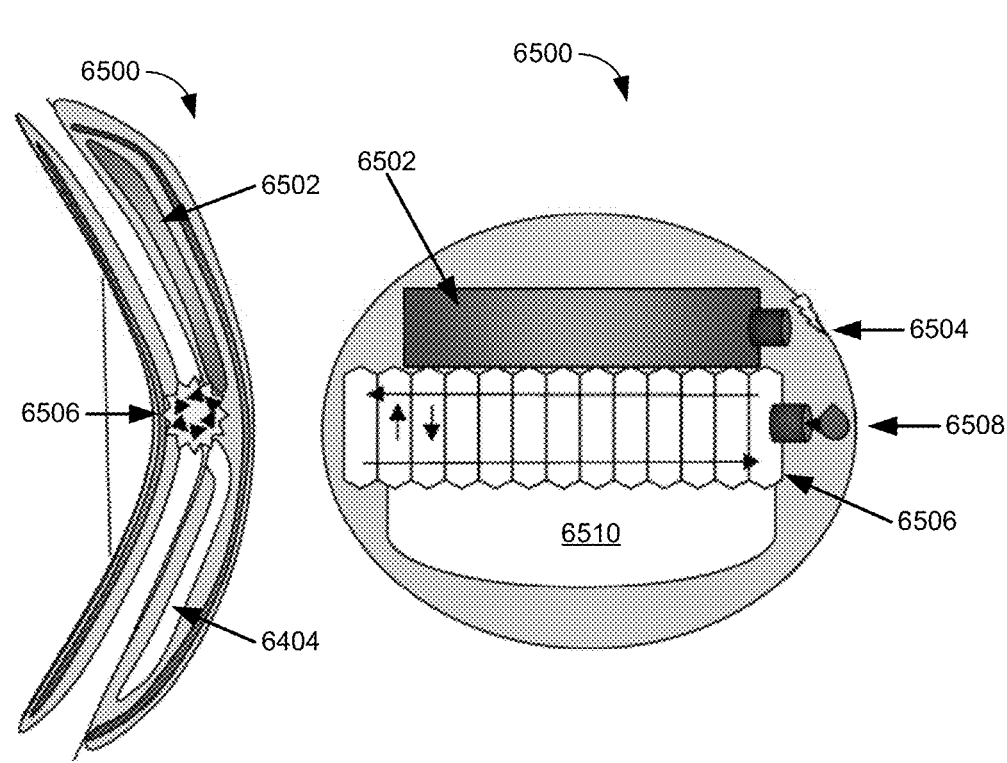
FIGS. 65A,B illustrate an ophthalmic shield that contains one or more treatment devices for the purpose of lid margin hygiene according to some embodiments of the disclosed technologies.

FIGS. 65A,B illustrate an ophthalmic shield 6500 that contains one or more treatment devices for the purpose of lid margin hygiene according to some embodiments of the disclosed technologies. The treatment devices may include a motor 6502, a power source 6504, a central rotation and translation brush 6506 at the lid margin and lash margin with or without aspiration at a port 6508, and an inferior collector 6510.

Figures 66A, 66B:
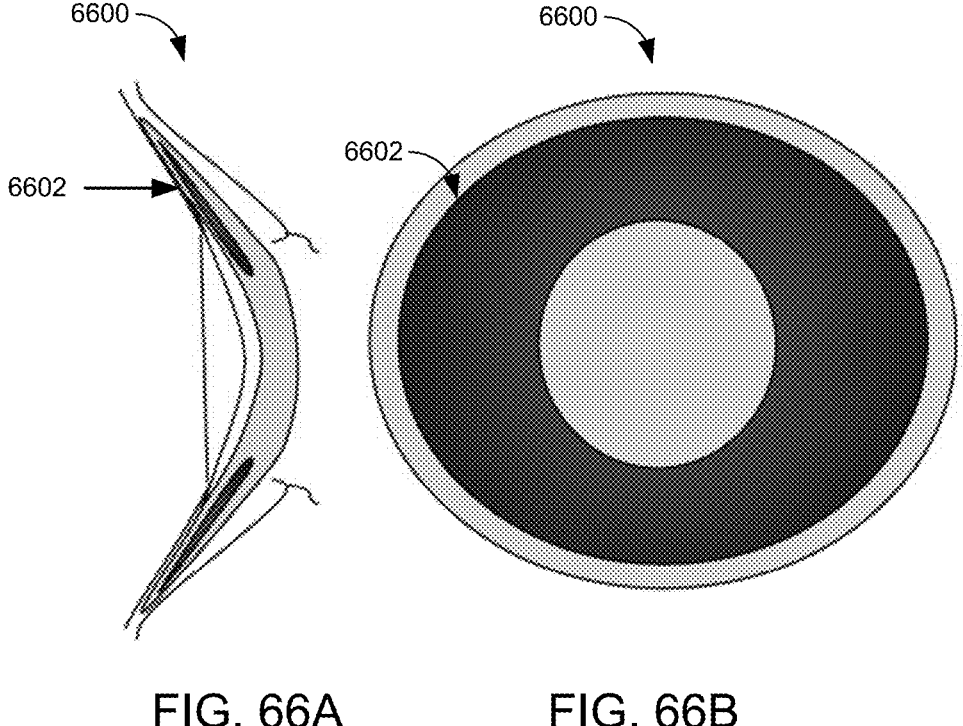
FIGS. 66A,B illustrate an ophthalmic shield with an annular-shaped malleable material to hold a shape according to some embodiments of the disclosed technologies.

FIGS. 66A,B illustrate an ophthalmic shield 6600 with an annular-shaped malleable material 6602 to hold a shape according to some embodiments of the disclosed technologies.

Figures 67A, 67B:
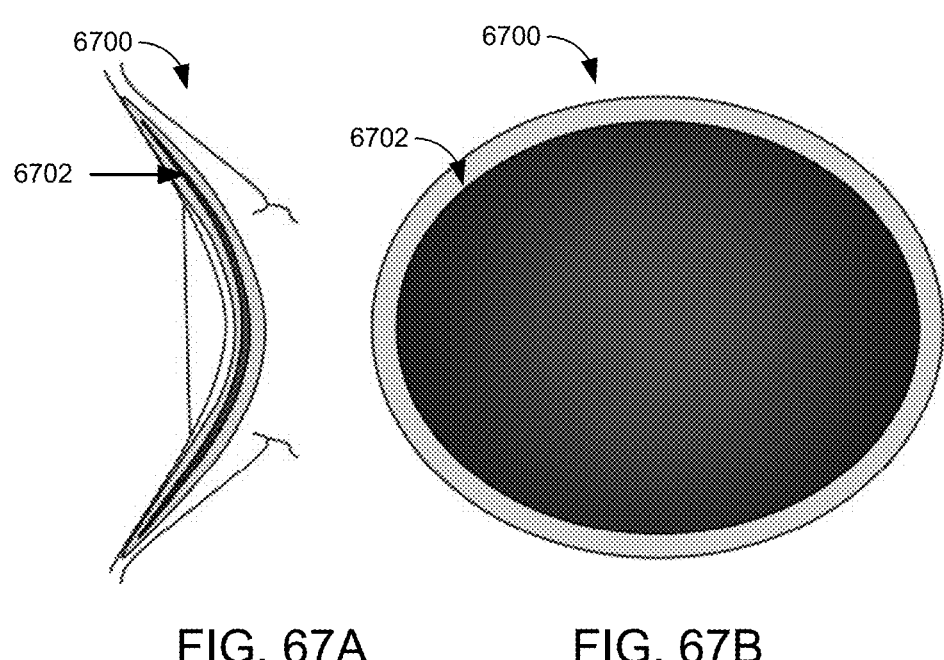
FIGS. 67A,B illustrate an ophthalmic shield with a disk-shaped malleable material to hold a shape according to some embodiments of the disclosed technologies.

FIGS. 67A,B illustrate an ophthalmic shield 6700 with a disk-shaped malleable material 6702 to hold a shape according to some embodiments of the disclosed technologies. The material may be a flexible film or mesh, or similar materials.

Figures 68A, 68B:
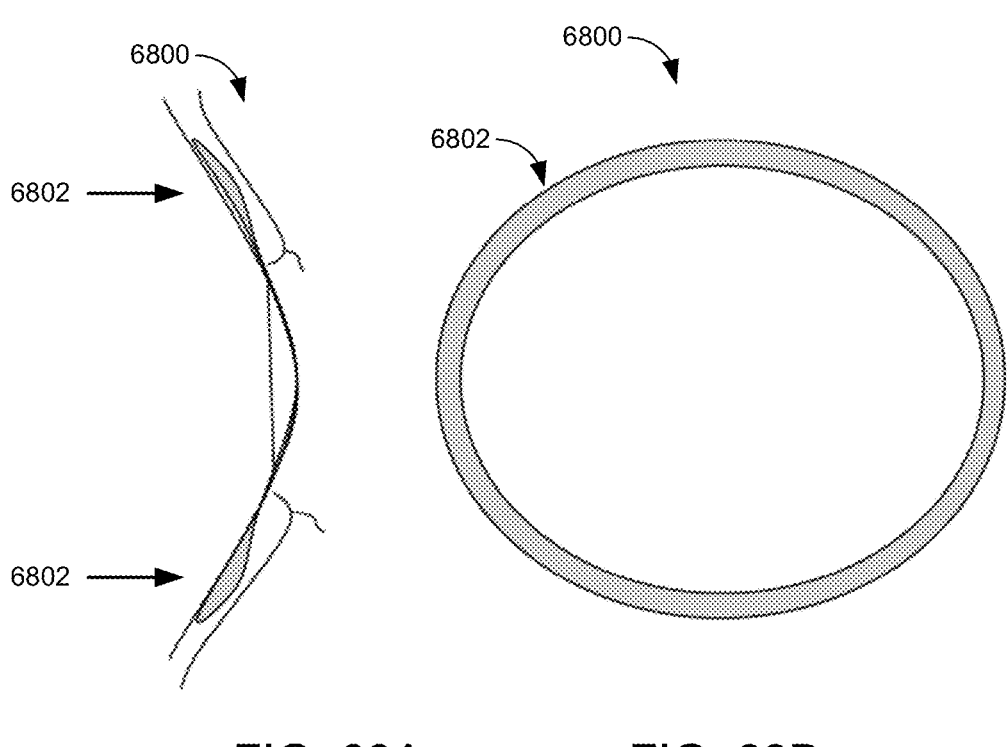
FIGS. 68A,B illustrate an ophthalmic shield with a flat or domed fornix ring according to some embodiments of the disclosed technologies.

FIGS. 68A,B illustrate an ophthalmic shield 6800 with a flat or domed fornix ring 6802 according to some embodiments of the disclosed technologies. The disclosed fornix rings may be used to prevent symblepharon formation and maintain the fornix integrity when healing after surgical procedures, traumas or cicatricial diseases and the like.

Figures 69A, 69B:
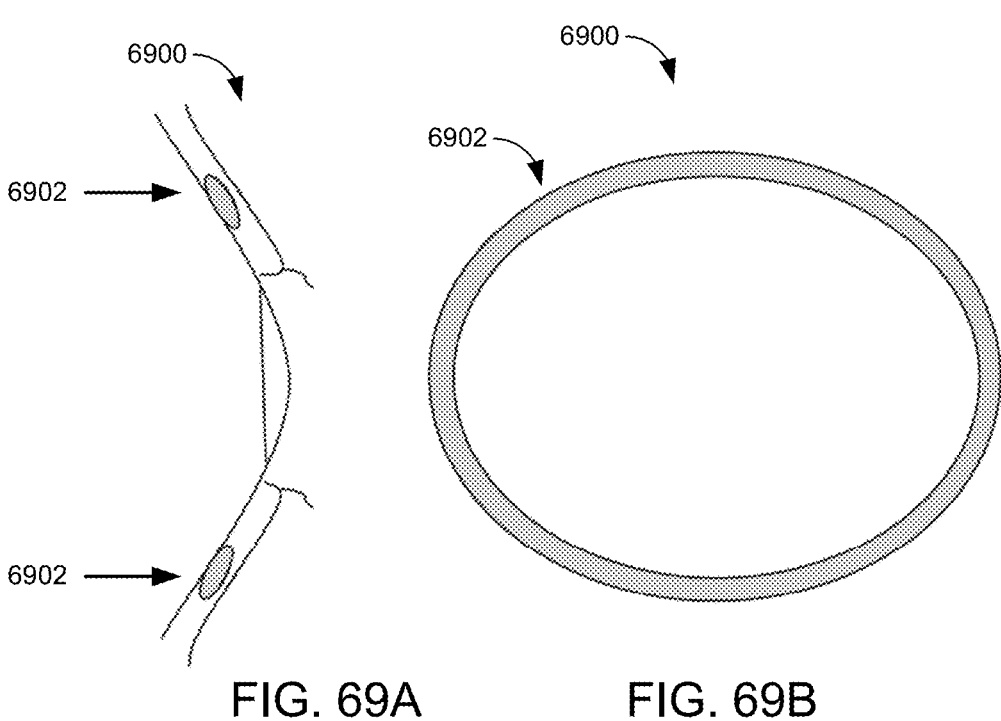
FIGS. 69A,B illustrate an ophthalmic shield with a fornix ring having an oval cross-section according to some embodiments of the disclosed technologies.

FIGS. 69A,B illustrate an ophthalmic shield 6900 with a fornix ring 6902 having an oval cross-section according to some embodiments of the disclosed technologies.

Figures 70A, 70B:
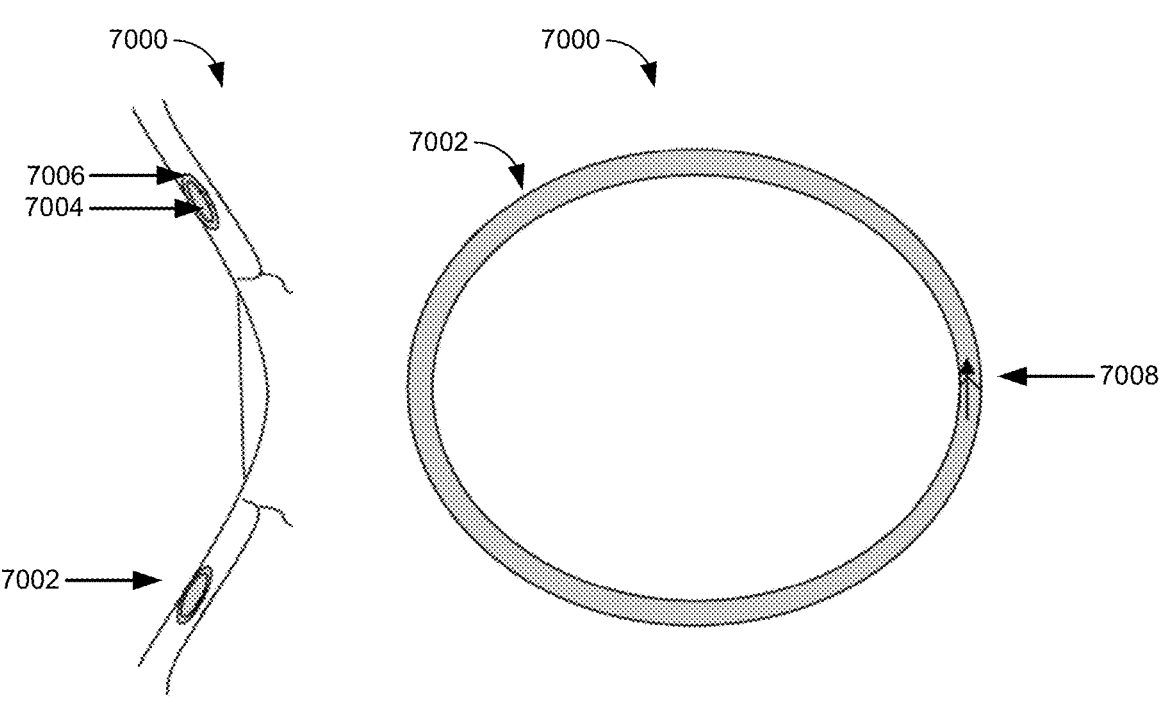
FIGS. 70A,B illustrate an ophthalmic shield with an adjustable fornix ring according to some embodiments of the disclosed technologies.

FIGS. 70A,B illustrate an ophthalmic shield 7000 with an adjustable fornix ring 7002 according to some embodiments of the disclosed technologies. The adjustable fornix ring 7002 may have a multi-piece construction that may include an inner ring 7004, an outer ring 7006, and an overlap 7008 to allow for adjusting the diameter of the fornix ring 7002.

FIG. 71 illustrates a flow chart for selecting the parameters of an ophthalmic shield according to some embodiments of the disclosed technology. The elements of the disclosed processes are presented in one arrangement. However, it should be understood that one or more elements of the processes may be performed in a different order, in parallel, omitted entirely, and the like. Furthermore, the processes may include other elements in addition to those presented.

Referring to FIG. 71, the process 7100 may include obtaining at least one metric of an eye of a patient, at 7102.

In some embodiments, obtaining the at least one metric may include obtaining a radius of curvature of a cornea of a patient; and determining the at least one parameter may include selecting a base curve radius of a central zone of an ophthalmic shield to be manufactured based on the radius of curvature of the cornea of the patient.

The process 7100 may include determining, based on the at least one metric of the eye of the patient, at least one parameter for manufacturing an ophthalmic shield to be worn on the eye of the patient, wherein the ophthalmic shield has a minimum horizontal dimension of 18 mm and a minimum vertical dimension of 15 mm, at 7104.

In some embodiments, obtaining the at least one metric may include conducting objective and/or subjective refraction of the eye of the patient; and determining the at least one parameter may include determining a refractive power of an optic zone of the ophthalmic shield.

In some embodiments, obtaining the at least one metric may include obtaining the at least one measurement of a sagittal depth of the eye of the patient at a chord outside the cornea; and determining the at least one parameter may include determining a sagittal depth parameter of the ophthalmic shield over the sclera of the eye of the patient.

In some embodiments, obtaining the at least one metric may include obtaining upper and lower lid positions relative to the superior and inferior limbus of the eye of the patient; and determining the at least one parameter may include determining, based on the obtained upper and lower lid positions, the at least one of: a location of upper and lower rotational stabilization features of the ophthalmic shield, or one or more parameters of one or more lid speculum features for an anterior aspect of the ophthalmic shield.

In some embodiments, obtaining the at least one metric may include obtaining upper and lower lid fornix depths of the eye of the patient; and determining the at least one parameter may include determining a vertical dimension of the ophthalmic shield based on the obtained upper and lower lid fornix depths.

In some embodiments, obtaining the at least one metric may include obtaining: a horizontal distance between a medial canthus and a lateral canthus of the eye of the patient, or a horizontal distance between landmarks placed at the medial canthus and the lateral canthus; and determining the at least one parameter may include determining a horizontal dimension of the ophthalmic shield based on the obtained horizontal distance.

In some embodiments, obtaining the at least one metric may include obtaining a first distance from a medial canthus to a medial aspect of the cornea of the eye of the patient and obtaining a second distance from a lateral canthus to a temporal aspect of the cornea of the eye of the patient; and determining the at least one parameter may include determining an asymmetry of horizontal dimensions of the ophthalmic shield from a geometric center of the ophthalmic shield based on the obtained first and second distances.

In some embodiments, obtaining the at least one metric may include obtaining one or more parameters including a residual refraction or wavefront refraction and registration of an optic zone of the ophthalmic shield with a predicate contact lens or ophthalmic shield placed on the eye of the patient; and determining the at least one parameter may include determining a low and higher order aberration correction of the optic zone of the ophthalmic shield based on the one or more obtained parameters.

Referring again to FIG. 71, the process 7100 may include manufacturing the ophthalmic shield according to the determined at least one parameter. For example, the process 7100 may include creating a cutting file and fabricating an ophthalmic shield, at 7106. For example, a polish-free computer numerically controlled lathe may be employed to cut the ophthalmic shield. Cutting may be followed by a contour inspection of the posterior surface of the ophthalmic shield to determine the finished posterior surface matches the intended shape.

The process 7100 may include applying and evaluating the ophthalmic shield, at 7108. This may include capturing an image of the ophthalmic shield on the eye of the patient. The image may be analyzed to assess the relationship between the eye and the ophthalmic shield. The process 7100 may conclude with dispensing the ophthalmic shield, and conducting one or more follow-up evaluations, at 7110.

FIG. 72 illustrates a flow chart for selecting the parameters of an ophthalmic shield according to some embodiments of the disclosed technology. The elements of the disclosed processes are presented in one arrangement. However, it should be understood that one or more elements of the processes may be performed in a different order, in parallel, omitted entirely, and the like. Furthermore, the processes may include other elements in addition to those presented.

Referring to FIG. 72, the process 7200 may include obtaining at least one metric of an eye of a patient, at 7202. In some embodiments, obtaining the at least one metric may include obtaining a radius of curvature of a cornea of a patient; and determining the at least one parameter may include selecting a base curve radius of a central zone of an ophthalmic shield to be manufactured based on the radius of curvature of the cornea of the patient.

The process 7200 may include determining, based on the at least one metric of the eye of the patient, at least one parameter for manufacturing an ophthalmic shield to be worn on the eye of the patient, wherein the ophthalmic shield has a minimum horizontal dimension of 18 mm and a minimum vertical dimension of 15 mm, at 7204. The metrics and parameters may be as described above regarding process 7100 of FIG. 71.

Referring again to FIG. 72, the process 7200 may include manufacturing the ophthalmic shield according to the determined at least one parameter. For example, the process 7200 may include creating a cutting file and fabricating an ophthalmic shield, at 7206. For example, a polish-free computer numerically controlled lathe may be employed to cut the ophthalmic shield. Cutting may be followed by a contour inspection of the posterior surface of the ophthalmic shield to determine the finished posterior surface matches the intended shape.

The process 7200 may include applying and evaluating the ophthalmic shield, at 7208. This may include capturing an image of the ophthalmic shield on the eye of the patient. The image may be analyzed to assess the relationship between the eye and the ophthalmic shield. The process 7200 may conclude with dispensing the ophthalmic shield, and conducting one or more follow-up evaluations, at 7210.

FIG. 73 illustrates a flow chart for selecting the parameters of an ophthalmic shield according to some embodiments of the disclosed technology. The elements of the disclosed processes are presented in one arrangement. However, it should be understood that one or more elements of the processes may be performed in a different order, in parallel, omitted entirely, and the like. Furthermore, the processes may include other elements in addition to those presented.

Referring to FIG. 73, the process 7300 may include obtaining at least one metric of an eye of a patient, at 7302.

In some embodiments, obtaining the at least one metric may include obtaining a radius of curvature of a cornea of a patient; and determining the at least one parameter may include selecting a base curve radius of a central zone of an ophthalmic shield to be manufactured based on the radius of curvature of the cornea of the patient. The metrics may be obtained by taking an impression of an eye and scanning the impression. The process may include creating a cutting file for a back surface mold, creating a cutting file for a front surface mold, and molding the shield.

The process 7300 may include determining, based on the at least one metric of the eye of the patient, at least one parameter for manufacturing an ophthalmic shield to be worn on the eye of the patient, wherein the ophthalmic shield has a minimum horizontal dimension of 18 mm and a minimum vertical dimension of 15 mm, at 7304. The metrics and parameters may be as described above regarding process 7100 of FIG. 71.

Referring again to FIG. 73, the process 7300 may include manufacturing the ophthalmic shield according to the determined at least one parameter. For example, the process 7300 may include creating a cutting file and fabricating an ophthalmic shield, at 7306. For example, a polish-free computer numerically controlled lathe may be employed to cut the ophthalmic shield. Cutting may be followed by a contour inspection of the posterior surface of the ophthalmic shield to determine the finished posterior surface matches the intended shape.

The process 7300 may include applying and evaluating the ophthalmic shield, at 7308. This may include capturing an image of the ophthalmic shield on the eye of the patient. The image may be analyzed to assess the relationship between the eye and the ophthalmic shield. The process 7300 may conclude with dispensing the ophthalmic shield, and conducting one or more follow-up evaluations, at 7310.

Figure 74:
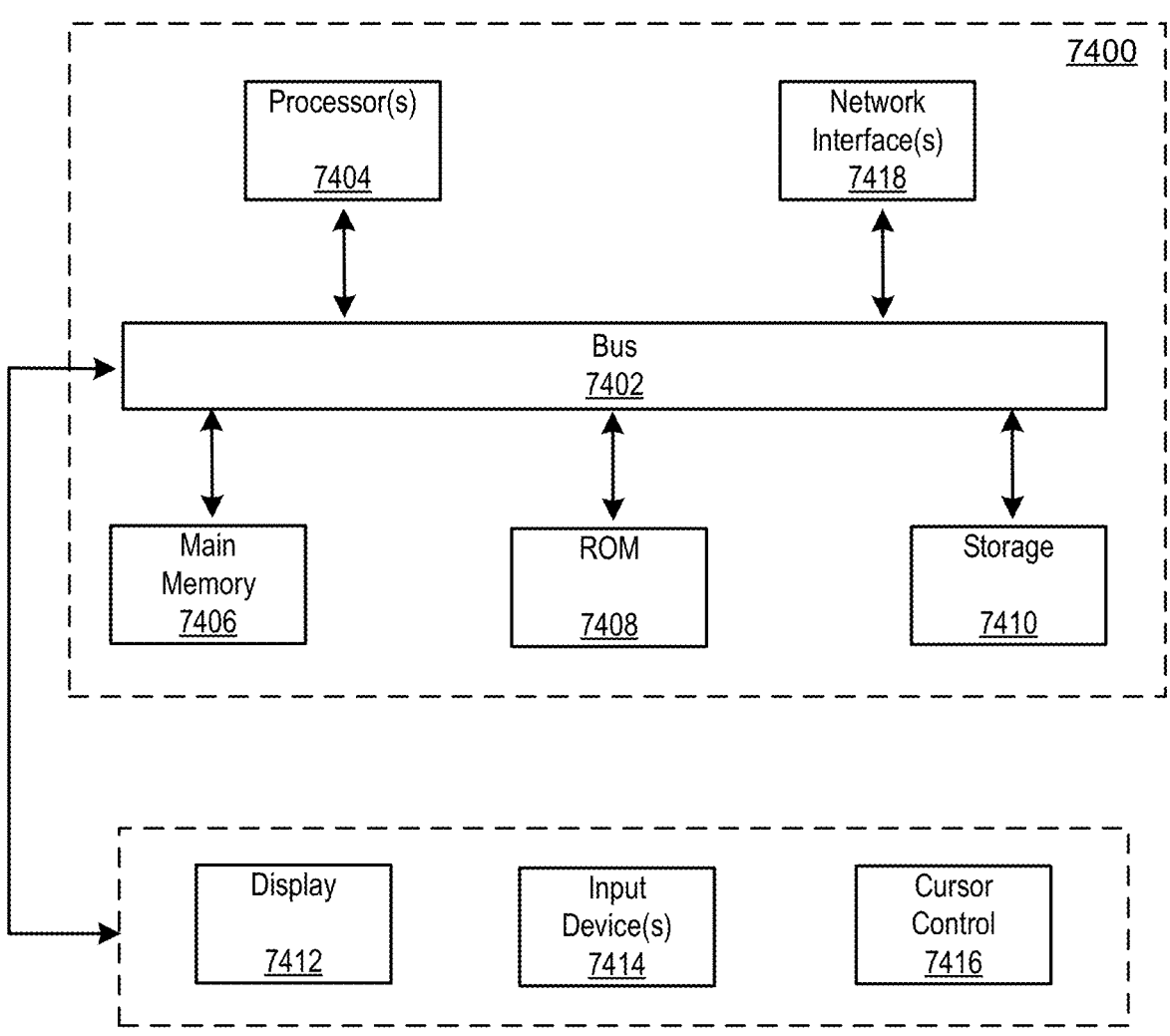
FIG. 74 depicts a block diagram of an example computer system in which embodiments described herein may be implemented.

FIG. 74 depicts a block diagram of an example computer system 7400 in which embodiments described herein may be implemented. The computer system 7400 includes a bus 7402 or other communication mechanism for communicating information, one or more hardware processors 7404 coupled with bus 7402 for processing information. Hardware processor(s) 7404 may be, for example, one or more general purpose microprocessors.

The computer system 7400 also includes a main memory 7406, such as a random access memory (RAM), cache and/or other dynamic storage devices, coupled to bus 7402 for storing information and instructions to be executed by processor 7404. Main memory 7406 also may be used for storing temporary variables or other intermediate information during execution of instructions to be executed by processor 7404. Such instructions, when stored in storage media accessible to processor 7404, render computer system 7400 into a special-purpose machine that is customized to perform the operations specified in the instructions.

The computer system 7400 further includes a read only memory (ROM) 7408 or other static storage device coupled to bus 7402 for storing static information and instructions for processor 7404. A storage device 7410, such as a magnetic disk, optical disk, or USB thumb drive (Flash drive), etc., is provided and coupled to bus 7402 for storing information and instructions.

The computer system 7400 may be coupled via bus 7402 to a display 7412, such as a liquid crystal display (LCD) (or touch screen), for displaying information to a computer user. An input device 7414, including alphanumeric and other keys, is coupled to bus 7402 for communicating information and command selections to processor 7404. Another type of user input device is cursor control 7416, such as a mouse, a trackball, or cursor direction keys for communicating direction information and command selections to processor 7404 and for controlling cursor movement on display 7412. In some embodiments, the same direction information and command selections as cursor control may be implemented via receiving touches on a touch screen without a cursor.

The computing system 7400 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "component," "engine," "system," "database," data store," and the like, as used herein, can refer to logic embodied in hardware or firmware, or to a collection of software instructions, possibly having entry and exit points, written in a programming language, such as, for example, Java, C or C++. A software component may be compiled and linked into an executable program, installed in a dynamic link library, or may be written in an interpreted programming language such as, for example, BASIC, Perl, or Python. It will be appreciated that software components may be callable from other components or from themselves, and/or may be invoked in response to detected events or interrupts. Software components configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware components may be comprised of connected logic units, such as gates and flip-flops, and/or may be comprised of programmable units, such as programmable gate arrays or processors.

The computer system 7400 may implement the techniques described herein using customized hard-wired logic, one or more ASICs or FPGAs, firmware and/or program logic which in combination with the computer system causes or programs computer system 7400 to be a special-purpose machine. According to one embodiment, the techniques herein are performed by computer system 7400 in response to processor(s) 7404 executing one or more sequences of one or more instructions contained in main memory 7406. Such instructions may be read into main memory 7406 from another storage medium, such as storage device 7410. Execution of the sequences of instructions contained in main memory 7406 causes processor(s) 7404 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 7410. Volatile media includes dynamic memory, such as main memory 7406. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between non-transitory media. For example, transmission media includes coaxial cables, copper wire and fiber optics, including the wires that comprise bus 7402. Transmission media can also take the form of acoustic or light waves, such as those generated during radio-wave and infra-red data communications.

The computer system 7400 also includes a communication interface 7418 coupled to bus 7402. Network interface 7418 provides a two-way data communication coupling to one or more network links that are connected to one or more local networks. For example, communication interface 7418 may be an integrated services digital network (ISDN) card, cable modem, satellite modem, or a modem to provide a data communication connection to a corresponding type of telephone line. As another example, network interface 7418 may be a local area network (LAN) card to provide a data communication connection to a compatible LAN (or a WAN component to communicate with a WAN). Wireless links may also be implemented. In any such implementation, network interface 7418 sends and receives electrical, electromagnetic or optical signals that carry digital data streams representing various types of information.

A network link typically provides data communication through one or more networks to other data devices. For example, a network link may provide a connection through local network to a host computer or to data equipment operated by an Internet Service Provider (ISP). The ISP in turn provides data communication services through the world wide packet data communication network now commonly referred to as the "Internet." Local network and Internet both use electrical, electromagnetic or optical signals that carry digital data streams. The signals through the various networks and the signals on network link and through communication interface 7418, which carry the digital data to and from computer system 7400, are example forms of transmission media.

The computer system 7400 can send messages and receive data, including program code, through the network (s), network link and communication interface 7418. In the Internet example, a server might transmit a requested code for an application program through the Internet, the ISP, the local network and the communication interface 7418.

The received code may be executed by processor 7404 as it is received, and/or stored in storage device 7410, or other non-volatile storage for later execution.

Each of the processes, methods, and algorithms described in the preceding sections may be embodied in, and fully or partially automated by, code components executed by one or more computer systems or computer processors comprising computer hardware. The one or more computer systems or computer processors may also operate to support performance of the relevant operations in a "cloud computing" environment or as a "software as a service" (SaaS). The processes and algorithms may be implemented partially or wholly in application-specific circuitry. The various features and processes described above may be used independently of one another, or may be combined in various ways. Different combinations and sub-combinations are intended to fall within the scope of this disclosure, and certain method or process blocks may be omitted in some implementations. The methods and processes described herein are also not limited to any particular sequence, and the blocks or states relating thereto can be performed in other sequences that are appropriate, or may be performed in parallel, or in some other manner. Blocks or states may be added to or removed from the disclosed example embodiments. The performance of certain of the operations or processes may be distributed among computer systems or computers processors, not only residing within a single machine, but deployed across a number of machines.

As used herein, a circuit might be implemented utilizing any form of hardware, or a combination of hardware and software. For example, one or more processors, controllers, ASICs, PLAs, PALs, CPLDs, FPGAs, logical components, software routines or other mechanisms might be implemented to make up a circuit. In implementation, the various circuits described herein might be implemented as discrete circuits or the functions and features described can be shared in part or in total among one or more circuits. Even though various features or elements of functionality may be individually described or claimed as separate circuits, these features and functionality can be shared among one or more common circuits, and such description shall not require or imply that separate circuits are required to implement such features or functionality. Where a circuit is implemented in whole or in part using software, such software can be implemented to operate with a computing or processing system capable of carrying out the functionality described with respect thereto, such as computer system 7400.

As used herein, the term "or" may be construed in either an inclusive or exclusive sense. Moreover, the description of resources, operations, or structures in the singular shall not be read to exclude the plural. Conditional language, such as, among others, "can," "could," "might," or "may," unless specifically stated otherwise, or otherwise understood within the context as used, is generally intended to convey that certain embodiments include, while other embodiments do not include, certain features, elements and/or steps.

Terms and phrases used in this document, and variations thereof, unless otherwise expressly stated, should be construed as open ended as opposed to limiting. Adjectives such as "conventional," "traditional," "normal," "standard," "known," and terms of similar meaning should not be construed as limiting the item described to a given time period or to an item available as of a given time, but instead should be read to encompass conventional, traditional, normal, or standard technologies that may be available or known now or at any time in the future. The presence of broadening words and phrases such as "one or more," "at least," "but not limited to" or other like phrases in some instances shall not be read to mean that the narrower case is intended or required in instances where such broadening phrases may be absent.

What is claimed is:

1. A method comprising:
   obtaining at least one metric of an eye of a patient; and
   determining, based on the at least one metric of the eye of the patient, at least one parameter for manufacturing an ophthalmic shield to be worn on the eye of the patient, wherein the ophthalmic shield has a minimum horizontal dimension of 18 mm and a minimum vertical dimension of 15 mm;

wherein obtaining at least one metric comprises obtaining upper and lower lid positions relative to a superior and inferior limbus of the eye of the patient; and determining at least one parameter comprises determining, based on the obtained upper and lower lid positions, one or more parameters of one or more lid speculum features for an anterior aspect of the ophthalmic shield.

2. The method of claim 1, wherein:

obtaining at least one metric comprises obtaining a radius of curvature of a cornea of a patient; and determining at least one parameter comprises selecting a base curve radius of a central zone of an ophthalmic shield to be manufactured based on the radius of curvature of the cornea of the patient.

3. The method of claim 1, wherein:

obtaining at least one metric comprises conducting objective and/or subjective refraction of the eye of the patient; and determining at least one parameter comprises determining a refractive power of an optic zone of the ophthalmic shield.

4. The method of claim 1, wherein:

obtaining at least one metric comprises obtaining at least one measurement of a sagittal depth of the eye of the patient at a chord outside the cornea; and determining at least one parameter comprises determining a sagittal depth parameter of the ophthalmic shield over the sclera of the eye of the patient.

5. The method of claim 1, wherein:

obtaining at least one metric comprises obtaining upper and lower lid fornix depths of the eye of the patient; and determining at least one parameter comprises determining a vertical dimension of the ophthalmic shield based on the obtained upper and lower lid fornix depths.

6. The method of claim 1, wherein:

obtaining at least one metric comprises obtaining:

a horizontal distance between an inner canthus and an outer canthus of the eye of the patient, or a horizontal distance between landmarks placed at the inner canthus and the outer canthus; and determining at least one parameter comprises determining a horizontal dimension of the ophthalmic shield based on the obtained horizontal distance.

7. The method of claim 1, wherein:

obtaining at least one metric comprises obtaining a first distance from a nasal canthus to a nasal aspect of the cornea of the eye of the patient and obtaining a second distance from a temporal canthus to a temporal aspect of the cornea of the eye of the patient; and determining at least one parameter comprises determining an asymmetry of horizontal dimensions of the ophthalmic shield from a geometric center of the ophthalmic shield based on the obtained first and second distances.

8. The method of claim 1, wherein:

obtaining at least one metric comprises obtaining one or more parameters including a residual refraction or wavefront refraction and registration of an optic zone of the ophthalmic shield with a predicate lens or shield placed on the eye of the patient; and determining at least one parameter comprises determining a low and higher order aberration correction of the optic zone of the ophthalmic shield based on the one or more obtained parameters.

9. The method of claim 1, further comprising:

manufacturing the ophthalmic shield according to the determined at least one parameter.

10. The method of claim 1, wherein obtaining at least one metric of an eye of a patient comprises:

capturing, with a sensor, data describing the eye of the patient.

11. The method of claim 1, wherein obtaining at least one metric of an eye of a patient comprises:

obtaining a physical impression of the eye of the patient.

\* \* \* \* \*